US011389532B2

(12) United States Patent
Clark et al.

(10) Patent No.: US 11,389,532 B2
(45) Date of Patent: Jul. 19, 2022

(54) THERAPEUTIC VACCINE FOR HEPATITIS B VIRUS (HBV) USING THE HBV PRES1 AND/OR PRES2, AND/OR S-HBSAG REGIONS OF THE HBV ENVELOPE PROTEIN

(71) Applicant: University of Washington, Seattle, WA (US)

(72) Inventors: Edward A. Clark, Seattle, WA (US); Che-Leung Law, Seattle, WA (US); Deborah Fuller, Seattle, WA (US); Michael Gale, Seattle, WA (US)

(73) Assignees: University of Washington, Seattle, WA (US); Abacus Bioscience, Inc., Sammamish, WA (US)

( * ) Notice: Subject to any disclaimer, the term of this patent is extended or adjusted under 35 U.S.C. 154(b) by 114 days.

(21) Appl. No.: 16/764,950

(22) PCT Filed: Nov. 15, 2018

(86) PCT No.: PCT/US2018/061218
§ 371 (c)(1),
(2) Date: May 18, 2020

(87) PCT Pub. No.: WO2019/099624
PCT Pub. Date: May 23, 2019

(65) Prior Publication Data
US 2020/0345838 A1 Nov. 5, 2020

Related U.S. Application Data

(60) Provisional application No. 62/587,051, filed on Nov. 16, 2017.

(51) Int. Cl.
*A61K 39/29* (2006.01)
*A61P 31/20* (2006.01)
*C07K 16/28* (2006.01)
*A61K 39/00* (2006.01)

(52) U.S. Cl.
CPC ............ *A61K 39/292* (2013.01); *A61P 31/20* (2018.01); *C07K 16/2878* (2013.01); *C07K 16/2896* (2013.01); *A61K 2039/6056* (2013.01); *C07K 2317/524* (2013.01); *C07K 2317/526* (2013.01); *C07K 2317/56* (2013.01); *C07K 2317/622* (2013.01)

(58) Field of Classification Search
CPC .......... A61K 39/292; A61K 2039/6056; A61K 39/12; A61P 31/20; C07K 16/2878; C07K 16/2896; C07K 2317/524; C07K 2317/526; C07K 2317/56; C07K 2317/622; C07K 2319/00; C12N 2730/10134
See application file for complete search history.

(56) References Cited

U.S. PATENT DOCUMENTS

| 10,196,614 | B2 * | 2/2019 | Clark | ................ C07K 16/2896 |
| 10,563,179 | B2 * | 2/2020 | Clark | ........................ A61P 3/10 |
| 2012/0020965 | A1 * | 1/2012 | Chaplin | ................ A61P 35/00 424/134.1 |
| 2013/0017200 | A1 | 1/2013 | Scheer et al. | |
| 2013/0209395 | A1 | 8/2013 | Weiner et al. | |
| 2017/0260258 | A1 | 9/2017 | Hong et al. | |

FOREIGN PATENT DOCUMENTS

| WO | 97/04000 | 2/1997 |
| WO | 2009/036228 | 3/2009 |
| WO | 2017/176319 | 10/2017 |
| WO | 2017176319 A1 | 10/2017 |

OTHER PUBLICATIONS

Lloyd et al. Protein Engineering, Design & Selection 22:159-168 (Year: 2009).*
Edwards et al., J Mol Biol. 334(1): 103-118 (Year: 2003).*
Rudikoff et al., Proc. Natl. Acad. Sci. USA, 79:1979-1983 (Year: 1982).*
Alving et al. (2012) Adjuvants for human vaccines. Curr Opin Immunol. 24:310-5.
Beck et al. (2007) Hepatitis 8 virus replication. World J Gastroenterol WJG. 13:48-64.
Bertoletti et al. (2016) Adaptive immunity in H8V infection. J Hepatol. 64:S71-83.
Bian et al. (2017) Vaccines Targeting PreS1 Domain Overcome Immune Tolerance in HBV Carrier Mice. Hepatology. Apr. 26. doi:1002/hep.29239.
Bruss V. (2007) Hepatitis B virus morphogenesis. World J Gastroenterol. 13:65-73.
Chaplin et al. (2013) Targeting antigens to CD180 rapidly induces antigen-specific IgG, affinity maturation and immunologic memory. J Exp Med. 210:2135-46.
Chaplin et al. (2011) Anti-CD180 (RP105) activates B cells to rapidly produce polyclonal Ig via aT cell and My088-independent pathway. J Immunol. 187:4199-209.
Chappell et al. (2014) Controlling immune responses by targeting antigensto dendritic cell subsets and B Cells. Int Immunol. 26:3-11.
Chen et al. (2016) Selection of affinity-improved neutralizing human scFv against HBV PreS1 from CDR3 VHNL mutant library. Biologicals. July:44(4):271-5.

(Continued)

*Primary Examiner* — Phuong Huynh
(74) *Attorney, Agent, or Firm* — McDonnell Boehnen Hulbert & Berghoff LLP

(57) ABSTRACT

Compositions including a CD180 binding ligand and a linked Hepatitis B antigen and their use are disclosed. The Hepatitis B antigen includes Hepatitis B virus pre-S1 and/or pre-S2 region of the HBV envelope protein (HBVpreS1/S2Ag), L-HBsAg, MHBsAg, S-HBsAg, or antigenic fragments or mutants thereof.

24 Claims, 6 Drawing Sheets
Specification includes a Sequence Listing.

(56) References Cited

OTHER PUBLICATIONS

Chi et al. (2009) Broadly neutralizing anti-HBV antibody binds to non-epitope regions of preS1. FEBS Lett. 583:3095-100.
Clark et al. (1989) Activation of human B cells. Comparison of the signal transduced by IL-4 to four different competence signals. J Immunol. 143:3873-80.
Coffman et al. (2010) Vaccine adjuvants: putting innate immunity to work. Immunity. 33:492-503.
Dion et al. (2013) Adeno-associated virus-mediated gene transfer leads to persistent hepatitis B virus replication in mice expressing HLA-A2 and HLA-DR1 molecules. J Virol. May:87(10):5554-63.
Eng et al. (2013) The potential of 1018 ISS adjuvant in hepatitis 8 vaccines: HEPLISAV™. Hum Vaccin Immunother. 9:1661-72.
Ferrari et al. (1989) The preS1 antigen of hepatitis B virus is highly immunogenic at the T cell level in man. J Clin Invest. 84:1314-9.
Gerlich WH. (2015) Prophylactic vaccination against hepatitis 8: achievements, challenges and perspectives. Med MicrobiolImmunol. 204:39-55.
Hebeis et al. (2005) Vav proteins are required forB-lymphocyte responses to LPS. Blood.106:63540.
Hebeis et al. (2004)Activation of virus-specific memory B cells in the absence of T cell help. J Exp Med. 199:593-602.
Hepatitis 8 Vaccines (2004) Releve epidemiologique hebdomadaire I Section d'hygiene du Secretariat de la Societe des Nations = Weekly epidemiological record I Health Section of the Secretariat of the League of Nations. 79:255-63.
Jilg W. (1998) Novel hepatitis 8 vaccines. Vaccine. 16 Suppi:S65-8.
Kim et al. (2009) Hepatitis 8 vaccination in HIV-infected adults: current evidence, recommendations and practical considerations. International journal of STD & AIDS.
Kim WR. (2009) Epidemiology of hepatitis B in the United States. Hepatology. 49:S28-34.
Krawczyk et al. (2014) Induction of a robust T- and B-cell immune response in non- and low-responders to conventional vaccination against hepatitis B by using a third generation PreS/S vaccine. Vaccine. 32:5077-82.
Kubba (2003) et al. Non-responders to hepatitis 8 vaccination: a review. Communicable disease and public health PHLS. 106-12.
Lavanchy D. (2004) Hepatitis 8 virus epidemiology, disease burden, treatment, and current and emerging prevention and control measures. J. Viral Hep.11:97-107.
Li W. (2015) NTCP is receptor for HBV The hepatitis 8 virus receptor. Annu Rev Cell Dev Bioi. 31:125-47.
Liang al. (2011) Predictors of relapse in chronic hepatitis B after discontinuation of anti-viral therapy. Aliment Pharmacal Ther. 34:344-52.
Loudon et al. (2010) GM-CSF increases mucosal and PA, GM-CSF increases mucosal and systemic immunogenicity fo an H1N1 influenza DNA vaccine administered into the epidermis of non-human primates. PLoS One. 5:e11021.
Luckhaupt et al. (2008) Deaths due to bloodborne infections and their sequelae among health-care workers. Am J Ind Med. 51:812-24.
Madalinski et al. (2001) Antibody responses to preS components after immunization of children with low doses of BioHepB. Vaccine. Oct. 12, 2020(1-2):92-7.
Maxon et al. (2011) The next decade of vaccines: societal and scientific challenges. Lancet. 378:348-59.
Menendez-Aria et al. (2014) Nucleoside/nucleotide analog inhibitors of hepatitis 8 virus polymerase: mechanism of action and resistance. Curr Opin Viral. 8C:1-9.
Mitchell et al. (2011) The increasing burden of imported chronic hepatitis 8—United States, 1974-2008. PLoS One. 6:e27717.

Miyake et al. (1994) Murine B cell proliferation and protection from apoptosis with an antibody against a 105-kD molecule: unresponsiveness of X-linked immunodeficient B cells. J Exp Med. 180:1217-24.
Miyake et al. (1995) RP105, a novel B cell surface molecule implicated in B cell activation, is a member of the leucine-rich repeat protein family. J Immunol. 154:3333-40.
Ni et al. (2014) Hepatitis 8 and D viruses exploit sodium taurocholate co-transporting polypeptide for species-specific entry into hepatocytes. Gastroenterology. Apr 146(4):1070-83.
Ohto et al. (2011) Crystal structures of mouse and human RP105/MD-1 complexes reveal unique dimer organization of the toll-like receptor family. J Mol Bioi. Nov. 4:413(4):815-25.
Ott et al. (2012) Global epidemiology of hepatitis 8 virus infection: new estimates of age-specific H8cAG seroprevalence and endemicity. Vaccine. 30:2212-9.
Perz et al. (2006) The contributions of hepatitis 8 virus and hepatitis C virus infections to cirrhosis and primary liver cancer worldwide. J Hepatol. 45:529-38.
Ramos H.J. (2011) RIG-I like receptors and their signaling crosstalk in the regulation of antiviral immunity. Curr Opin Virol.1:67-76.
Rendi-Wagner et al. (2006) Comparative immunogenicity of a PreS/S hepatitis 8 vaccine in non and low responders to conventional vaccine. Vaccine. 24:2871-9.
Schultz et al. (2017) The RP105/MD-1 complex: molecular signaling mechanisms and pathophysiological implications. J Leukoc Bioi. Jan:101(1):183-192.
Shimazu et al. (1999) MD-2, a molecule that confers lipopolysaccharide responsiveness on Toll-like receptor4. J Exp. Med. 189:1777-82.
Suthar et al. (2013) West Nile virus infection and immunity. Nat. Rev Microbiol. 11:115-128.
Thai et al. (2012) Convergence and coevolution of hepatitis 8 virus drug resistance. Nat Commun. 3:789.
Toita et al. (2015) Applications of human hepatitis B virus preS domain in bio- and nanotechnology. World J Gastroenterol. Jun. 28:21(24):7400-11.
Valatine et al. (1988) Antibody to a novel 95-kDa surface glycoprotein on human B cells induces calcium mobilization and B cell activation. J Immunol. 140:4071-8.
Wang et al. (2014) Immunotherapeutic interventions in chronic hepatitis 8 virus infection: a review. J Immunol Methods. May:407:1-8.
Wasley et al. (2010) The prevalence of hepatitis 8 virus infection in the United States in the era of vaccination. J Infect Dis. 202:192-201.
Weinbaum CM, (2008) Recommendations for identification and public health management of persons with chronic hepatitis 8 virus infection. Centers for Disease Control and Prevention (CDC). MMWR Recomm. Rep 57(RR-8):1-20.
The International Search Report (ISR) with Written Opinion for PCT/US2018/061218 dated Feb. 5, 2019, pp. 1-11.
Wiegand et al. (2010) Management of chronic hepatitis 8: status and challenges beyond treatment guidelines. Semin Liver Dis. 30:361-377.
Yazawa et al., (2003) CD19 regulates innate immunity by the toll-like receptor RP105 signaling in B lymphocytes. Blood. 102:1374-80.
Yoon et al. (2011) An unusual dimeric structure and assembly for TLR4 regulator RP105-MD-1. Nat Struct Mol Bioi. 2. Aug. 21:18(9):1028-35.
International Search Report for PCT/US2018/061218, dated Feb. 5, 2019.

* cited by examiner

SEQUENCE LISTING

<160> NUMBER OF SEQ ID NOS: 69

<210> SEQ ID NO 1
<211> LENGTH: 174
<212> TYPE: PRT
<213> ORGANISM: Artificial Sequence
<220> FEATURE:
<223> OTHER INFORMATION: Synthetic peptide

<400> SEQUENCE: 1

Met Gly Gly Trp Ser Ser Lys Pro Arg Gln Gly Met Gly Thr Asn Leu
1               5                   10                  15

Ser Val Pro Asn Pro Leu Gly Phe Phe Pro Asp His Gln Leu Asp Pro
                20                  25                  30

Ala Phe Gly Ala Asn Ser Asn Asn Pro Asp Trp Asp Phe Asn Pro Asn
            35                  40                  45

Lys Asp His Trp Pro Glu Ala Asn Gln Val Gly Ala Gly Ala Phe Gly
50                  55                  60

Pro Gly Phe Thr Pro Pro His Gly Gly Leu Leu Gly Trp Ser Pro Gln
65                  70                  75                  80

Ala Gln Gly Ile Leu Thr Thr Leu Pro Ala Ala Pro Pro Pro Ala Ser
                85                  90                  95

Thr Asn Arg Gln Ser Gly Arg Gln Pro Thr Pro Ile Ser Pro Pro Leu
            100                 105                 110

Arg Asp Ser His Pro Gln Ala Met Gln Trp Asn Ser Thr Thr Phe His
        115                 120                 125

Gln Ala Leu Leu Asp Pro Arg Val Arg Gly Leu Tyr Phe Pro Ala Gly
    130                 135                 140

Gly Ser Ser Ser Gly Thr Val Asn Pro Val Pro Thr Thr Ala Ser Pro
145                 150                 155                 160

Ile Ser Ser Ile Phe Ser Arg Thr Gly Asp Pro Ala Pro Asn
                165                 170

<210> SEQ ID NO 2
<211> LENGTH: 108
<212> TYPE: PRT
<213> ORGANISM: Artificial Sequence
<220> FEATURE:
<223> OTHER INFORMATION: Synthetic peptide

<400> SEQUENCE: 2

Met Gly Gly Trp Ser Ser Lys Pro Arg Gln Gly Met Gly Thr Asn Leu
1               5                   10                  15

Ser Val Pro Asn Pro Leu Gly Phe Phe Pro Asp His Gln Leu Asp Pro
                20                  25                  30

Ala Phe Gly Ala Asn Ser Asn Asn Pro Asp Trp Asp Phe Asn Pro Asn
            35                  40                  45

Lys Asp His Trp Pro Glu Ala Asn Gln Val Gly Ala Gly Ala Phe Gly
50                  55                  60

Pro Gly Phe Thr Pro Pro His Gly Gly Leu Leu Gly Trp Ser Pro Gln
65                  70                  75                  80

Ala Gln Gly Ile Leu Thr Thr Leu Pro Ala Ala Pro Pro Pro Ala Ser
                85                  90                  95

Thr Asn Arg Gln Ser Gly Arg Gln Pro Thr Pro Ile
            100                 105

<210> SEQ ID NO 3
<211> LENGTH: 66

```
<212> TYPE: PRT
<213> ORGANISM: Artificial Sequence
<220> FEATURE:
<223> OTHER INFORMATION: Synthetic peptide

<400> SEQUENCE: 3

Ser Pro Pro Leu Arg Asp Ser His Pro Gln Ala Met Gln Trp Asn Ser
1               5                   10                  15

Thr Thr Phe His Gln Ala Leu Leu Asp Pro Arg Val Arg Gly Leu Tyr
            20                  25                  30

Phe Pro Ala Gly Gly Ser Ser Gly Thr Val Asn Pro Val Pro Thr
        35                  40                  45

Thr Ala Ser Pro Ile Ser Ser Ile Phe Ser Arg Thr Gly Asp Pro Ala
    50                  55                  60

Pro Asn
65

<210> SEQ ID NO 4
<211> LENGTH: 400
<212> TYPE: PRT
<213> ORGANISM: Artificial Sequence
<220> FEATURE:
<223> OTHER INFORMATION: Synthetic peptide

<400> SEQUENCE: 4

Met Gly Gly Trp Ser Ser Lys Pro Arg Gln Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Asn
        35                  40                  45

Lys Asp His Trp Pro Glu Ala Asn Gln Val Gly Ala Gly Ala Phe Gly
    50                  55                  60

Pro Gly Phe Thr Pro Pro His Gly Gly Leu Leu Gly Trp Ser Pro Gln
65                  70                  75                  80

Ala Gln Gly Ile Leu Thr Thr Leu Pro Ala Ala Pro Pro Pro Ala Ser
                85                  90                  95

Thr Asn Arg Gln Ser Gly Arg Gln Pro Thr Pro Ile Ser Pro Pro Leu
            100                 105                 110

Arg Asp Ser His Pro Gln Ala Met Gln Trp Asn Ser Thr Thr Phe His
        115                 120                 125

Gln Ala Leu Leu Asp Pro Arg Val Arg Gly Leu Tyr Phe Pro Ala Gly
    130                 135                 140

Gly Ser Ser Ser Gly Thr Val Asn Pro Val Pro Thr Thr Ala Ser Pro
145                 150                 155                 160

Ile Ser Ser Ile Phe Ser Arg Thr Gly Asp Pro Ala Pro Asn Met Glu
                165                 170                 175

Ser Thr Thr Ser Gly Phe Leu Gly Pro Leu Leu Val Leu Gln Ala Gly
            180                 185                 190

Phe Phe Leu Leu Thr Arg Ile Leu Thr Ile Pro Gln Ser Leu Asp Ser
        195                 200                 205

Trp Trp Thr Ser Leu Asn Phe Leu Gly Gly Ala Pro Thr Cys Pro Gly
    210                 215                 220

Gln Asn Ser Gln Ser Pro Thr Ser Asn His Ser Pro Thr Ser Cys Pro
225                 230                 235                 240

Pro Thr Cys Pro Gly Tyr Arg Trp Met Cys Leu Arg Arg Phe Ile Ile
                245                 250                 255
```

```
Phe Leu Phe Ile Leu Leu Cys Leu Ile Phe Leu Val Leu Leu
            260                 265                 270

Asp Tyr Gln Gly Met Leu Pro Val Cys Pro Leu Leu Pro Gly Thr Ser
                275                 280                 285

Thr Thr Ser Thr Gly Pro Cys Arg Thr Cys Thr Ile Pro Ala Gln Gly
290                 295                 300

Thr Ser Met Phe Pro Ser Cys Cys Thr Lys Pro Ser Asp Gly Asn
305                 310                 315                 320

Cys Thr Cys Ile Pro Ile Pro Ser Ser Trp Ala Phe Ala Arg Phe Leu
                325                 330                 335

Trp Glu Trp Ala Ser Val Arg Phe Ser Trp Leu Ser Leu Val Pro
                340                 345                 350

Phe Val Gln Trp Phe Val Gly Leu Ser Pro Thr Val Trp Leu Ser Ala
                355                 360                 365

Ile Trp Met Met Trp Tyr Trp Gly Pro Ser Leu Tyr Asn Ile Leu Ser
                370                 375                 380

Pro Phe Leu Pro Leu Leu Pro Ile Phe Phe Cys Leu Trp Val Tyr Ile
385                 390                 395                 400

<210> SEQ ID NO 5
<211> LENGTH: 291
<212> TYPE: PRT
<213> ORGANISM: Artificial Sequence
<220> FEATURE:
<223> OTHER INFORMATION: Synthetic peptide

<400> SEQUENCE: 5

Pro Pro Leu Arg Asp Ser His Pro Gln Ala Met Gln Trp Asn Ser Thr
1               5                   10                  15

Thr Phe His Gln Ala Leu Leu Asp Pro Arg Val Arg Gly Leu Tyr Phe
                20                  25                  30

Pro Ala Gly Gly Ser Ser Ser Gly Thr Val Asn Pro Val Pro Thr Thr
            35                  40                  45

Ala Ser Pro Ile Ser Ser Ile Phe Ser Arg Thr Gly Asp Pro Ala Pro
50                  55                  60

Asn Met Glu Ser Thr Thr Ser Gly Phe Leu Gly Pro Leu Leu Val Leu
65                  70                  75                  80

Gln Ala Gly Phe Phe Leu Leu Thr Arg Ile Leu Thr Ile Pro Gln Ser
                85                  90                  95

Leu Asp Ser Trp Trp Thr Ser Leu Asn Phe Leu Gly Gly Ala Pro Thr
            100                 105                 110

Cys Pro Gly Gln Asn Ser Gln Ser Pro Thr Ser Asn His Ser Pro Thr
        115                 120                 125

Ser Cys Pro Pro Thr Cys Pro Gly Tyr Arg Trp Met Cys Leu Arg Arg
    130                 135                 140

Phe Ile Ile Phe Leu Phe Ile Leu Leu Leu Cys Leu Ile Phe Leu Leu
145                 150                 155                 160

Val Leu Leu Asp Tyr Gln Gly Met Leu Pro Val Cys Pro Leu Leu Pro
                165                 170                 175

Gly Thr Ser Thr Thr Ser Thr Gly Pro Cys Arg Thr Cys Thr Ile Pro
            180                 185                 190

Ala Gln Gly Thr Ser Met Phe Pro Ser Cys Cys Thr Lys Pro Ser
        195                 200                 205

Asp Gly Asn Cys Thr Cys Ile Pro Ile Pro Ser Ser Trp Ala Phe Ala
210                 215                 220
```

```
Arg Phe Leu Trp Glu Trp Ala Ser Val Arg Phe Ser Trp Leu Ser Leu
225                 230                 235                 240

Leu Val Pro Phe Val Gln Trp Phe Val Gly Leu Ser Pro Thr Val Trp
                245                 250                 255

Leu Ser Ala Ile Trp Met Met Trp Tyr Trp Gly Pro Ser Leu Tyr Asn
            260                 265                 270

Ile Leu Ser Pro Phe Leu Pro Leu Pro Ile Phe Phe Cys Leu Trp
        275                 280                 285

Val Tyr Ile
    290

<210> SEQ ID NO 6
<211> LENGTH: 226
<212> TYPE: PRT
<213> ORGANISM: Artificial Sequence
<220> FEATURE:
<223> OTHER INFORMATION: Synthetic peptide

<400> SEQUENCE: 6

Met Glu Ser Thr Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Ala Pro Thr Cys
        35                  40                  45

Pro Gly Gln Asn Ser Gln Ser Pro Thr Ser Asn His Ser Pro Thr Ser
    50                  55                  60

Cys Pro Pro Thr Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Leu Pro Gly
            100                 105                 110

Thr Ser Thr Thr Ser Thr Gly Pro Cys Arg Thr Cys Thr Ile Pro Ala
        115                 120                 125

Gln Gly Thr Ser Met Phe Pro Ser Cys Cys Cys Thr Lys Pro Ser Asp
    130                 135                 140

Gly Asn Cys Thr Cys Ile Pro Ile Pro Ser Ser Trp Ala Phe Ala Arg
145                 150                 155                 160

Phe Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Ala Ile Trp Met Met Trp Tyr Trp Gly Pro Ser Leu Tyr Asn Ile
        195                 200                 205

Leu Ser Pro Phe Leu Pro Leu Leu Pro Ile Phe Phe Cys Leu Trp Val
    210                 215                 220

Tyr Ile
225

<210> SEQ ID NO 7
<211> LENGTH: 108
<212> TYPE: PRT
<213> ORGANISM: Artificial Sequence
<220> FEATURE:
<223> OTHER INFORMATION: Synthetic peptide
```

```
<400> SEQUENCE: 7

Met Gly Gly Trp Ser Ala Lys Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Asn
        35                  40                  45

Lys Asp His Trp Pro Glu Ala Asn Gln Val Gly Val Gly Ala Phe Gly
50                  55                  60

Pro Gly Phe Thr Pro Pro His Gly Gly Leu Leu Gly Trp Ser Ser Gln
65                  70                  75                  80

Ala Gln Gly Thr Leu His Thr Val Pro Ala Val Pro Pro Pro Ala Ser
                85                  90                  95

Thr Asn Arg Gln Thr Gly Arg Gln Pro Thr Pro Ile
            100                 105

<210> SEQ ID NO 8
<211> LENGTH: 55
<212> TYPE: PRT
<213> ORGANISM: Artificial Sequence
<220> FEATURE:
<223> OTHER INFORMATION: Synthetic peptide

<400> SEQUENCE: 8

Ser Pro Pro Leu Arg Asp Ser His Pro Gln Ala Met Gln Trp Asn Ser
1               5                   10                  15

Thr Ala Phe Gln Gln Ala Leu Gln Asp Pro Arg Val Arg Gly Leu Phe
            20                  25                  30

Phe Pro Ala Gly Gly Ser Ser Gly Thr Val Asn Pro Ala Pro Asn
        35                  40                  45

Ile Ala Ser His Ile Ser Ser
        50                  55

<210> SEQ ID NO 9
<211> LENGTH: 236
<212> TYPE: PRT
<213> ORGANISM: Artificial Sequence
<220> FEATURE:
<223> OTHER INFORMATION: Synthetic peptide

<400> SEQUENCE: 9

Ile Ser Ser Arg Thr Gly Asp Pro Ala Leu Asn Met Glu Asn Ile Thr
1               5                   10                  15

Ser Gly Phe Leu Gly Pro Leu Leu Val Leu Gln Ala Gly Phe Phe Leu
            20                  25                  30

Leu Thr Arg Ile Leu Thr Ile Pro Gln Ser Leu Asp Ser Trp Trp Thr
            35                  40                  45

Ser Leu Asn Phe Leu Gly Gly Ser Pro Val Cys Leu Gly Gln Asn Ser
50                  55                  60

Gln Ser Pro Thr Ser Asn His Ser Pro Thr Ser Cys Pro Pro Ile Cys
65                  70                  75                  80

Pro Gly Tyr Arg Trp Met Cys Leu Arg Arg Phe Ile Ile Phe Leu Phe
                85                  90                  95

Ile Leu Leu Leu Cys Leu Ile Phe Leu Leu Val Leu Leu Asp Tyr Gln
            100                 105                 110

Gly Met Leu Pro Val Cys Pro Leu Ile Pro Gly Ser Thr Thr Thr Ser
            115                 120                 125
```

```
Thr Gly Pro Cys Lys Thr Cys Thr Thr Pro Ala Gln Gly Asn Ser Met
            130                 135                 140
Phe Pro Cys Cys Thr Lys Pro Thr Asp Gly Asn Cys Thr Cys Ile
145                 150                 155                 160
Pro Ile Pro Ser Ser Trp Ala Phe Ala Lys Tyr Leu Trp Glu Trp Ala
                165                 170                 175
Ser Val Arg Phe Ser Trp Leu Ser Leu Leu Val Pro Phe Val Gln Trp
            180                 185                 190
Phe Val Gly Leu Ser Pro Thr Val Trp Leu Ser Val Ile Trp Met Met
            195                 200                 205
Trp Tyr Trp Gly Pro Ser Leu Tyr Asn Ile Leu Ser Pro Phe Ile Pro
210                 215                 220
Leu Leu Pro Ile Phe Phe Cys Leu Trp Val Tyr Ile
225                 230                 235
```

<210> SEQ ID NO 10
<211> LENGTH: 291
<212> TYPE: PRT
<213> ORGANISM: Artificial Sequence
<220> FEATURE:
<223> OTHER INFORMATION: Synthetic peptide

<400> SEQUENCE: 10

```
Ser Pro Pro Leu Arg Asp Ser His Pro Gln Ala Met Gln Trp Asn Ser
1               5                   10                  15
Thr Ala Phe Gln Gln Ala Leu Gln Asp Pro Arg Val Arg Gly Leu Phe
                20                  25                  30
Phe Pro Ala Gly Gly Ser Ser Ser Gly Thr Val Asn Pro Ala Pro Asn
            35                  40                  45
Ile Ala Ser His Ile Ser Ser Ile Ser Ser Arg Thr Gly Asp Pro Ala
        50                  55                  60
Leu Asn Met Glu Asn Ile Thr Ser Gly Phe Leu Gly Pro Leu Leu Val
65                  70                  75                  80
Leu Gln Ala Gly Phe Phe Leu Leu Thr Arg Ile Leu Thr Ile Pro Gln
                85                  90                  95
Ser Leu Asp Ser Trp Trp Thr Ser Leu Asn Phe Leu Gly Gly Ser Pro
            100                 105                 110
Val Cys Leu Gly Gln Asn Ser Gln Ser Pro Thr Ser Asn His Ser Pro
        115                 120                 125
Thr Ser Cys Pro Pro Ile Cys Pro Gly Tyr Arg Trp Met Cys Leu Arg
130                 135                 140
Arg Phe Ile Ile Phe Leu Phe Ile Leu Leu Leu Cys Leu Ile Phe Leu
145                 150                 155                 160
Leu Val Leu Leu Asp Tyr Gln Gly Met Leu Pro Val Cys Pro Leu Ile
                165                 170                 175
Pro Gly Ser Thr Thr Thr Ser Thr Gly Pro Cys Lys Thr Cys Thr Thr
            180                 185                 190
Pro Ala Gln Gly Asn Ser Met Phe Pro Cys Cys Cys Thr Lys Pro Thr
        195                 200                 205
Asp Gly Asn Cys Thr Cys Ile Pro Ile Pro Ser Ser Trp Ala Phe Ala
210                 215                 220
Lys Tyr Leu Trp Glu Trp Ala Ser Val Arg Phe Ser Trp Leu Ser Leu
225                 230                 235                 240
Leu Val Pro Phe Val Gln Trp Phe Val Gly Leu Ser Pro Thr Val Trp
                245                 250                 255
```

```
Leu Ser Val Ile Trp Met Met Trp Tyr Trp Gly Pro Ser Leu Tyr Asn
            260             265                 270

Ile Leu Ser Pro Phe Ile Pro Leu Leu Pro Ile Phe Phe Cys Leu Trp
        275             280                 285

Val Tyr Ile
    290

<210> SEQ ID NO 11
<211> LENGTH: 400
<212> TYPE: PRT
<213> ORGANISM: Artificial Sequence
<220> FEATURE:
<223> OTHER INFORMATION: Synthetic peptide

<400> SEQUENCE: 11

Met Gly Gly Trp Ser Ala Lys Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Asn
        35                  40                  45

Lys Asp His Trp Pro Glu Ala Asn Gln Val Gly Val Gly Ala Phe Gly
    50                  55                  60

Pro Gly Phe Thr Pro Pro His Gly Gly Leu Leu Gly Trp Ser Gln
65                  70                  75                  80

Ala Gln Gly Thr Leu His Thr Val Pro Ala Val Pro Pro Ala Ser
                85                  90                  95

Thr Asn Arg Gln Thr Gly Arg Gln Pro Thr Pro Ile Ser Pro Pro Leu
            100                 105                 110

Arg Asp Ser His Pro Gln Ala Met Gln Trp Asn Ser Thr Ala Phe Gln
        115                 120                 125

Gln Ala Leu Gln Asp Pro Arg Val Arg Gly Leu Phe Phe Pro Ala Gly
    130                 135                 140

Gly Ser Ser Ser Gly Thr Val Asn Pro Ala Pro Asn Ile Ala Ser His
145                 150                 155                 160

Ile Ser Ser Ile Ser Ser Arg Thr Gly Asp Pro Ala Leu Asn Met Glu
                165                 170                 175

Asn Ile Thr Ser Gly Phe Leu Gly Pro Leu Leu Val Leu Gln Ala Gly
            180                 185                 190

Phe Phe Leu Leu Thr Arg Ile Leu Thr Ile Pro Gln Ser Leu Asp Ser
        195                 200                 205

Trp Trp Thr Ser Leu Asn Phe Leu Gly Gly Ser Pro Val Cys Leu Gly
    210                 215                 220

Gln Asn Ser Gln Ser Pro Thr Ser Asn His Ser Pro Thr Ser Cys Pro
225                 230                 235                 240

Pro Ile Cys Pro Gly Tyr Arg Trp Met Cys Leu Arg Arg Phe Ile Ile
                245                 250                 255

Phe Leu Phe Ile Leu Leu Leu Cys Leu Ile Phe Leu Leu Val Leu Leu
            260                 265                 270

Asp Tyr Gln Gly Met Leu Pro Val Cys Pro Leu Ile Pro Gly Ser Thr
        275                 280                 285

Thr Thr Ser Thr Gly Pro Cys Lys Thr Cys Thr Thr Pro Ala Gln Gly
    290                 295                 300

Asn Ser Met Phe Pro Ser Cys Cys Cys Thr Lys Pro Thr Asp Gly Asn
305                 310                 315                 320
```

Cys Thr Cys Ile Pro Ile Pro Ser Ser Trp Ala Phe Ala Lys Tyr Leu
            325                 330                 335

Trp Glu Trp Ala Ser Val Arg Phe Ser Trp Leu Ser Leu Leu Val Pro
            340                 345                 350

Phe Val Gln Trp Phe Val Gly Leu Ser Pro Thr Val Trp Leu Ser Val
            355                 360                 365

Ile Trp Met Met Trp Tyr Trp Gly Pro Ser Leu Tyr Asn Ile Leu Ser
            370                 375                 380

Pro Phe Ile Pro Leu Leu Pro Ile Phe Phe Cys Leu Trp Val Tyr Ile
385                 390                 395                 400

<210> SEQ ID NO 12
<211> LENGTH: 108
<212> TYPE: PRT
<213> ORGANISM: Artificial Sequence
<220> FEATURE:
<223> OTHER INFORMATION: Synthetic peptide

<400> SEQUENCE: 12

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Val
        35                  40                  45

Lys Asp Asp Trp Pro Ala Ala Asn Gln Val Gly Val Gly Ala Phe Gly
    50                  55                  60

Pro Arg Leu Thr Pro Pro His Gly Gly Ile Leu Gly Trp Ser Pro Gln
65                  70                  75                  80

Ala Gln Gly Ile Leu Thr Thr Val Ser Thr Ile Pro Pro Pro Ala Ser
            85                  90                  95

Thr Asn Arg Gln Ser Gly Arg Gln Pro Thr Pro Ile
            100                 105

<210> SEQ ID NO 13
<211> LENGTH: 55
<212> TYPE: PRT
<213> ORGANISM: Artificial Sequence
<220> FEATURE:
<223> OTHER INFORMATION: Synthetic peptide

<400> SEQUENCE: 13

Ser Pro Pro Leu Arg Asp Ser His Pro Gln Ala Met Gln Trp Asn Ser
1               5                   10                  15

Thr Ala Phe His Gln Thr Leu Gln Asp Pro Arg Val Arg Gly Leu Tyr
            20                  25                  30

Leu Pro Ala Gly Gly Ser Ser Gly Thr Val Asn Pro Ala Pro Asn
        35                  40                  45

Ile Ala Ser His Ile Ser Ser
    50                  55

<210> SEQ ID NO 14
<211> LENGTH: 237
<212> TYPE: PRT
<213> ORGANISM: Artificial Sequence
<220> FEATURE:
<223> OTHER INFORMATION: Synthetic peptide

<400> SEQUENCE: 14

Ile Ser Ala Arg Thr Gly Asp Pro Val Thr Asn Met Glu Asn Ile Thr

```
1               5                   10                  15
Ser Gly Phe Leu Gly Pro Leu Leu Val Leu Gln Ala Gly Phe Phe Leu
            20                  25                  30

Leu Thr Arg Ile Leu Thr Ile Pro Gln Ser Leu Asp Ser Trp Trp Thr
            35                  40                  45

Ser Leu Asn Phe Leu Gly Gly Ser Pro Val Cys Leu Gly Gln Asn Ser
50                      55                  60

Gln Ser Pro Thr Ser Asn His Ser Pro Thr Ser Cys Pro Pro Ile Cys
65                  70                  75                  80

Pro Gly Tyr Arg Trp Met Cys Leu Arg Arg Phe Ile Ile Phe Leu Phe
                85                  90                  95

Ile Leu Leu Leu Cys Leu Ile Phe Leu Leu Val Leu Leu Asp Tyr Gln
            100                 105                 110

Gly Met Leu Pro Val Cys Pro Leu Ile Pro Gly Ser Thr Thr Thr Ser
            115                 120                 125

Thr Gly Pro Cys Lys Thr Cys Thr Thr Pro Ala Gln Gly Asn Ser Met
130                 135                 140

Phe Pro Ser Cys Cys Cys Thr Lys Pro Thr Asp Gly Asn Cys Thr Cys
145                 150                 155                 160

Ile Pro Ile Pro Ser Ser Trp Ala Phe Ala Lys Tyr Leu Trp Glu Trp
                165                 170                 175

Ala Ser Val Arg Phe Ser Trp Leu Ser Leu Leu Val Pro Phe Val Gln
            180                 185                 190

Trp Phe Val Gly Leu Ser Pro Thr Val Trp Leu Ser Ala Ile Trp Met
            195                 200                 205

Met Trp Tyr Trp Gly Pro Ser Leu Tyr Ser Ile Val Ser Pro Phe Ile
210                 215                 220

Pro Leu Leu Pro Ile Phe Phe Cys Leu Trp Val Tyr Ile
225                 230                 235

<210> SEQ ID NO 15
<211> LENGTH: 292
<212> TYPE: PRT
<213> ORGANISM: Artificial Sequence
<220> FEATURE:
<223> OTHER INFORMATION: Synthetic peptide

<400> SEQUENCE: 15

Ser Pro Pro Leu Arg Asp Ser His Pro Gln Ala Met Gln Trp Asn Ser
1               5                   10                  15

Thr Ala Phe His Gln Thr Leu Gln Asp Pro Arg Val Arg Gly Leu Tyr
            20                  25                  30

Leu Pro Ala Gly Gly Ser Ser Gly Thr Val Asn Pro Ala Pro Asn
            35                  40                  45

Ile Ala Ser His Ile Ser Ser Ile Ser Ala Arg Thr Gly Asp Pro Val
50                  55                  60

Thr Asn Met Glu Asn Ile Thr Ser Gly Phe Leu Gly Pro Leu Leu Val
65                  70                  75                  80

Leu Gln Ala Gly Phe Phe Leu Leu Thr Arg Ile Leu Thr Ile Pro Gln
                85                  90                  95

Ser Leu Asp Ser Trp Trp Thr Ser Leu Asn Phe Leu Gly Gly Ser Pro
            100                 105                 110

Val Cys Leu Gly Gln Asn Ser Gln Ser Pro Thr Ser Asn His Ser Pro
            115                 120                 125

Thr Ser Cys Pro Pro Ile Cys Pro Gly Tyr Arg Trp Met Cys Leu Arg
```

```
                130                 135                 140
Arg Phe Ile Ile Phe Leu Phe Ile Leu Leu Cys Leu Ile Phe Leu
145                 150                 155                 160

Leu Val Leu Leu Asp Tyr Gln Gly Met Leu Pro Val Cys Pro Leu Ile
                165                 170                 175

Pro Gly Ser Thr Thr Thr Ser Thr Gly Pro Cys Lys Thr Cys Thr Thr
                180                 185                 190

Pro Ala Gln Gly Asn Ser Met Phe Pro Ser Cys Cys Cys Thr Lys Pro
                195                 200                 205

Thr Asp Gly Asn Cys Thr Cys Ile Pro Ile Pro Ser Ser Trp Ala Phe
                210                 215                 220

Ala Lys Tyr Leu Trp Glu Trp Ala Ser Val Arg Phe Ser Trp Leu Ser
225                 230                 235                 240

Leu Leu Val Pro Phe Val Gln Trp Phe Val Gly Leu Ser Pro Thr Val
                245                 250                 255

Trp Leu Ser Ala Ile Trp Met Met Trp Tyr Trp Gly Pro Ser Leu Tyr
                260                 265                 270

Ser Ile Val Ser Pro Phe Ile Pro Leu Leu Pro Ile Phe Phe Cys Leu
                275                 280                 285

Trp Val Tyr Ile
    290

<210> SEQ ID NO 16
<211> LENGTH: 400
<212> TYPE: PRT
<213> ORGANISM: Artificial Sequence
<220> FEATURE:
<223> OTHER INFORMATION: Synthetic peptide

<400> SEQUENCE: 16

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
                20                  25                  30

Ala Phe Gly Ala Asn Ser Asn Asn Pro Asp Trp Asp Phe Asn Pro Val
                35                  40                  45

Lys Asp Asp Trp Pro Ala Ala Asn Gln Val Gly Val Gly Ala Phe Gly
            50                  55                  60

Pro Arg Leu Thr Pro Pro His Gly Gly Ile Leu Gly Trp Ser Pro Gln
65                  70                  75                  80

Ala Gln Gly Ile Leu Thr Thr Val Ser Thr Ile Pro Pro Pro Ala Ser
                85                  90                  95

Thr Asn Arg Gln Ser Gly Arg Gln Pro Thr Pro Ile Ser Pro Pro Leu
                100                 105                 110

Arg Asp Ser His Pro Gln Ala Met Gln Trp Asn Ser Thr Ala Phe His
                115                 120                 125

Gln Thr Leu Gln Asp Pro Arg Val Arg Gly Leu Tyr Leu Pro Ala Gly
                130                 135                 140

Gly Ser Ser Ser Gly Thr Val Asn Pro Ala Pro Asn Ile Ala Ser His
145                 150                 155                 160

Ile Ser Ser Ile Ser Ala Arg Thr Gly Asp Pro Val Thr Asn Met Glu
                165                 170                 175

Asn Ile Thr Ser Gly Phe Leu Gly Pro Leu Leu Val Leu Gln Ala Gly
                180                 185                 190

Phe Phe Leu Leu Thr Arg Ile Leu Thr Ile Pro Gln Ser Leu Asp Ser
```

```
                195                 200                 205
Trp Trp Thr Ser Leu Asn Phe Leu Gly Gly Ser Pro Val Cys Leu Gly
    210                 215                 220

Gln Asn Ser Gln Ser Pro Thr Ser Asn His Ser Pro Thr Ser Cys Pro
225                 230                 235                 240

Pro Ile Cys Pro Gly Tyr Arg Trp Met Cys Leu Arg Arg Phe Ile Ile
                245                 250                 255

Phe Leu Phe Ile Leu Leu Leu Cys Leu Ile Phe Leu Leu Val Leu Leu
            260                 265                 270

Asp Tyr Gln Gly Met Leu Pro Val Cys Pro Leu Ile Pro Gly Ser Thr
        275                 280                 285

Thr Thr Ser Thr Gly Pro Cys Lys Thr Cys Thr Thr Pro Ala Gln Gly
290                 295                 300

Asn Ser Met Phe Pro Ser Cys Cys Cys Thr Lys Pro Thr Asp Gly Asn
305                 310                 315                 320

Cys Thr Cys Ile Pro Ile Pro Ser Ser Trp Ala Phe Ala Lys Tyr Leu
                325                 330                 335

Trp Glu Trp Ala Ser Val Arg Phe Ser Trp Leu Ser Leu Leu Val Pro
            340                 345                 350

Phe Val Gln Trp Phe Val Gly Leu Ser Pro Thr Val Trp Leu Ser Ala
        355                 360                 365

Ile Trp Met Met Trp Tyr Trp Gly Pro Ser Leu Tyr Ser Ile Val Ser
370                 375                 380

Pro Phe Ile Pro Leu Leu Pro Ile Phe Phe Cys Leu Trp Val Tyr Ile
385                 390                 395                 400

<210> SEQ ID NO 17
<211> LENGTH: 108
<212> TYPE: PRT
<213> ORGANISM: Artificial Sequence
<220> FEATURE:
<223> OTHER INFORMATION: Synthetic peptide

<400> SEQUENCE: 17

Met Gly Gly Arg Leu Pro Lys Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Ile
        35                  40                  45

Lys Asp His Trp Pro Gln Ala Asn Gln Val Gly Val Gly Ala Phe Gly
    50                  55                  60

Pro Gly Phe Thr Pro Pro His Gly Gly Val Leu Gly Trp Ser Pro Gln
65                  70                  75                  80

Ala Gln Gly Thr Leu Thr Thr Val Pro Ala Val Pro Pro Pro Ala Ser
                85                  90                  95

Thr Asn Arg Gln Ser Gly Arg Gln Pro Thr Pro Ile
            100                 105

<210> SEQ ID NO 18
<211> LENGTH: 55
<212> TYPE: PRT
<213> ORGANISM: Artificial Sequence
<220> FEATURE:
<223> OTHER INFORMATION: Synthetic peptide

<400> SEQUENCE: 18
```

```
Ser Pro Pro Leu Arg Asp Ser His Pro Gln Ala Met Gln Trp Asn Ser
1               5                   10                  15

Thr Lys Phe His Gln Thr Leu Gln Asp Pro Arg Val Arg Gly Leu Tyr
            20                  25                  30

Phe Pro Ala Gly Gly Ser Ser Gly Thr Val Asn Pro Ala Pro Asn
        35                  40                  45

Ile Ala Ser His Ile Ser Ser
50                  55
```

<210> SEQ ID NO 19
<211> LENGTH: 237
<212> TYPE: PRT
<213> ORGANISM: Artificial Sequence
<220> FEATURE:
<223> OTHER INFORMATION: Synthetic peptide

<400> SEQUENCE: 19

```
Ile Ser Ser Arg Ile Gly Asp Pro Ala Pro Thr Met Glu Asn Ile Thr
1               5                   10                  15

Ser Gly Phe Leu Gly Pro Leu Leu Val Leu Gln Ala Gly Phe Phe Leu
            20                  25                  30

Leu Thr Arg Ile Leu Thr Ile Pro Gln Ser Leu Asp Ser Trp Trp Thr
            35                  40                  45

Ser Leu Asn Phe Leu Gly Glu Ala Pro Val Cys Leu Gly Gln Asn Ser
50                  55                  60

Gln Ser Pro Thr Ser Asn His Ser Pro Thr Ser Cys Pro Pro Ile Cys
65                  70                  75                  80

Pro Gly Tyr Arg Trp Met Cys Leu Arg Arg Phe Ile Ile Phe Leu Phe
                85                  90                  95

Ile Leu Leu Leu Cys Leu Ile Phe Leu Leu Val Leu Leu Asp Cys Gln
            100                 105                 110

Gly Met Leu Pro Val Cys Pro Leu Ile Pro Gly Ser Thr Thr Thr Ser
            115                 120                 125

Thr Gly Pro Cys Arg Thr Cys Thr Thr Pro Ala Gln Gly Asn Ser Met
130                 135                 140

Phe Pro Ser Cys Cys Cys Thr Lys Pro Thr Asp Gly Asn Cys Thr Cys
145                 150                 155                 160

Ile Pro Ile Pro Ser Ser Trp Ala Phe Ala Lys Tyr Leu Trp Glu Trp
                165                 170                 175

Ala Ser Val Arg Phe Ser Trp Leu Ser Leu Leu Val Pro Phe Val Gln
            180                 185                 190

Trp Phe Val Gly Leu Ser Pro Thr Val Trp Leu Ser Val Ile Trp Met
            195                 200                 205

Met Trp Tyr Trp Gly Pro Ser Leu Tyr Asn Ile Leu Ser Pro Phe Ile
210                 215                 220

Pro Leu Leu Pro Ile Phe Phe Cys Leu Trp Val Tyr Ile
225                 230                 235
```

<210> SEQ ID NO 20
<211> LENGTH: 292
<212> TYPE: PRT
<213> ORGANISM: Artificial Sequence
<220> FEATURE:
<223> OTHER INFORMATION: Synthetic peptide

<400> SEQUENCE: 20

```
Ser Pro Pro Leu Arg Asp Ser His Pro Gln Ala Met Gln Trp Asn Ser
1               5                   10                  15
```

```
Thr Lys Phe His Gln Thr Leu Gln Asp Pro Arg Val Arg Gly Leu Tyr
         20                  25                  30

Phe Pro Ala Gly Gly Ser Ser Gly Thr Val Asn Pro Ala Pro Asn
         35                  40                  45

Ile Ala Ser His Ile Ser Ser Ile Ser Ser Arg Ile Gly Asp Pro Ala
 50                  55                  60

Pro Thr Met Glu Asn Ile Thr Ser Gly Phe Leu Gly Pro Leu Leu Val
 65                  70                  75                  80

Leu Gln Ala Gly Phe Phe Leu Leu Thr Arg Ile Leu Thr Ile Pro Gln
                 85                  90                  95

Ser Leu Asp Ser Trp Trp Thr Ser Leu Asn Phe Leu Gly Glu Ala Pro
                100                 105                 110

Val Cys Leu Gly Gln Asn Ser Gln Ser Pro Thr Ser Asn His Ser Pro
                115                 120                 125

Thr Ser Cys Pro Pro Ile Cys Pro Gly Tyr Arg Trp Met Cys Leu Arg
         130                 135                 140

Arg Phe Ile Ile Phe Leu Phe Ile Leu Leu Leu Cys Leu Ile Phe Leu
145                 150                 155                 160

Leu Val Leu Leu Asp Cys Gln Gly Met Leu Pro Val Cys Pro Leu Ile
                165                 170                 175

Pro Gly Ser Thr Thr Thr Ser Thr Gly Pro Cys Arg Thr Cys Thr Thr
                180                 185                 190

Pro Ala Gln Gly Asn Ser Met Phe Pro Ser Cys Cys Cys Thr Lys Pro
         195                 200                 205

Thr Asp Gly Asn Cys Thr Cys Ile Pro Ile Pro Ser Ser Trp Ala Phe
 210                 215                 220

Ala Lys Tyr Leu Trp Glu Trp Ala Ser Val Arg Phe Ser Trp Leu Ser
225                 230                 235                 240

Leu Leu Val Pro Phe Val Gln Trp Phe Val Gly Leu Ser Pro Thr Val
                245                 250                 255

Trp Leu Ser Val Ile Trp Met Met Trp Tyr Trp Gly Pro Ser Leu Tyr
                260                 265                 270

Asn Ile Leu Ser Pro Phe Ile Pro Leu Leu Pro Ile Phe Phe Cys Leu
                275                 280                 285

Trp Val Tyr Ile
        290

<210> SEQ ID NO 21
<211> LENGTH: 400
<212> TYPE: PRT
<213> ORGANISM: Artificial Sequence
<220> FEATURE:
<223> OTHER INFORMATION: Synthetic peptide

<400> SEQUENCE: 21

Met Gly Gly Arg Leu Pro Lys Pro Arg Lys Gly Met Gly Thr Asn Leu
 1               5                  10                  15

Ser Val Pro Asn Pro Leu Gly Phe Phe Pro Asp His Gln Leu Asp Pro
                 20                  25                  30

Ala Phe Gly Ala Asn Ser Asn Asn Pro Asp Trp Asp Phe Asn Pro Ile
         35                  40                  45

Lys Asp His Trp Pro Gln Ala Asn Gln Val Gly Val Gly Ala Phe Gly
 50                  55                  60

Pro Gly Phe Thr Pro Pro His Gly Gly Val Leu Gly Trp Ser Pro Gln
 65                  70                  75                  80
```

Ala Gln Gly Thr Leu Thr Thr Val Pro Ala Val Pro Pro Ala Ser
            85                  90                  95

Thr Asn Arg Gln Ser Gly Arg Gln Pro Thr Pro Ile Ser Pro Pro Leu
        100                 105                 110

Arg Asp Ser His Pro Gln Ala Met Gln Trp Asn Ser Thr Lys Phe His
        115                 120                 125

Gln Thr Leu Gln Asp Pro Arg Val Arg Gly Leu Tyr Phe Pro Ala Gly
    130                 135                 140

Gly Ser Ser Ser Gly Thr Val Asn Pro Ala Pro Asn Ile Ala Ser His
145                 150                 155                 160

Ile Ser Ser Ile Ser Ser Arg Ile Gly Asp Pro Ala Pro Thr Met Glu
                165                 170                 175

Asn Ile Thr Ser Gly Phe Leu Gly Pro Leu Leu Val Leu Gln Ala Gly
                180                 185                 190

Phe Phe Leu Leu Thr Arg Ile Leu Thr Ile Pro Gln Ser Leu Asp Ser
            195                 200                 205

Trp Trp Thr Ser Leu Asn Phe Leu Gly Glu Ala Pro Val Cys Leu Gly
    210                 215                 220

Gln Asn Ser Gln Ser Pro Thr Ser Asn His Ser Pro Thr Ser Cys Pro
225                 230                 235                 240

Pro Ile Cys Pro Gly Tyr Arg Trp Met Cys Leu Arg Arg Phe Ile Ile
                245                 250                 255

Phe Leu Phe Ile Leu Leu Leu Cys Leu Ile Phe Leu Leu Val Leu Leu
            260                 265                 270

Asp Cys Gln Gly Met Leu Pro Val Cys Pro Leu Ile Pro Gly Ser Thr
        275                 280                 285

Thr Thr Ser Thr Gly Pro Cys Arg Thr Cys Thr Thr Pro Ala Gln Gly
    290                 295                 300

Asn Ser Met Phe Pro Ser Cys Cys Cys Thr Lys Pro Thr Asp Gly Asn
305                 310                 315                 320

Cys Thr Cys Ile Pro Ile Pro Ser Ser Trp Ala Phe Ala Lys Tyr Leu
                325                 330                 335

Trp Glu Trp Ala Ser Val Arg Phe Ser Trp Leu Ser Leu Leu Val Pro
            340                 345                 350

Phe Val Gln Trp Phe Val Gly Leu Ser Pro Thr Val Trp Leu Ser Val
        355                 360                 365

Ile Trp Met Met Trp Tyr Trp Gly Pro Ser Leu Tyr Asn Ile Leu Ser
    370                 375                 380

Pro Phe Ile Pro Leu Leu Pro Ile Phe Phe Cys Leu Trp Val Tyr Ile
385                 390                 395                 400

<210> SEQ ID NO 22
<211> LENGTH: 108
<212> TYPE: PRT
<213> ORGANISM: Artificial Sequence
<220> FEATURE:
<223> OTHER INFORMATION: Synthetic peptide

<400> SEQUENCE: 22

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Lys Ala Asn Ser Glu Asn Pro Asp Trp Asp Leu Asn Pro His
        35                  40                  45

```
Lys Asp Asn Trp Pro Asp Ala His Lys Val Gly Val Gly Ala Phe Gly
         50                  55                  60

Pro Gly Phe Thr Pro Pro His Gly Gly Leu Leu Gly Trp Ser Pro Gln
 65                  70                  75                  80

Ala Gln Gly Ile Leu Thr Ser Val Pro Ala Pro Pro Ala Ser
             85                  90                  95

Thr Asn Arg Gln Ser Gly Arg Gln Pro Thr Pro Leu
            100                 105
```

<210> SEQ ID NO 23
<211> LENGTH: 55
<212> TYPE: PRT
<213> ORGANISM: Artificial Sequence
<220> FEATURE:
<223> OTHER INFORMATION: Synthetic peptide

<400> SEQUENCE: 23

```
Ser Pro Pro Leu Arg Asp Thr His Pro Gln Ala Met Gln Trp Asn Ser
 1               5                  10                  15

Thr Thr Phe His Gln Thr Leu Gln Asp Pro Arg Val Arg Ala Leu Tyr
             20                  25                  30

Leu Pro Ala Gly Gly Ser Ser Gly Thr Val Ser Pro Ala Gln Asn
         35                  40                  45

Thr Val Ser Ala Ile Ser Ser
     50                  55
```

<210> SEQ ID NO 24
<211> LENGTH: 237
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (94)..(94)
<223> OTHER INFORMATION: Xaa can be any naturally occurring amino acid

<400> SEQUENCE: 24

```
Ile Leu Ser Thr Thr Gly Asp Pro Val Pro Asn Met Glu Asn Ile Ala
 1               5                  10                  15

Ser Gly Leu Leu Gly Pro Leu Leu Val Leu Gln Ala Gly Phe Phe Ser
             20                  25                  30

Leu Thr Lys Ile Leu Thr Ile Pro Gln Ser Leu Asp Ser Trp Trp Thr
         35                  40                  45

Ser Leu Ser Phe Leu Gly Gly Thr Pro Val Cys Leu Gly Gln Asn Ser
 50                  55                  60

Gln Ser Pro Ile Ser Ser His Ser Pro Thr Cys Cys Pro Pro Ile Cys
 65                  70                  75                  80

Pro Gly Tyr Arg Trp Met Tyr Leu Arg Arg Phe Ile Ile Xaa Leu Cys
             85                  90                  95

Ile Leu Leu Leu Cys Leu Ile Phe Leu Leu Val Leu Leu Asp Tyr Gln
                100                 105                 110

Gly Met Leu Pro Val Cys Pro Leu Ile Pro Gly Ser Ser Thr Thr Ser
            115                 120                 125

Thr Gly Pro Cys Lys Thr Cys Thr Thr Pro Ala Gln Gly Thr Ser Met
        130                 135                 140

Phe Pro Ser Cys Cys Cys Thr Lys Pro Thr Asp Gly Asn Cys Thr Cys
145                 150                 155                 160
```

```
Ile Pro Ile Pro Ser Ser Trp Ala Phe Ala Lys Tyr Leu Trp Glu Trp
                165                 170                 175

Ala Ser Val Arg Phe Ser Trp Leu Ser Leu Leu Val Pro Phe Val Gln
            180                 185                 190

Trp Phe Val Gly Leu Ser Pro Thr Val Trp Leu Ser Val Ile Trp Met
        195                 200                 205

Met Trp Tyr Trp Gly Pro Ser Leu Tyr Asn Ile Leu Ser Pro Phe Met
    210                 215                 220

Pro Leu Leu Pro Ile Phe Phe Cys Leu Trp Val Tyr Ile
225                 230                 235

<210> SEQ ID NO 25
<211> LENGTH: 292
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (149)..(149)
<223> OTHER INFORMATION: Xaa can be any naturally occurring amino acid

<400> SEQUENCE: 25

Ser Pro Pro Leu Arg Asp Thr His Pro Gln Ala Met Gln Trp Asn Ser
1               5                   10                  15

Thr Thr Phe His Gln Thr Leu Gln Asp Pro Arg Val Arg Ala Leu Tyr
            20                  25                  30

Leu Pro Ala Gly Gly Ser Ser Gly Thr Val Ser Pro Ala Gln Asn
        35                  40                  45

Thr Val Ser Ala Ile Ser Ser Ile Leu Ser Thr Thr Gly Asp Pro Val
50                  55                  60

Pro Asn Met Glu Asn Ile Ala Ser Gly Leu Leu Gly Pro Leu Leu Val
65                  70                  75                  80

Leu Gln Ala Gly Phe Phe Ser Leu Thr Lys Ile Leu Thr Ile Pro Gln
                85                  90                  95

Ser Leu Asp Ser Trp Trp Thr Ser Leu Ser Phe Leu Gly Gly Thr Pro
            100                 105                 110

Val Cys Leu Gly Gln Asn Ser Gln Ser Pro Ile Ser Ser His Ser Pro
        115                 120                 125

Thr Cys Cys Pro Pro Ile Cys Pro Gly Tyr Arg Trp Met Tyr Leu Arg
    130                 135                 140

Arg Phe Ile Ile Xaa Leu Cys Ile Leu Leu Leu Cys Leu Ile Phe Leu
145                 150                 155                 160

Leu Val Leu Leu Asp Tyr Gln Gly Met Leu Pro Val Cys Pro Leu Ile
                165                 170                 175

Pro Gly Ser Ser Thr Thr Ser Thr Gly Pro Cys Lys Thr Cys Thr Thr
            180                 185                 190

Pro Ala Gln Gly Thr Ser Met Phe Pro Ser Cys Cys Thr Lys Pro
        195                 200                 205

Thr Asp Gly Asn Cys Thr Cys Ile Pro Ile Pro Ser Ser Trp Ala Phe
    210                 215                 220

Ala Lys Tyr Leu Trp Glu Trp Ala Ser Val Arg Phe Ser Trp Leu Ser
225                 230                 235                 240

Leu Leu Val Pro Phe Val Gln Trp Phe Val Gly Leu Ser Pro Thr Val
                245                 250                 255

Trp Leu Ser Val Ile Trp Met Met Trp Tyr Trp Gly Pro Ser Leu Tyr
            260                 265                 270
```

```
Asn Ile Leu Ser Pro Phe Met Pro Leu Leu Pro Ile Phe Phe Cys Leu
            275                 280                 285

Trp Val Tyr Ile
    290

<210> SEQ ID NO 26
<211> LENGTH: 400
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (257)..(257)
<223> OTHER INFORMATION: Xaa can be any naturally occurring amino acid

<400> SEQUENCE: 26

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Lys Ala Asn Ser Glu Asn Pro Asp Trp Asp Leu Asn Pro His
        35                  40                  45

Lys Asp Asn Trp Pro Asp Ala His Lys Val Gly Val Gly Ala Phe Gly
    50                  55                  60

Pro Gly Phe Thr Pro Pro His Gly Gly Leu Leu Gly Trp Ser Pro Gln
65                  70                  75                  80

Ala Gln Gly Ile Leu Thr Ser Val Pro Ala Ala Pro Pro Pro Ala Ser
                85                  90                  95

Thr Asn Arg Gln Ser Gly Arg Gln Pro Thr Pro Leu Ser Pro Pro Leu
            100                 105                 110

Arg Asp Thr His Pro Gln Ala Met Gln Trp Asn Ser Thr Thr Phe His
        115                 120                 125

Gln Thr Leu Gln Asp Pro Arg Val Arg Ala Leu Tyr Leu Pro Ala Gly
    130                 135                 140

Gly Ser Ser Ser Gly Thr Val Ser Pro Ala Gln Asn Thr Val Ser Ala
145                 150                 155                 160

Ile Ser Ser Ile Leu Ser Thr Thr Gly Asp Pro Val Pro Asn Met Glu
                165                 170                 175

Asn Ile Ala Ser Gly Leu Leu Gly Pro Leu Leu Val Leu Gln Ala Gly
            180                 185                 190

Phe Phe Ser Leu Thr Lys Ile Leu Thr Ile Pro Gln Ser Leu Asp Ser
        195                 200                 205

Trp Trp Thr Ser Leu Ser Phe Leu Gly Gly Thr Pro Val Cys Leu Gly
    210                 215                 220

Gln Asn Ser Gln Ser Pro Ile Ser Ser His Ser Pro Thr Cys Cys Pro
225                 230                 235                 240

Pro Ile Cys Pro Gly Tyr Arg Trp Met Tyr Leu Arg Arg Phe Ile Ile
                245                 250                 255

Xaa Leu Cys Ile Leu Leu Leu Cys Leu Ile Phe Leu Leu Val Leu Leu
            260                 265                 270

Asp Tyr Gln Gly Met Leu Pro Val Cys Pro Leu Ile Pro Gly Ser Ser
        275                 280                 285

Thr Thr Ser Thr Gly Pro Cys Lys Thr Cys Thr Thr Pro Ala Gln Gly
    290                 295                 300

Thr Ser Met Phe Pro Ser Cys Cys Cys Thr Lys Pro Thr Asp Gly Asn
```

```
                305                 310                 315                 320

Cys Thr Cys Ile Pro Ile Pro Ser Ser Trp Ala Phe Ala Lys Tyr Leu
                325                 330                 335

Trp Glu Trp Ala Ser Val Arg Phe Ser Trp Leu Ser Leu Leu Val Pro
                340                 345                 350

Phe Val Gln Trp Phe Val Gly Leu Ser Pro Thr Val Trp Leu Ser Val
                355                 360                 365

Ile Trp Met Met Trp Tyr Trp Gly Pro Ser Leu Tyr Asn Ile Leu Ser
        370                 375                 380

Pro Phe Met Pro Leu Leu Pro Ile Phe Phe Cys Leu Trp Val Tyr Ile
385                 390                 395                 400

<210> SEQ ID NO 27
<211> LENGTH: 108
<212> TYPE: PRT
<213> ORGANISM: Artificial Sequence
<220> FEATURE:
<223> OTHER INFORMATION: Synthetic peptide

<400> SEQUENCE: 27

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Lys Ala Asn Ser Glu Asn Pro Asp Trp Asp Leu Asn Pro His
        35                  40                  45

Lys Asp Asn Trp Pro Asp Ala Asn Lys Val Gly Val Gly Ala Phe Gly
    50                  55                  60

Pro Gly Phe Thr Pro Pro His Gly Gly Leu Leu Gly Trp Ser Pro Gln
65                  70                  75                  80

Ala Gln Gly Leu Leu Thr Thr Val Pro Ala Ala Pro Pro Pro Ala Ser
                85                  90                  95

Thr Asn Arg Gln Ser Gly Arg Gln Pro Thr Pro Leu
            100                 105

<210> SEQ ID NO 28
<211> LENGTH: 55
<212> TYPE: PRT
<213> ORGANISM: Artificial Sequence
<220> FEATURE:
<223> OTHER INFORMATION: Synthetic peptide

<400> SEQUENCE: 28

Ser Pro Pro Leu Arg Asp Thr His Pro Gln Ala Met Gln Trp Asn Ser
1               5                   10                  15

Thr Thr Phe His Gln Thr Leu Gln Asp Pro Arg Val Arg Ala Leu Tyr
            20                  25                  30

Phe Pro Ala Gly Gly Ser Ser Ser Gly Thr Val Ser Pro Ala Gln Asn
        35                  40                  45

Thr Val Ser Thr Ile Ser Ser
    50                  55

<210> SEQ ID NO 29
<211> LENGTH: 237
<212> TYPE: PRT
<213> ORGANISM: Artificial Sequence
<220> FEATURE:
<223> OTHER INFORMATION: Synthetic peptide

<400> SEQUENCE: 29
```

Ile Leu Ser Lys Thr Gly Asp Pro Val Pro Asn Met Glu Asn Ile Ala
1               5                   10                  15

Ser Gly Leu Leu Gly Pro Leu Leu Val Leu Gln Ala Gly Phe Phe Leu
                20                  25                  30

Leu Thr Lys Ile Leu Thr Ile Pro Gln Ser Leu Asp Ser Trp Trp Thr
            35                  40                  45

Ser Leu Asn Phe Leu Gly Gly Thr Pro Val Cys Leu Gly Gln Asn Ser
    50                  55                  60

Gln Ser Gln Ile Ser Ser His Ser Pro Thr Cys Cys Pro Pro Ile Cys
65              70                  75                  80

Pro Gly Tyr Arg Trp Met Cys Leu Arg Arg Phe Ile Ile Phe Leu Cys
                85                  90                  95

Ile Leu Leu Leu Cys Leu Ile Phe Leu Leu Val Leu Leu Asp Tyr Gln
                100                 105                 110

Gly Met Leu Pro Val Cys Pro Leu Ile Pro Gly Ser Ser Thr Thr Ser
                115                 120                 125

Thr Gly Pro Cys Lys Thr Cys Thr Thr Pro Ala Gln Gly Thr Ser Met
    130                 135                 140

Phe Pro Ser Cys Cys Cys Thr Lys Pro Thr Asp Gly Asn Cys Thr Cys
145                 150                 155                 160

Ile Pro Ile Pro Ser Ser Trp Ala Phe Ala Lys Tyr Leu Trp Glu Trp
                165                 170                 175

Ala Ser Val Arg Phe Ser Trp Leu Ser Leu Leu Val Pro Phe Val Gln
                180                 185                 190

Trp Phe Val Gly Leu Ser Pro Thr Val Trp Leu Ser Val Ile Trp Met
                195                 200                 205

Met Trp Phe Trp Gly Pro Ser Leu Tyr Asn Ile Leu Ser Pro Phe Met
    210                 215                 220

Pro Leu Leu Pro Ile Phe Phe Cys Leu Trp Val Tyr Ile
225                 230                 235

<210> SEQ ID NO 30
<211> LENGTH: 292
<212> TYPE: PRT
<213> ORGANISM: Artificial Sequence
<220> FEATURE:
<223> OTHER INFORMATION: Synthetic peptide

<400> SEQUENCE: 30

Ser Pro Pro Leu Arg Asp Thr His Pro Gln Ala Met Gln Trp Asn Ser
1               5                   10                  15

Thr Thr Phe His Gln Thr Leu Gln Asp Pro Arg Val Arg Ala Leu Tyr
                20                  25                  30

Phe Pro Ala Gly Gly Ser Ser Ser Gly Thr Val Ser Pro Ala Gln Asn
            35                  40                  45

Thr Val Ser Thr Ile Ser Ser Ile Leu Ser Lys Thr Gly Asp Pro Val
    50                  55                  60

Pro Asn Met Glu Asn Ile Ala Ser Gly Leu Leu Gly Pro Leu Leu Val
65              70                  75                  80

Leu Gln Ala Gly Phe Phe Leu Leu Thr Lys Ile Leu Thr Ile Pro Gln
                85                  90                  95

Ser Leu Asp Ser Trp Trp Thr Ser Leu Asn Phe Leu Gly Gly Thr Pro
                100                 105                 110

Val Cys Leu Gly Gln Asn Ser Gln Ser Gln Ile Ser Ser His Ser Pro
                115                 120                 125

```
Thr Cys Cys Pro Pro Ile Cys Pro Gly Tyr Arg Trp Met Cys Leu Arg
            130                 135                 140

Arg Phe Ile Ile Phe Leu Cys Ile Leu Leu Leu Cys Leu Ile Phe Leu
145                 150                 155                 160

Leu Val Leu Leu Asp Tyr Gln Gly Met Leu Pro Val Cys Pro Leu Ile
                165                 170                 175

Pro Gly Ser Ser Thr Thr Ser Thr Gly Pro Cys Lys Thr Cys Thr Thr
                180                 185                 190

Pro Ala Gln Gly Thr Ser Met Phe Pro Ser Cys Cys Cys Thr Lys Pro
            195                 200                 205

Thr Asp Gly Asn Cys Thr Cys Ile Pro Ile Pro Ser Ser Trp Ala Phe
210                 215                 220

Ala Lys Tyr Leu Trp Glu Trp Ala Ser Val Arg Phe Ser Trp Leu Ser
225                 230                 235                 240

Leu Leu Val Pro Phe Val Gln Trp Phe Val Gly Leu Ser Pro Thr Val
                245                 250                 255

Trp Leu Ser Val Ile Trp Met Met Trp Phe Trp Gly Pro Ser Leu Tyr
                260                 265                 270

Asn Ile Leu Ser Pro Phe Met Pro Leu Leu Pro Ile Phe Phe Cys Leu
                275                 280                 285

Trp Val Tyr Ile
    290

<210> SEQ ID NO 31
<211> LENGTH: 400
<212> TYPE: PRT
<213> ORGANISM: Artificial Sequence
<220> FEATURE:
<223> OTHER INFORMATION: Synthetic peptide

<400> SEQUENCE: 31

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
                20                  25                  30

Ala Phe Lys Ala Asn Ser Glu Asn Pro Asp Trp Asp Leu Asn Pro His
            35                  40                  45

Lys Asp Asn Trp Pro Asp Ala Asn Lys Val Gly Val Gly Ala Phe Gly
50                  55                  60

Pro Gly Phe Thr Pro Pro His Gly Gly Leu Leu Gly Trp Ser Pro Gln
65                  70                  75                  80

Ala Gln Gly Leu Leu Thr Thr Val Pro Ala Ala Pro Pro Pro Ala Ser
                85                  90                  95

Thr Asn Arg Gln Ser Gly Arg Gln Pro Thr Pro Leu Ser Pro Pro Leu
            100                 105                 110

Arg Asp Thr His Pro Gln Ala Met Gln Trp Asn Ser Thr Thr Phe His
        115                 120                 125

Gln Thr Leu Gln Asp Pro Arg Val Arg Ala Leu Tyr Phe Pro Ala Gly
    130                 135                 140

Gly Ser Ser Ser Gly Thr Val Ser Pro Ala Gln Asn Thr Val Ser Thr
145                 150                 155                 160

Ile Ser Ser Ile Leu Ser Lys Thr Gly Asp Pro Val Pro Asn Met Glu
                165                 170                 175

Asn Ile Ala Ser Gly Leu Leu Gly Pro Leu Leu Val Leu Gln Ala Gly
            180                 185                 190
```

```
Phe Phe Leu Leu Thr Lys Ile Leu Thr Ile Pro Gln Ser Leu Asp Ser
            195                 200                 205

Trp Trp Thr Ser Leu Asn Phe Leu Gly Gly Thr Pro Val Cys Leu Gly
        210                 215                 220

Gln Asn Ser Gln Ser Gln Ile Ser Ser His Ser Pro Thr Cys Cys Pro
225                 230                 235                 240

Pro Ile Cys Pro Gly Tyr Arg Trp Met Cys Leu Arg Arg Phe Ile Ile
                245                 250                 255

Phe Leu Cys Ile Leu Leu Leu Cys Leu Ile Phe Leu Leu Val Leu Leu
            260                 265                 270

Asp Tyr Gln Gly Met Leu Pro Val Cys Pro Leu Ile Pro Gly Ser Ser
                275                 280                 285

Thr Thr Ser Thr Gly Pro Cys Lys Thr Cys Thr Thr Pro Ala Gln Gly
        290                 295                 300

Thr Ser Met Phe Pro Ser Cys Cys Cys Thr Lys Pro Thr Asp Gly Asn
305                 310                 315                 320

Cys Thr Cys Ile Pro Ile Pro Ser Ser Trp Ala Phe Ala Lys Tyr Leu
                325                 330                 335

Trp Glu Trp Ala Ser Val Arg Phe Ser Trp Leu Ser Leu Leu Val Pro
            340                 345                 350

Phe Val Gln Trp Phe Val Gly Leu Ser Pro Thr Val Trp Leu Ser Val
        355                 360                 365

Ile Trp Met Met Trp Phe Trp Gly Pro Ser Leu Tyr Asn Ile Leu Ser
370                 375                 380

Pro Phe Met Pro Leu Leu Pro Ile Phe Phe Cys Leu Trp Val Tyr Ile
385                 390                 395                 400

<210> SEQ ID NO 32
<211> LENGTH: 108
<212> TYPE: PRT
<213> ORGANISM: Artificial Sequence
<220> FEATURE:
<223> OTHER INFORMATION: Synthetic peptide

<400> SEQUENCE: 32

Met Gly Gly Trp Ser Ser Lys Pro Arg Gln Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Asn
        35                  40                  45

Lys Asp His Trp Pro Glu Ala Asn Gln Val Gly Ala Gly Ala Phe Gly
50                  55                  60

Pro Gly Phe Thr Pro Pro His Gly Gly Leu Leu Gly Trp Ser Pro Gln
65                  70                  75                  80

Ala Gln Gly Ile Leu Thr Thr Leu Pro Ala Ala Pro Pro Pro Ala Ser
                85                  90                  95

Thr Asn Arg Gln Ser Gly Arg Gln Pro Thr Pro Ile
            100                 105

<210> SEQ ID NO 33
<211> LENGTH: 55
<212> TYPE: PRT
<213> ORGANISM: Artificial Sequence
<220> FEATURE:
<223> OTHER INFORMATION: Synthetic peptide
```

```
<400> SEQUENCE: 33

Ser Pro Pro Leu Arg Asp Ser His Pro Gln Ala Met Gln Trp Asn Ser
1               5                   10                  15

Thr Thr Phe His Gln Ala Leu Leu Asp Pro Arg Val Arg Gly Leu Tyr
                20                  25                  30

Phe Pro Ala Gly Gly Ser Ser Gly Thr Val Asn Pro Val Pro Thr
            35                  40                  45

Thr Ala Ser Pro Ile Ser Ser
50                  55

<210> SEQ ID NO 34
<211> LENGTH: 237
<212> TYPE: PRT
<213> ORGANISM: Artificial Sequence
<220> FEATURE:
<223> OTHER INFORMATION: Synthetic peptide

<400> SEQUENCE: 34

Ile Phe Ser Arg Thr Gly Asp Pro Ala Pro Asn Met Glu Ser Thr Thr
1               5                   10                  15

Ser Gly Phe Leu Gly Pro Leu Leu Val Leu Gln Ala Gly Phe Phe Leu
                20                  25                  30

Leu Thr Arg Ile Leu Thr Ile Pro Gln Ser Leu Asp Ser Trp Trp Thr
                35                  40                  45

Ser Leu Asn Phe Leu Gly Gly Ala Pro Thr Cys Pro Gly Gln Asn Ser
50                  55                  60

Gln Ser Pro Thr Ser Asn His Ser Pro Thr Ser Cys Pro Pro Thr Cys
65                  70                  75                  80

Pro Gly Tyr Arg Trp Met Cys Leu Arg Arg Phe Ile Ile Phe Leu Phe
                85                  90                  95

Ile Leu Leu Leu Cys Leu Ile Phe Leu Leu Val Leu Leu Asp Tyr Gln
                100                 105                 110

Gly Met Leu Pro Val Cys Pro Leu Leu Pro Gly Thr Ser Thr Thr Ser
                115                 120                 125

Thr Gly Pro Cys Arg Thr Cys Thr Ile Pro Ala Gln Gly Thr Ser Met
130                 135                 140

Phe Pro Ser Cys Cys Cys Thr Lys Pro Ser Asp Gly Asn Cys Thr Cys
145                 150                 155                 160

Ile Pro Ile Pro Ser Ser Trp Ala Phe Ala Arg Phe Leu Trp Glu Trp
                165                 170                 175

Ala Ser Val Arg Phe Ser Trp Leu Ser Leu Leu Val Pro Phe Val Gln
                180                 185                 190

Trp Phe Val Gly Leu Ser Pro Thr Val Trp Leu Ser Ala Ile Trp Met
                195                 200                 205

Met Trp Tyr Trp Gly Pro Ser Leu Tyr Asn Ile Leu Ser Pro Phe Leu
210                 215                 220

Pro Leu Leu Pro Ile Phe Phe Cys Leu Trp Val Tyr Ile
225                 230                 235

<210> SEQ ID NO 35
<211> LENGTH: 292
<212> TYPE: PRT
<213> ORGANISM: Artificial Sequence
<220> FEATURE:
<223> OTHER INFORMATION: Synthetic peptide

<400> SEQUENCE: 35
```

```
Ser Pro Pro Leu Arg Asp Ser His Pro Gln Ala Met Gln Trp Asn Ser
1               5                   10                  15

Thr Thr Phe His Gln Ala Leu Leu Asp Pro Arg Val Arg Gly Leu Tyr
            20                  25                  30

Phe Pro Ala Gly Gly Ser Ser Gly Thr Val Asn Pro Val Pro Thr
        35                  40                  45

Thr Ala Ser Pro Ile Ser Ser Ile Phe Ser Arg Thr Gly Asp Pro Ala
    50                  55                  60

Pro Asn Met Glu Ser Thr Ser Gly Phe Leu Gly Pro Leu Leu Val
65                  70                  75                  80

Leu Gln Ala Gly Phe Phe Leu Leu Thr Arg Ile Leu Thr Ile Pro Gln
            85                  90                  95

Ser Leu Asp Ser Trp Trp Thr Ser Leu Asn Phe Leu Gly Gly Ala Pro
            100                 105                 110

Thr Cys Pro Gly Gln Asn Ser Gln Ser Pro Thr Ser Asn His Ser Pro
            115                 120                 125

Thr Ser Cys Pro Pro Thr Cys Pro Gly Tyr Arg Trp Met Cys Leu Arg
    130                 135                 140

Arg Phe Ile Ile Phe Leu Phe Ile Leu Leu Cys Leu Ile Phe Leu
145                 150                 155                 160

Leu Val Leu Leu Asp Tyr Gln Gly Met Leu Pro Val Cys Pro Leu Leu
                165                 170                 175

Pro Gly Thr Ser Thr Thr Ser Thr Gly Pro Cys Arg Thr Cys Thr Ile
            180                 185                 190

Pro Ala Gln Gly Thr Ser Met Phe Pro Ser Cys Cys Cys Thr Lys Pro
        195                 200                 205

Ser Asp Gly Asn Cys Thr Cys Ile Pro Ile Pro Ser Ser Trp Ala Phe
    210                 215                 220

Ala Arg Phe Leu Trp Glu Trp Ala Ser Val Arg Phe Ser Trp Leu Ser
225                 230                 235                 240

Leu Leu Val Pro Phe Val Gln Trp Phe Val Gly Leu Ser Pro Thr Val
                245                 250                 255

Trp Leu Ser Ala Ile Trp Met Met Trp Tyr Trp Gly Pro Ser Leu Tyr
            260                 265                 270

Asn Ile Leu Ser Pro Phe Leu Pro Leu Leu Pro Ile Phe Phe Cys Leu
            275                 280                 285

Trp Val Tyr Ile
        290
```

<210> SEQ ID NO 36
<211> LENGTH: 400
<212> TYPE: PRT
<213> ORGANISM: Artificial Sequence
<220> FEATURE:
<223> OTHER INFORMATION: Synthetic peptide

<400> SEQUENCE: 36

```
Met Gly Gly Trp Ser Ser Lys Pro Arg Gln Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Asn
        35                  40                  45

Lys Asp His Trp Pro Glu Ala Asn Gln Val Gly Ala Gly Ala Phe Gly
    50                  55                  60
```

Pro Gly Phe Thr Pro Pro His Gly Gly Leu Leu Gly Trp Ser Pro Gln
65                  70                  75                  80

Ala Gln Gly Ile Leu Thr Thr Leu Pro Ala Ala Pro Pro Ala Ser
            85                  90                  95

Thr Asn Arg Gln Ser Gly Arg Gln Pro Thr Pro Ile Ser Pro Pro Leu
            100                 105                 110

Arg Asp Ser His Pro Gln Ala Met Gln Trp Asn Ser Thr Thr Phe His
            115                 120                 125

Gln Ala Leu Leu Asp Pro Arg Val Arg Gly Leu Tyr Phe Pro Ala Gly
            130                 135                 140

Gly Ser Ser Ser Gly Thr Val Asn Pro Val Pro Thr Thr Ala Ser Pro
145                 150                 155                 160

Ile Ser Ser Ile Phe Ser Arg Thr Gly Asp Pro Ala Pro Asn Met Glu
                165                 170                 175

Ser Thr Thr Ser Gly Phe Leu Gly Pro Leu Leu Val Leu Gln Ala Gly
                180                 185                 190

Phe Phe Leu Leu Thr Arg Ile Leu Thr Ile Pro Gln Ser Leu Asp Ser
            195                 200                 205

Trp Trp Thr Ser Leu Asn Phe Leu Gly Gly Ala Pro Thr Cys Pro Gly
210                 215                 220

Gln Asn Ser Gln Ser Pro Thr Ser Asn His Ser Pro Thr Ser Cys Pro
225                 230                 235                 240

Pro Thr Cys Pro Gly Tyr Arg Trp Met Cys Leu Arg Arg Phe Ile Ile
                245                 250                 255

Phe Leu Phe Ile Leu Leu Leu Cys Leu Ile Phe Leu Leu Val Leu Leu
            260                 265                 270

Asp Tyr Gln Gly Met Leu Pro Val Cys Pro Leu Leu Pro Gly Thr Ser
            275                 280                 285

Thr Thr Ser Thr Gly Pro Cys Arg Thr Cys Thr Ile Pro Ala Gln Gly
            290                 295                 300

Thr Ser Met Phe Pro Ser Cys Cys Cys Thr Lys Pro Ser Asp Gly Asn
305                 310                 315                 320

Cys Thr Cys Ile Pro Ile Pro Ser Ser Trp Ala Phe Ala Arg Phe Leu
                325                 330                 335

Trp Glu Trp Ala Ser Val Arg Phe Ser Trp Leu Ser Leu Leu Val Pro
            340                 345                 350

Phe Val Gln Trp Phe Val Gly Leu Ser Pro Thr Val Trp Leu Ser Ala
            355                 360                 365

Ile Trp Met Met Trp Tyr Trp Gly Pro Ser Leu Tyr Asn Ile Leu Ser
            370                 375                 380

Pro Phe Leu Pro Leu Leu Pro Ile Phe Phe Cys Leu Trp Val Tyr Ile
385                 390                 395                 400

<210> SEQ ID NO 37
<211> LENGTH: 97
<212> TYPE: PRT
<213> ORGANISM: Artificial Sequence
<220> FEATURE:
<223> OTHER INFORMATION: Synthetic peptide

<400> SEQUENCE: 37

Met Gly Gln Asn Leu Ser Thr Ser Asn Pro Leu Gly Phe Phe Pro Asp
1               5                   10                  15

His Gln Leu Asp Pro Ala Phe Arg Ala Asn Thr Ala Asn Pro Asp Trp
            20                  25                  30

```
Asp Phe Asn Pro Asn Lys Asp Thr Trp Pro Asp Ala Asn Lys Val Gly
         35                  40                  45

Ala Gly Ala Phe Gly Leu Gly Phe Thr Pro Pro His Gly Gly Leu Leu
 50                  55                  60

Gly Trp Ser Pro Gln Ala Gln Gly Ile Leu Gln Thr Leu Pro Ala Asn
 65                  70                  75                  80

Pro Pro Pro Ala Ser Thr Asn Arg Gln Ser Gly Arg Gln Pro Thr Pro
                 85                  90                  95

Leu

<210> SEQ ID NO 38
<211> LENGTH: 55
<212> TYPE: PRT
<213> ORGANISM: Artificial Sequence
<220> FEATURE:
<223> OTHER INFORMATION: Synthetic peptide

<400> SEQUENCE: 38

Ser Pro Pro Leu Arg Asn Thr His Pro Gln Ala Met Gln Trp Asn Ser
 1               5                  10                  15

Thr Thr Phe His Gln Thr Leu Gln Asp Pro Arg Val Arg Gly Leu Tyr
                 20                  25                  30

Phe Pro Ala Gly Gly Ser Ser Gly Thr Val Asn Pro Val Leu Thr
             35                  40                  45

Thr Ala Ser Pro Leu Ser Ser
             50                  55

<210> SEQ ID NO 39
<211> LENGTH: 237
<212> TYPE: PRT
<213> ORGANISM: Artificial Sequence
<220> FEATURE:
<223> OTHER INFORMATION: Synthetic peptide

<400> SEQUENCE: 39

Ile Phe Ser Arg Ile Gly Asp Pro Ala Leu Asn Met Glu Asn Ile Thr
 1               5                  10                  15

Ser Gly Phe Leu Gly Pro Leu Leu Val Leu Gln Ala Gly Phe Phe Leu
                 20                  25                  30

Leu Thr Arg Ile Leu Thr Ile Pro Gln Ser Leu Asp Ser Trp Trp Thr
             35                  40                  45

Ser Leu Asn Phe Leu Gly Gly Thr Thr Val Cys Leu Gly Gln Asn Ser
 50                  55                  60

Gln Ser Pro Thr Ser Asn His Ser Pro Thr Ser Cys Pro Pro Thr Cys
 65                  70                  75                  80

Pro Gly Tyr Arg Trp Met Cys Leu Arg Arg Phe Ile Ile Phe Leu Phe
                 85                  90                  95

Ile Leu Leu Leu Cys Leu Ile Phe Leu Leu Val Leu Leu Asp Tyr Gln
             100                 105                 110

Gly Met Leu Pro Val Cys Pro Leu Ile Pro Gly Ser Ser Thr Thr Ser
             115                 120                 125

Thr Gly Pro Cys Arg Thr Cys Met Thr Thr Ala Gln Gly Thr Ser Met
         130                 135                 140

Tyr Pro Ser Cys Cys Cys Thr Lys Pro Ser Asp Gly Asn Cys Thr Cys
145                 150                 155                 160

Ile Pro Ile Pro Ser Ser Trp Ala Phe Gly Lys Phe Leu Trp Glu Trp
                 165                 170                 175
```

```
Ala Ser Ala Arg Phe Ser Trp Leu Ser Leu Val Pro Phe Val Gln
            180                 185                 190

Trp Phe Val Gly Leu Ser Pro Thr Val Trp Leu Ser Val Ile Trp Met
        195                 200                 205

Met Trp Tyr Trp Gly Pro Ser Leu Tyr Ser Ile Leu Ser Pro Phe Leu
    210                 215                 220

Pro Leu Leu Pro Ile Phe Phe Cys Leu Trp Val Tyr Ile
225                 230                 235

<210> SEQ ID NO 40
<211> LENGTH: 292
<212> TYPE: PRT
<213> ORGANISM: Artificial Sequence
<220> FEATURE:
<223> OTHER INFORMATION: Synthetic peptide

<400> SEQUENCE: 40

Ser Pro Pro Leu Arg Asn Thr His Pro Gln Ala Met Gln Trp Asn Ser
1               5                  10                  15

Thr Thr Phe His Gln Thr Leu Gln Asp Pro Arg Val Arg Gly Leu Tyr
            20                  25                  30

Phe Pro Ala Gly Gly Ser Ser Gly Thr Val Asn Pro Val Leu Thr
        35                  40                  45

Thr Ala Ser Pro Leu Ser Ser Ile Phe Ser Arg Ile Gly Asp Pro Ala
50                  55                  60

Leu Asn Met Glu Asn Ile Thr Ser Gly Phe Leu Gly Pro Leu Leu Val
65                  70                  75                  80

Leu Gln Ala Gly Phe Phe Leu Leu Thr Arg Ile Leu Thr Ile Pro Gln
                85                  90                  95

Ser Leu Asp Ser Trp Trp Thr Ser Leu Asn Phe Leu Gly Gly Thr Thr
            100                 105                 110

Val Cys Leu Gly Gln Asn Ser Gln Ser Pro Thr Ser Asn His Ser Pro
        115                 120                 125

Thr Ser Cys Pro Pro Thr Cys Pro Gly Tyr Arg Trp Met Cys Leu Arg
130                 135                 140

Arg Phe Ile Ile Phe Leu Phe Ile Leu Leu Leu Cys Leu Ile Phe Leu
145                 150                 155                 160

Leu Val Leu Leu Asp Tyr Gln Gly Met Leu Pro Val Cys Pro Leu Ile
                165                 170                 175

Pro Gly Ser Ser Thr Thr Ser Thr Gly Pro Cys Arg Thr Cys Met Thr
            180                 185                 190

Thr Ala Gln Gly Thr Ser Met Tyr Pro Ser Cys Cys Cys Thr Lys Pro
        195                 200                 205

Ser Asp Gly Asn Cys Thr Cys Ile Pro Ile Pro Ser Ser Trp Ala Phe
210                 215                 220

Gly Lys Phe Leu Trp Glu Trp Ala Ser Ala Arg Phe Ser Trp Leu Ser
225                 230                 235                 240

Leu Leu Val Pro Phe Val Gln Trp Phe Val Gly Leu Ser Pro Thr Val
                245                 250                 255

Trp Leu Ser Val Ile Trp Met Met Trp Tyr Trp Gly Pro Ser Leu Tyr
            260                 265                 270

Ser Ile Leu Ser Pro Phe Leu Pro Leu Leu Pro Ile Phe Phe Cys Leu
        275                 280                 285

Trp Val Tyr Ile
    290
```

```
<210> SEQ ID NO 41
<211> LENGTH: 389
<212> TYPE: PRT
<213> ORGANISM: Artificial Sequence
<220> FEATURE:
<223> OTHER INFORMATION: Synthetic peptide

<400> SEQUENCE: 41

Met Gly Gln Asn Leu Ser Thr Ser Asn Pro Leu Gly Phe Phe Pro Asp
1               5                   10                  15

His Gln Leu Asp Pro Ala Phe Arg Ala Asn Thr Ala Asn Pro Asp Trp
            20                  25                  30

Asp Phe Asn Pro Asn Lys Asp Thr Trp Pro Asp Ala Asn Lys Val Gly
        35                  40                  45

Ala Gly Ala Phe Gly Leu Gly Phe Thr Pro Pro His Gly Gly Leu Leu
    50                  55                  60

Gly Trp Ser Pro Gln Ala Gln Gly Ile Leu Gln Thr Leu Pro Ala Asn
65                  70                  75                  80

Pro Pro Pro Ala Ser Thr Asn Arg Gln Ser Gly Arg Gln Pro Thr Pro
                85                  90                  95

Leu Ser Pro Pro Leu Arg Asn Thr His Pro Gln Ala Met Gln Trp Asn
            100                 105                 110

Ser Thr Thr Phe His Gln Thr Leu Gln Asp Pro Arg Val Arg Gly Leu
        115                 120                 125

Tyr Phe Pro Ala Gly Gly Ser Ser Gly Thr Val Asn Pro Val Leu
    130                 135                 140

Thr Thr Ala Ser Pro Leu Ser Ser Ile Phe Ser Arg Ile Gly Asp Pro
145                 150                 155                 160

Ala Leu Asn Met Glu Asn Ile Thr Ser Gly Phe Leu Gly Pro Leu Leu
                165                 170                 175

Val Leu Gln Ala Gly Phe Phe Leu Leu Thr Arg Ile Leu Thr Ile Pro
            180                 185                 190

Gln Ser Leu Asp Ser Trp Trp Thr Ser Leu Asn Phe Leu Gly Gly Thr
        195                 200                 205

Thr Val Cys Leu Gly Gln Asn Ser Gln Ser Pro Thr Ser Asn His Ser
    210                 215                 220

Pro Thr Ser Cys Pro Pro Thr Cys Pro Gly Tyr Arg Trp Met Cys Leu
225                 230                 235                 240

Arg Arg Phe Ile Ile Phe Leu Phe Ile Leu Leu Leu Cys Leu Ile Phe
                245                 250                 255

Leu Leu Val Leu Leu Asp Tyr Gln Gly Met Leu Pro Val Cys Pro Leu
            260                 265                 270

Ile Pro Gly Ser Ser Thr Thr Ser Thr Gly Pro Cys Arg Thr Cys Met
        275                 280                 285

Thr Thr Ala Gln Gly Thr Ser Met Tyr Pro Ser Cys Cys Cys Thr Lys
    290                 295                 300

Pro Ser Asp Gly Asn Cys Thr Cys Ile Pro Ile Pro Ser Ser Trp Ala
305                 310                 315                 320

Phe Gly Lys Phe Leu Trp Glu Trp Ala Ser Ala Arg Phe Ser Trp Leu
                325                 330                 335

Ser Leu Leu Val Pro Phe Val Gln Trp Phe Val Gly Leu Ser Pro Thr
            340                 345                 350

Val Trp Leu Ser Val Ile Trp Met Met Trp Tyr Trp Gly Pro Ser Leu
        355                 360                 365
```

```
Tyr Ser Ile Leu Ser Pro Phe Leu Pro Leu Pro Ile Phe Phe Cys
    370                 375                 380

Leu Trp Val Tyr Ile
385

<210> SEQ ID NO 42
<211> LENGTH: 107
<212> TYPE: PRT
<213> ORGANISM: Artificial Sequence
<220> FEATURE:
<223> OTHER INFORMATION: Synthetic peptide

<400> SEQUENCE: 42

Met Gly Leu Ser Trp Thr Val Pro Leu Glu Trp Gly Lys Asn Ile Ser
1               5                   10                  15

Thr Thr Asn Pro Leu Gly Phe Phe Pro Asp His Gln Leu Asp Pro Ala
            20                  25                  30

Phe Arg Ala Asn Thr Arg Asn Pro Asp Trp Asp His Asn Pro Asn Lys
        35                  40                  45

Asp His Trp Thr Glu Ala Asn Lys Val Gly Val Gly Ala Phe Gly Pro
    50                  55                  60

Gly Phe Thr Pro Pro His Gly Gly Leu Leu Gly Trp Ser Pro Gln Ala
65                  70                  75                  80

Gln Gly Met Leu Lys Thr Leu Pro Ala Asp Pro Pro Ala Ser Thr
                85                  90                  95

Asn Arg Gln Ser Gly Arg Gln Pro Thr Pro Ile
            100                 105

<210> SEQ ID NO 43
<211> LENGTH: 55
<212> TYPE: PRT
<213> ORGANISM: Artificial Sequence
<220> FEATURE:
<223> OTHER INFORMATION: Synthetic peptide

<400> SEQUENCE: 43

Thr Pro Pro Leu Arg Asp Thr His Pro Gln Ala Met Gln Trp Asn Ser
1               5                   10                  15

Thr Thr Phe His Gln Ala Leu Gln Asp Pro Arg Val Arg Gly Leu Tyr
            20                  25                  30

Phe Pro Ala Gly Gly Ser Ser Gly Thr Val Asn Pro Val Pro Thr
        35                  40                  45

Thr Ala Ser Leu Ile Ser Ser
    50                  55

<210> SEQ ID NO 44
<211> LENGTH: 237
<212> TYPE: PRT
<213> ORGANISM: Artificial Sequence
<220> FEATURE:
<223> OTHER INFORMATION: Synthetic peptide

<400> SEQUENCE: 44

Ile Phe Ser Arg Ile Gly Asp Pro Ala Pro Asn Met Glu Ser Ile Thr
1               5                   10                  15

Ser Gly Phe Leu Gly Pro Leu Leu Val Leu Gln Ala Gly Phe Phe Leu
            20                  25                  30

Leu Thr Lys Ile Leu Thr Ile Pro Gln Ser Leu Asp Ser Trp Trp Thr
        35                  40                  45

Ser Leu Asn Phe Leu Gly Gly Ala Pro Val Cys Leu Gly Gln Asn Ser
```

```
                50                  55                  60
Gln Ser Pro Thr Ser Asn His Ser Pro Thr Ser Cys Pro Pro Ile Cys
 65                  70                  75                  80

Pro Gly Tyr Arg Trp Met Cys Leu Arg Arg Phe Ile Ile Phe Leu Phe
                 85                  90                  95

Ile Leu Leu Leu Cys Leu Ile Phe Leu Leu Val Leu Leu Asp Tyr Gln
                100                 105                 110

Gly Met Leu Pro Val Cys Pro Leu Ile Pro Gly Ser Ser Thr Thr Ser
                115                 120                 125

Thr Gly Pro Cys Arg Thr Cys Met Thr Leu Ala Gln Gly Thr Ser Met
                130                 135                 140

Phe Pro Ser Cys Cys Cys Ser Lys Pro Ser Asp Gly Asn Cys Thr Cys
145                 150                 155                 160

Ile Pro Ile Pro Ser Ser Trp Ala Phe Gly Lys Phe Leu Trp Glu Trp
                165                 170                 175

Ala Ser Ala Arg Phe Ser Trp Leu Ser Leu Leu Val Pro Phe Val Gln
                180                 185                 190

Trp Phe Ala Gly Leu Ser Pro Thr Val Trp Leu Ser Val Ile Trp Met
                195                 200                 205

Met Trp Tyr Trp Gly Pro Ser Leu Tyr Asp Ile Leu Ser Pro Phe Ile
                210                 215                 220

Pro Leu Leu Pro Ile Phe Phe Cys Leu Trp Val Tyr Ile
225                 230                 235

<210> SEQ ID NO 45
<211> LENGTH: 292
<212> TYPE: PRT
<213> ORGANISM: Artificial Sequence
<220> FEATURE:
<223> OTHER INFORMATION: Synthetic peptide

<400> SEQUENCE: 45

Thr Pro Pro Leu Arg Asp Thr His Pro Gln Ala Met Gln Trp Asn Ser
  1               5                  10                  15

Thr Thr Phe His Gln Ala Leu Gln Asp Pro Arg Val Arg Gly Leu Tyr
                 20                  25                  30

Phe Pro Ala Gly Gly Ser Ser Gly Thr Val Asn Pro Val Pro Thr Thr
                 35                  40                  45

Thr Ala Ser Leu Ile Ser Ser Ile Phe Ser Arg Ile Gly Asp Pro Ala
 50                  55                  60

Pro Asn Met Glu Ser Ile Thr Ser Gly Phe Leu Gly Pro Leu Leu Val
 65                  70                  75                  80

Leu Gln Ala Gly Phe Phe Leu Leu Thr Lys Ile Leu Thr Ile Pro Gln
                 85                  90                  95

Ser Leu Asp Ser Trp Trp Thr Ser Leu Asn Phe Leu Gly Gly Ala Pro
                100                 105                 110

Val Cys Leu Gly Gln Asn Ser Gln Ser Pro Thr Ser Asn His Ser Pro
                115                 120                 125

Thr Ser Cys Pro Pro Ile Cys Pro Gly Tyr Arg Trp Met Cys Leu Arg
130                 135                 140

Arg Phe Ile Ile Phe Leu Phe Ile Leu Leu Leu Cys Leu Ile Phe Leu
145                 150                 155                 160

Leu Val Leu Leu Asp Tyr Gln Gly Met Leu Pro Val Cys Pro Leu Ile
                165                 170                 175

Pro Gly Ser Ser Thr Thr Ser Thr Gly Pro Cys Arg Thr Cys Met Thr
```

```
            180                 185                 190
Leu Ala Gln Gly Thr Ser Met Phe Pro Ser Cys Cys Cys Ser Lys Pro
        195                 200                 205
Ser Asp Gly Asn Cys Thr Cys Ile Pro Ile Pro Ser Ser Trp Ala Phe
    210                 215                 220
Gly Lys Phe Leu Trp Glu Trp Ala Ser Ala Arg Phe Ser Trp Leu Ser
225                 230                 235                 240
Leu Leu Val Pro Phe Val Gln Trp Phe Ala Gly Leu Ser Pro Thr Val
                245                 250                 255
Trp Leu Ser Val Ile Trp Met Met Trp Tyr Trp Gly Pro Ser Leu Tyr
            260                 265                 270
Asp Ile Leu Ser Pro Phe Ile Pro Leu Leu Pro Ile Phe Phe Cys Leu
        275                 280                 285
Trp Val Tyr Ile
        290

<210> SEQ ID NO 46
<211> LENGTH: 399
<212> TYPE: PRT
<213> ORGANISM: Artificial Sequence
<220> FEATURE:
<223> OTHER INFORMATION: Synthetic peptide

<400> SEQUENCE: 46

Met Gly Leu Ser Trp Thr Val Pro Leu Glu Trp Gly Lys Asn Ile Ser
1               5                   10                  15
Thr Thr Asn Pro Leu Gly Phe Phe Pro Asp His Gln Leu Asp Pro Ala
            20                  25                  30
Phe Arg Ala Asn Thr Arg Asn Pro Asp Trp Asp His Asn Pro Asn Lys
        35                  40                  45
Asp His Trp Thr Glu Ala Asn Lys Val Gly Val Gly Ala Phe Gly Pro
    50                  55                  60
Gly Phe Thr Pro Pro His Gly Gly Leu Leu Gly Trp Ser Pro Gln Ala
65                  70                  75                  80
Gln Gly Met Leu Lys Thr Leu Pro Ala Asp Pro Pro Ala Ser Thr
                85                  90                  95
Asn Arg Gln Ser Gly Arg Gln Pro Thr Pro Ile Thr Pro Pro Leu Arg
            100                 105                 110
Asp Thr His Pro Gln Ala Met Gln Trp Asn Ser Thr Thr Phe His Gln
        115                 120                 125
Ala Leu Gln Asp Pro Arg Val Arg Gly Leu Tyr Phe Pro Ala Gly Gly
    130                 135                 140
Ser Ser Ser Gly Thr Val Asn Pro Val Pro Thr Thr Ala Ser Leu Ile
145                 150                 155                 160
Ser Ser Ile Phe Ser Arg Ile Gly Asp Pro Ala Pro Asn Met Glu Ser
                165                 170                 175
Ile Thr Ser Gly Phe Leu Gly Pro Leu Leu Val Leu Gln Ala Gly Phe
            180                 185                 190
Phe Leu Leu Thr Lys Ile Leu Thr Ile Pro Gln Ser Leu Asp Ser Trp
        195                 200                 205
Trp Thr Ser Leu Asn Phe Leu Gly Gly Ala Pro Val Cys Leu Gly Gln
    210                 215                 220
Asn Ser Gln Ser Pro Thr Ser Asn His Ser Pro Thr Ser Cys Pro Pro
225                 230                 235                 240
Ile Cys Pro Gly Tyr Arg Trp Met Cys Leu Arg Arg Phe Ile Ile Phe
```

```
                        245                 250                 255
Leu Phe Ile Leu Leu Cys Leu Ile Phe Leu Leu Val Leu Leu Asp
                260                 265                 270

Tyr Gln Gly Met Leu Pro Val Cys Pro Leu Ile Pro Gly Ser Ser Thr
                275                 280                 285

Thr Ser Thr Gly Pro Cys Arg Thr Cys Met Thr Leu Ala Gln Gly Thr
            290                 295                 300

Ser Met Phe Pro Ser Cys Cys Ser Lys Pro Ser Asp Gly Asn Cys
305                 310                 315                 320

Thr Cys Ile Pro Ile Pro Ser Ser Trp Ala Phe Gly Lys Phe Leu Trp
                325                 330                 335

Glu Trp Ala Ser Ala Arg Phe Ser Trp Leu Ser Leu Leu Val Pro Phe
                340                 345                 350

Val Gln Trp Phe Ala Gly Leu Ser Pro Thr Val Trp Leu Ser Val Ile
                355                 360                 365

Trp Met Met Trp Tyr Trp Gly Pro Ser Leu Tyr Asp Ile Leu Ser Pro
                370                 375                 380

Phe Ile Pro Leu Leu Pro Ile Phe Phe Cys Leu Trp Val Tyr Ile
385                 390                 395

<210> SEQ ID NO 47
<211> LENGTH: 108
<212> TYPE: PRT
<213> ORGANISM: Artificial Sequence
<220> FEATURE:
<223> OTHER INFORMATION: Synthetic peptide

<400> SEQUENCE: 47

Met Gly Ala Pro Leu Ser Thr Thr Arg Arg Gly Met Gly Gln Asn Leu
1               5                   10                  15

Ser Val Pro Asn Pro Leu Gly Phe Phe Pro Asp His Gln Leu Asp Pro
                20                  25                  30

Leu Phe Arg Ala Asn Ser Ser Ser Pro Asp Trp Asp Phe Asn Lys Asn
            35                  40                  45

Lys Asp Asn Trp Pro Met Ala Asn Lys Val Gly Val Gly Gly Tyr Gly
50                  55                  60

Pro Gly Phe Thr Pro Pro His Gly Gly Leu Leu Gly Trp Ser Pro Gln
65                  70                  75                  80

Ala Gln Gly Val Leu Thr Thr Leu Pro Ala Asp Pro Pro Pro Ala Ser
                85                  90                  95

Thr Asn Arg Arg Ser Gly Arg Lys Pro Thr Pro Val
            100                 105

<210> SEQ ID NO 48
<211> LENGTH: 55
<212> TYPE: PRT
<213> ORGANISM: Artificial Sequence
<220> FEATURE:
<223> OTHER INFORMATION: Synthetic peptide

<400> SEQUENCE: 48

Ser Pro Pro Leu Arg Asp Thr His Pro Gln Ala Met Gln Trp Asn Ser
1               5                   10                  15

Thr Gln Phe His Gln Ala Leu Leu Asp Pro Arg Val Arg Ala Leu Tyr
                20                  25                  30

Phe Pro Ala Gly Gly Ser Ser Ser Glu Thr Gln Asn Pro Ala Pro Thr
            35                  40                  45
```

Ile Ala Ser Leu Thr Ser Ser
    50                  55

<210> SEQ ID NO 49
<211> LENGTH: 237
<212> TYPE: PRT
<213> ORGANISM: Artificial Sequence
<220> FEATURE:
<223> OTHER INFORMATION: Synthetic peptide

<400> SEQUENCE: 49

Ile Phe Leu Lys Thr Gly Gly Pro Ala Thr Asn Met Asp Asn Ile Thr
1               5                   10                  15

Ser Gly Leu Leu Gly Pro Leu Val Leu Gln Ala Val Cys Phe Leu
            20                  25                  30

Leu Thr Lys Ile Leu Thr Ile Pro Gln Ser Leu Asp Ser Trp Trp Thr
        35                  40                  45

Ser Leu Asn Phe Leu Gly Gly Thr Pro Gly Cys Pro Gly Gln Asn Ser
    50                  55                  60

Gln Ser Pro Thr Ser Asn His Leu Pro Thr Ser Cys Pro Pro Thr Cys
65                  70                  75                  80

Pro Gly Tyr Arg Trp Met Cys Leu Arg Arg Phe Ile Ile Phe Leu Phe
                85                  90                  95

Ile Leu Leu Leu Cys Leu Ile Phe Leu Leu Val Leu Val Asp Tyr Gln
            100                 105                 110

Gly Met Leu Pro Val Cys Pro Leu Pro Gly Ser Thr Thr Thr Ser
        115                 120                 125

Thr Gly Pro Cys Lys Thr Cys Thr Thr Leu Ala Gln Gly Thr Ser Met
130                 135                 140

Phe Pro Ser Cys Cys Cys Ser Lys Pro Ser Asp Gly Asn Cys Thr Cys
145                 150                 155                 160

Ile Pro Ile Pro Ser Ser Trp Ala Leu Gly Lys Tyr Leu Trp Glu Trp
                165                 170                 175

Ala Ser Ala Arg Phe Ser Trp Leu Ser Leu Leu Val Gln Phe Val Gln
            180                 185                 190

Trp Cys Val Gly Leu Ser Pro Thr Val Trp Leu Leu Val Ile Trp Met
        195                 200                 205

Ile Trp Tyr Trp Gly Pro Asn Leu Cys Ser Ile Leu Ser Pro Phe Ile
210                 215                 220

Pro Leu Leu Pro Ile Phe Cys Tyr Leu Trp Val Ser Ile
225                 230                 235

<210> SEQ ID NO 50
<211> LENGTH: 292
<212> TYPE: PRT
<213> ORGANISM: Artificial Sequence
<220> FEATURE:
<223> OTHER INFORMATION: Synthetic peptide

<400> SEQUENCE: 50

Ser Pro Pro Leu Arg Asp Thr His Pro Gln Ala Met Gln Trp Asn Ser
1               5                   10                  15

Thr Gln Phe His Gln Ala Leu Leu Asp Pro Arg Val Arg Ala Leu Tyr
            20                  25                  30

Phe Pro Ala Gly Gly Ser Ser Ser Glu Thr Gln Asn Pro Ala Pro Thr
        35                  40                  45

Ile Ala Ser Leu Thr Ser Ser Ile Phe Leu Lys Thr Gly Gly Pro Ala
    50                  55                  60

```
Thr Asn Met Asp Asn Ile Thr Ser Gly Leu Leu Gly Pro Leu Leu Val
 65                  70                  75                  80

Leu Gln Ala Val Cys Phe Leu Leu Thr Lys Ile Leu Thr Ile Pro Gln
                 85                  90                  95

Ser Leu Asp Ser Trp Trp Thr Ser Leu Asn Phe Leu Gly Gly Thr Pro
            100                 105                 110

Gly Cys Pro Gly Gln Asn Ser Gln Ser Pro Thr Ser Asn His Leu Pro
            115                 120                 125

Thr Ser Cys Pro Pro Thr Cys Pro Gly Tyr Arg Trp Met Cys Leu Arg
130                 135                 140

Arg Phe Ile Ile Phe Leu Phe Ile Leu Leu Leu Cys Leu Ile Phe Leu
145                 150                 155                 160

Leu Val Leu Val Asp Tyr Gln Gly Met Leu Pro Val Cys Pro Pro Leu
                165                 170                 175

Pro Gly Ser Thr Thr Thr Ser Thr Gly Pro Cys Lys Thr Cys Thr Thr
            180                 185                 190

Leu Ala Gln Gly Thr Ser Met Phe Pro Ser Cys Cys Cys Ser Lys Pro
            195                 200                 205

Ser Asp Gly Asn Cys Thr Cys Ile Pro Ile Pro Ser Ser Trp Ala Leu
            210                 215                 220

Gly Lys Tyr Leu Trp Glu Trp Ala Ser Ala Arg Phe Ser Trp Leu Ser
225                 230                 235                 240

Leu Leu Val Gln Phe Val Gln Trp Cys Val Gly Leu Ser Pro Thr Val
                245                 250                 255

Trp Leu Leu Val Ile Trp Met Ile Trp Tyr Trp Gly Pro Asn Leu Cys
            260                 265                 270

Ser Ile Leu Ser Pro Phe Ile Pro Leu Leu Pro Ile Phe Cys Tyr Leu
            275                 280                 285

Trp Val Ser Ile
            290

<210> SEQ ID NO 51
<211> LENGTH: 400
<212> TYPE: PRT
<213> ORGANISM: Artificial Sequence
<220> FEATURE:
<223> OTHER INFORMATION: Synthetic peptide

<400> SEQUENCE: 51

Met Gly Ala Pro Leu Ser Thr Thr Arg Arg Gly Met Gly Gln Asn Leu
  1               5                  10                  15

Ser Val Pro Asn Pro Leu Gly Phe Phe Pro Asp His Gln Leu Asp Pro
                 20                  25                  30

Leu Phe Arg Ala Asn Ser Ser Ser Pro Asp Trp Asp Phe Asn Lys Asn
             35                  40                  45

Lys Asp Asn Trp Pro Met Ala Asn Lys Val Gly Val Gly Gly Tyr Gly
         50                  55                  60

Pro Gly Phe Thr Pro Pro His Gly Gly Leu Leu Gly Trp Ser Pro Gln
 65                  70                  75                  80

Ala Gln Gly Val Leu Thr Thr Leu Pro Ala Asp Pro Pro Pro Ala Ser
                 85                  90                  95

Thr Asn Arg Arg Ser Gly Arg Lys Pro Thr Pro Val Ser Pro Pro Leu
            100                 105                 110

Arg Asp Thr His Pro Gln Ala Met Gln Trp Asn Ser Thr Gln Phe His
            115                 120                 125
```

Gln Ala Leu Leu Asp Pro Arg Val Arg Ala Leu Tyr Phe Pro Ala Gly
            130                 135                 140

Gly Ser Ser Ser Glu Thr Gln Asn Pro Ala Pro Thr Ile Ala Ser Leu
145                 150                 155                 160

Thr Ser Ser Ile Phe Leu Lys Thr Gly Gly Pro Ala Thr Asn Met Asp
            165                 170                 175

Asn Ile Thr Ser Gly Leu Leu Gly Pro Leu Leu Val Leu Gln Ala Val
            180                 185                 190

Cys Phe Leu Leu Thr Lys Ile Leu Thr Ile Pro Gln Ser Leu Asp Ser
            195                 200                 205

Trp Trp Thr Ser Leu Asn Phe Leu Gly Gly Thr Pro Gly Cys Pro Gly
            210                 215                 220

Gln Asn Ser Gln Ser Pro Thr Ser Asn His Leu Pro Thr Ser Cys Pro
225                 230                 235                 240

Pro Thr Cys Pro Gly Tyr Arg Trp Met Cys Leu Arg Arg Phe Ile Ile
            245                 250                 255

Phe Leu Phe Ile Leu Leu Leu Cys Leu Ile Phe Leu Leu Val Leu Val
            260                 265                 270

Asp Tyr Gln Gly Met Leu Pro Val Cys Pro Leu Pro Gly Ser Thr
            275                 280                 285

Thr Thr Ser Thr Gly Pro Cys Lys Thr Cys Thr Thr Leu Ala Gln Gly
290                 295                 300

Thr Ser Met Phe Pro Ser Cys Cys Cys Ser Lys Pro Ser Asp Gly Asn
305                 310                 315                 320

Cys Thr Cys Ile Pro Ile Pro Ser Ser Trp Ala Leu Gly Lys Tyr Leu
            325                 330                 335

Trp Glu Trp Ala Ser Ala Arg Phe Ser Trp Leu Ser Leu Leu Val Gln
            340                 345                 350

Phe Val Gln Trp Cys Val Gly Leu Ser Pro Thr Val Trp Leu Leu Val
            355                 360                 365

Ile Trp Met Ile Trp Tyr Trp Gly Pro Asn Leu Cys Ser Ile Leu Ser
            370                 375                 380

Pro Phe Ile Pro Leu Leu Pro Ile Phe Cys Tyr Leu Trp Val Ser Ile
385                 390                 395                 400

<210> SEQ ID NO 52
<211> LENGTH: 108
<212> TYPE: PRT
<213> ORGANISM: Artificial Sequence
<220> FEATURE:
<223> OTHER INFORMATION: Synthetic peptide

<400> SEQUENCE: 52

Met Gly Ala Pro Leu Ser Thr Thr Arg Arg Gly Met Gly Gln Asn Leu
1               5                   10                  15

Ser Val Pro Asn Pro Leu Gly Phe Phe Pro Glu His Gln Leu Asp Pro
            20                  25                  30

Leu Phe Arg Ala Asn Ser Ser Ser Pro Asp Trp Asp Phe Asn Lys Asn
            35                  40                  45

Lys Asp Thr Trp Pro Met Ala Asn Lys Val Gly Val Gly Gly Tyr Gly
            50                  55                  60

Pro Gly Phe Thr Pro Pro His Gly Gly Leu Leu Gly Trp Ser Pro Gln
65                  70                  75                  80

Ala Gln Gly Val Leu Thr Thr Leu Pro Ala Asp Pro Pro Pro Ala Ser
            85                  90                  95

Thr Asn Arg Arg Ser Gly Arg Lys Pro Thr Pro Val
            100                 105

<210> SEQ ID NO 53
<211> LENGTH: 55
<212> TYPE: PRT
<213> ORGANISM: Artificial Sequence
<220> FEATURE:
<223> OTHER INFORMATION: Synthetic peptide

<400> SEQUENCE: 53

Ser Pro Pro Leu Arg Asp Thr His Pro Gln Ala Met Gln Trp Asn Ser
1               5                   10                  15

Thr Gln Phe His Gln Ala Leu Leu Asp Pro Arg Val Arg Ala Leu Tyr
            20                  25                  30

Phe Pro Ala Gly Gly Ser Ser Glu Thr Gln Asn Pro Ala Pro Thr
        35                  40                  45

Ile Ala Ser Leu Thr Ser Ser
    50                  55

<210> SEQ ID NO 54
<211> LENGTH: 237
<212> TYPE: PRT
<213> ORGANISM: Artificial Sequence
<220> FEATURE:
<223> OTHER INFORMATION: Synthetic peptide

<400> SEQUENCE: 54

Ile Phe Ser Lys Thr Gly Gly Pro Ala Met Asn Met Asp Ser Ile Thr
1               5                   10                  15

Ser Gly Leu Leu Gly Pro Leu Leu Val Leu Gln Ala Val Cys Phe Leu
            20                  25                  30

Leu Thr Lys Ile Leu Thr Ile Pro Gln Ser Leu Asp Ser Trp Trp Thr
            35                  40                  45

Ser Leu Asn Phe Leu Gly Gly Leu Pro Gly Cys Pro Gly Gln Asn Ser
    50                  55                  60

Gln Ser Pro Thr Ser Asn His Leu Pro Thr Ser Cys Pro Pro Thr Cys
65                  70                  75                  80

Pro Gly Tyr Arg Trp Met Cys Leu Arg Arg Phe Ile Ile Phe Leu Phe
                85                  90                  95

Ile Leu Leu Leu Cys Leu Ile Phe Leu Val Leu Leu Asp Tyr Gln
                100                 105                 110     Gln

Gly Met Leu Pro Val Cys Pro Leu Ile Pro Gly Ser Thr Thr Thr Ser
            115                 120                 125

Thr Gly Pro Cys Lys Thr Cys Thr Thr Leu Ala Gln Gly Thr Ser Met
    130                 135                 140

Phe Pro Ser Cys Cys Cys Ser Lys Pro Ser Asp Gly Asn Cys Thr Cys
145                 150                 155                 160

Ile Pro Ile Pro Ser Ser Trp Ala Leu Gly Lys Tyr Leu Trp Glu Trp
                165                 170                 175

Ala Ser Ala Arg Phe Ser Trp Leu Ser Leu Leu Val Gln Phe Val Gln
            180                 185                 190

Trp Cys Val Gly Leu Ser Pro Thr Val Trp Leu Leu Val Ile Trp Met
            195                 200                 205

Ile Trp Tyr Trp Gly Pro Asn Leu Cys Ser Ile Leu Ser Pro Phe Ile
    210                 215                 220

Pro Leu Leu Pro Ile Phe Cys Tyr Leu Trp Val Ser Ile

<210> SEQ ID NO 55
<211> LENGTH: 292
<212> TYPE: PRT
<213> ORGANISM: Artificial Sequence
<220> FEATURE:
<223> OTHER INFORMATION: Synthetic peptide

<400> SEQUENCE: 55

Ser Pro Pro Leu Arg Asp Thr His Pro Gln Ala Met Gln Trp Asn Ser
1               5                   10                  15

Thr Gln Phe His Gln Ala Leu Leu Asp Pro Arg Val Arg Ala Leu Tyr
            20                  25                  30

Phe Pro Ala Gly Gly Ser Ser Glu Thr Gln Asn Pro Ala Pro Thr
        35                  40                  45

Ile Ala Ser Leu Thr Ser Ser Ile Phe Ser Lys Thr Gly Gly Pro Ala
    50                  55                  60

Met Asn Met Asp Ser Ile Thr Ser Gly Leu Leu Gly Pro Leu Leu Val
65                  70                  75                  80

Leu Gln Ala Val Cys Phe Leu Leu Thr Lys Ile Leu Thr Ile Pro Gln
                85                  90                  95

Ser Leu Asp Ser Trp Trp Thr Ser Leu Asn Phe Leu Gly Gly Leu Pro
            100                 105                 110

Gly Cys Pro Gly Gln Asn Ser Gln Ser Pro Thr Ser Asn His Leu Pro
        115                 120                 125

Thr Ser Cys Pro Pro Thr Cys Pro Gly Tyr Arg Trp Met Cys Leu Arg
130                 135                 140

Arg Phe Ile Ile Phe Leu Phe Ile Leu Leu Cys Leu Ile Phe Leu
145                 150                 155                 160

Leu Val Leu Leu Asp Tyr Gln Gly Met Leu Pro Val Cys Pro Leu Ile
                165                 170                 175

Pro Gly Ser Thr Thr Thr Ser Thr Gly Pro Cys Lys Thr Cys Thr Thr
            180                 185                 190

Leu Ala Gln Gly Thr Ser Met Phe Pro Ser Cys Cys Ser Lys Pro
        195                 200                 205

Ser Asp Gly Asn Cys Thr Cys Ile Pro Ile Pro Ser Ser Trp Ala Leu
210                 215                 220

Gly Lys Tyr Leu Trp Glu Trp Ala Ser Ala Arg Phe Ser Trp Leu Ser
225                 230                 235                 240

Leu Leu Val Gln Phe Val Gln Trp Cys Val Gly Leu Ser Pro Thr Val
                245                 250                 255

Trp Leu Leu Val Ile Trp Met Ile Trp Tyr Trp Gly Pro Asn Leu Cys
            260                 265                 270

Ser Ile Leu Ser Pro Phe Ile Pro Leu Leu Pro Ile Phe Cys Tyr Leu
        275                 280                 285

Trp Val Ser Ile
    290

<210> SEQ ID NO 56
<211> LENGTH: 400
<212> TYPE: PRT
<213> ORGANISM: Artificial Sequence
<220> FEATURE:
<223> OTHER INFORMATION: Synthetic peptide

<400> SEQUENCE: 56

Met Gly Ala Pro Leu Ser Thr Thr Arg Arg Gly Met Gly Gln Asn Leu
1               5                   10                  15

Ser Val Pro Asn Pro Leu Gly Phe Phe Pro Glu His Gln Leu Asp Pro
            20                  25                  30

Leu Phe Arg Ala Asn Ser Ser Pro Asp Trp Asp Phe Asn Lys Asn
        35                  40                  45

Lys Asp Thr Trp Pro Met Ala Asn Lys Val Gly Val Gly Gly Tyr Gly
    50                  55                  60

Pro Gly Phe Thr Pro Pro His Gly Gly Leu Leu Gly Trp Ser Pro Gln
65              70                  75                  80

Ala Gln Gly Val Leu Thr Thr Leu Pro Ala Asp Pro Pro Pro Ala Ser
                85                  90                  95

Thr Asn Arg Arg Ser Gly Arg Lys Pro Thr Pro Val Ser Pro Pro Leu
            100                 105                 110

Arg Asp Thr His Pro Gln Ala Met Gln Trp Asn Ser Thr Gln Phe His
            115                 120                 125

Gln Ala Leu Leu Asp Pro Arg Val Arg Ala Leu Tyr Phe Pro Ala Gly
        130                 135                 140

Gly Ser Ser Ser Glu Thr Gln Asn Pro Ala Pro Thr Ile Ala Ser Leu
145                 150                 155                 160

Thr Ser Ser Ile Phe Ser Lys Thr Gly Gly Pro Ala Met Asn Met Asp
                165                 170                 175

Ser Ile Thr Ser Gly Leu Leu Gly Pro Leu Leu Val Leu Gln Ala Val
            180                 185                 190

Cys Phe Leu Leu Thr Lys Ile Leu Thr Ile Pro Gln Ser Leu Asp Ser
        195                 200                 205

Trp Trp Thr Ser Leu Asn Phe Leu Gly Gly Leu Pro Gly Cys Pro Gly
210                 215                 220

Gln Asn Ser Gln Ser Pro Thr Ser Asn His Leu Pro Thr Ser Cys Pro
225                 230                 235                 240

Pro Thr Cys Pro Gly Tyr Arg Trp Met Cys Leu Arg Arg Phe Ile Ile
            245                 250                 255

Phe Leu Phe Ile Leu Leu Leu Cys Leu Ile Phe Leu Leu Val Leu Leu
            260                 265                 270

Asp Tyr Gln Gly Met Leu Pro Val Cys Pro Leu Ile Pro Gly Ser Thr
        275                 280                 285

Thr Thr Ser Thr Gly Pro Cys Lys Thr Cys Thr Thr Leu Ala Gln Gly
        290                 295                 300

Thr Ser Met Phe Pro Ser Cys Cys Cys Ser Lys Pro Ser Asp Gly Asn
305                 310                 315                 320

Cys Thr Cys Ile Pro Ile Pro Ser Ser Trp Ala Leu Gly Lys Tyr Leu
            325                 330                 335

Trp Glu Trp Ala Ser Ala Arg Phe Ser Trp Leu Ser Leu Leu Val Gln
        340                 345                 350

Phe Val Gln Trp Cys Val Gly Leu Ser Pro Thr Val Trp Leu Leu Val
            355                 360                 365

Ile Trp Met Ile Trp Tyr Trp Gly Pro Asn Leu Cys Ser Ile Leu Ser
        370                 375                 380

Pro Phe Ile Pro Leu Leu Pro Ile Phe Cys Tyr Leu Trp Val Ser Ile
385                 390                 395                 400

<210> SEQ ID NO 57
<211> LENGTH: 107
<212> TYPE: PRT

```
<213> ORGANISM: Artificial Sequence
<220> FEATURE:
<223> OTHER INFORMATION: Synthetic peptide

<400> SEQUENCE: 57

Met Gly Leu Ser Trp Thr Val Pro Leu Glu Trp Gly Lys Asn Leu Ser
1               5                   10                  15

Ala Ser Asn Pro Leu Gly Phe Leu Pro Asp His Gln Leu Asp Pro Ala
                20                  25                  30

Phe Arg Ala Asn Thr Asn Pro Asp Trp Asp Phe Asn Pro Lys Lys
            35                  40                  45

Asp Pro Trp Pro Glu Ala Asn Lys Val Gly Val Gly Ala Tyr Gly Pro
        50                  55                  60

Gly Phe Thr Pro Pro His Gly Gly Leu Leu Gly Trp Ser Pro Gln Ser
65                  70                  75                  80

Gln Gly Thr Leu Thr Thr Leu Pro Ala Asp Pro Pro Ala Ser Thr
                85                  90                  95

Asn Arg Gln Ser Gly Arg Gln Pro Thr Pro Ile
            100                 105

<210> SEQ ID NO 58
<211> LENGTH: 55
<212> TYPE: PRT
<213> ORGANISM: Artificial Sequence
<220> FEATURE:
<223> OTHER INFORMATION: Synthetic peptide

<400> SEQUENCE: 58

Ser Pro Pro Leu Arg Asp Ser His Pro Gln Ala Met Gln Trp Asn Ser
1               5                   10                  15

Thr Ala Phe His Gln Ala Leu Gln Asn Pro Lys Val Arg Gly Leu Tyr
                20                  25                  30

Phe Pro Ala Gly Gly Ser Ser Gly Ile Val Asn Pro Val Pro Thr
            35                  40                  45

Ile Ala Ser His Ile Ser Ser
        50                  55

<210> SEQ ID NO 59
<211> LENGTH: 237
<212> TYPE: PRT
<213> ORGANISM: Artificial Sequence
<220> FEATURE:
<223> OTHER INFORMATION: Synthetic peptide

<400> SEQUENCE: 59

Ile Phe Ser Arg Ile Gly Asp Pro Ala Pro Asn Met Glu Asn Ile Thr
1               5                   10                  15

Ser Gly Phe Leu Gly Pro Leu Leu Val Leu Gln Ala Gly Phe Phe Leu
                20                  25                  30

Leu Thr Arg Ile Leu Thr Ile Pro Gln Ser Leu Asp Ser Trp Trp Thr
            35                  40                  45

Ser Leu Asn Phe Leu Gly Gly Val Pro Val Cys Pro Gly Leu Asn Ser
        50                  55                  60

Gln Ser Pro Thr Ser Asn His Ser Pro Ile Ser Cys Pro Pro Thr Cys
65                  70                  75                  80

Pro Gly Tyr Arg Trp Met Cys Leu Arg Arg Phe Ile Ile Phe Leu Phe
                85                  90                  95

Ile Leu Leu Leu Cys Leu Ile Phe Leu Leu Val Leu Leu Asp Tyr Gln
            100                 105                 110
```

```
Gly Met Leu Pro Val Cys Pro Leu Ile Pro Gly Ser Ser Thr Thr Ser
            115                 120                 125

Thr Gly Pro Cys Lys Thr Cys Thr Thr Pro Ala Gln Gly Asn Ser Met
    130                 135                 140

Tyr Pro Ser Cys Cys Thr Lys Pro Ser Asp Gly Asn Cys Thr Cys
145                 150                 155                 160

Ile Pro Ile Pro Ser Ser Trp Ala Phe Ala Lys Tyr Leu Trp Glu Trp
                165                 170                 175

Ala Ser Val Arg Phe Ser Trp Leu Ser Leu Leu Val Pro Phe Val Gln
            180                 185                 190

Trp Phe Val Gly Leu Ser Pro Thr Val Trp Leu Ser Ala Ile Trp Met
        195                 200                 205

Met Trp Tyr Trp Gly Pro Asn Leu Tyr Asn Ile Leu Ser Pro Phe Ile
    210                 215                 220

Pro Leu Leu Pro Ile Phe Phe Cys Leu Trp Val Tyr Ile
225                 230                 235
```

<210> SEQ ID NO 60
<211> LENGTH: 292
<212> TYPE: PRT
<213> ORGANISM: Artificial Sequence
<220> FEATURE:
<223> OTHER INFORMATION: Synthetic peptide

<400> SEQUENCE: 60

```
Ser Pro Pro Leu Arg Asp Ser His Pro Gln Ala Met Gln Trp Asn Ser
1               5                   10                  15

Thr Ala Phe His Gln Ala Leu Gln Asn Pro Lys Val Arg Gly Leu Tyr
            20                  25                  30

Phe Pro Ala Gly Gly Ser Ser Gly Ile Val Asn Pro Val Pro Thr
        35                  40                  45

Ile Ala Ser His Ile Ser Ser Ile Phe Ser Arg Ile Gly Asp Pro Ala
50                  55                  60

Pro Asn Met Glu Asn Ile Thr Ser Gly Phe Leu Gly Pro Leu Leu Val
65                  70                  75                  80

Leu Gln Ala Gly Phe Phe Leu Leu Thr Arg Ile Leu Thr Ile Pro Gln
                85                  90                  95

Ser Leu Asp Ser Trp Trp Thr Ser Leu Asn Phe Leu Gly Gly Val Pro
            100                 105                 110

Val Cys Pro Gly Leu Asn Ser Gln Ser Pro Thr Ser Asn His Ser Pro
        115                 120                 125

Ile Ser Cys Pro Pro Thr Cys Pro Gly Tyr Arg Trp Met Cys Leu Arg
    130                 135                 140

Arg Phe Ile Ile Phe Leu Phe Ile Leu Leu Leu Cys Leu Ile Phe Leu
145                 150                 155                 160

Leu Val Leu Leu Asp Tyr Gln Gly Met Leu Pro Val Cys Pro Leu Ile
                165                 170                 175

Pro Gly Ser Ser Thr Thr Ser Thr Gly Pro Cys Lys Thr Cys Thr Thr
            180                 185                 190

Pro Ala Gln Gly Asn Ser Met Tyr Pro Ser Cys Cys Cys Thr Lys Pro
        195                 200                 205

Ser Asp Gly Asn Cys Thr Cys Ile Pro Ile Pro Ser Ser Trp Ala Phe
    210                 215                 220

Ala Lys Tyr Leu Trp Glu Trp Ala Ser Val Arg Phe Ser Trp Leu Ser
225                 230                 235                 240
```

```
Leu Leu Val Pro Phe Val Gln Trp Phe Val Gly Leu Ser Pro Thr Val
                245                 250                 255

Trp Leu Ser Ala Ile Trp Met Met Trp Tyr Trp Gly Pro Asn Leu Tyr
            260                 265                 270

Asn Ile Leu Ser Pro Phe Ile Pro Leu Leu Pro Ile Phe Phe Cys Leu
        275                 280                 285

Trp Val Tyr Ile
    290

<210> SEQ ID NO 61
<211> LENGTH: 399
<212> TYPE: PRT
<213> ORGANISM: Artificial Sequence
<220> FEATURE:
<223> OTHER INFORMATION: Synthetic peptide

<400> SEQUENCE: 61

Met Gly Leu Ser Trp Thr Val Pro Leu Glu Trp Gly Lys Asn Leu Ser
1               5                   10                  15

Ala Ser Asn Pro Leu Gly Phe Leu Pro Asp His Gln Leu Asp Pro Ala
            20                  25                  30

Phe Arg Ala Asn Thr Asn Asn Pro Asp Trp Asp Phe Asn Pro Lys Lys
        35                  40                  45

Asp Pro Trp Pro Glu Ala Asn Lys Val Gly Val Gly Ala Tyr Gly Pro
    50                  55                  60

Gly Phe Thr Pro Pro His Gly Gly Leu Leu Gly Trp Ser Pro Gln Ser
65                  70                  75                  80

Gln Gly Thr Leu Thr Thr Leu Pro Ala Asp Pro Pro Ala Ser Ser Thr
                85                  90                  95

Asn Arg Gln Ser Gly Arg Gln Pro Thr Pro Ile Ser Pro Pro Leu Arg
            100                 105                 110

Asp Ser His Pro Gln Ala Met Gln Trp Asn Ser Thr Ala Phe His Gln
        115                 120                 125

Ala Leu Gln Asn Pro Lys Val Arg Gly Leu Tyr Phe Pro Ala Gly Gly
    130                 135                 140

Ser Ser Ser Gly Ile Val Asn Pro Val Pro Thr Ile Ala Ser His Ile
145                 150                 155                 160

Ser Ser Ile Phe Ser Arg Ile Gly Asp Pro Ala Pro Asn Met Glu Asn
                165                 170                 175

Ile Thr Ser Gly Phe Leu Gly Pro Leu Leu Val Leu Gln Ala Gly Phe
            180                 185                 190

Phe Leu Leu Thr Arg Ile Leu Thr Ile Pro Gln Ser Leu Asp Ser Trp
        195                 200                 205

Trp Thr Ser Leu Asn Phe Leu Gly Gly Val Pro Val Cys Pro Gly Leu
    210                 215                 220

Asn Ser Gln Ser Pro Thr Ser Asn His Ser Pro Ile Ser Cys Pro Pro
225                 230                 235                 240

Thr Cys Pro Gly Tyr Arg Trp Met Cys Leu Arg Arg Phe Ile Ile Phe
                245                 250                 255

Leu Phe Ile Leu Leu Leu Cys Leu Ile Phe Leu Leu Val Leu Leu Asp
            260                 265                 270

Tyr Gln Gly Met Leu Pro Val Cys Pro Leu Ile Pro Gly Ser Ser Thr
        275                 280                 285

Thr Ser Thr Gly Pro Cys Lys Thr Cys Thr Thr Pro Ala Gln Gly Asn
    290                 295                 300
```

```
Ser Met Tyr Pro Ser Cys Cys Thr Lys Pro Ser Asp Gly Asn Cys
305                 310                 315                 320

Thr Cys Ile Pro Ile Pro Ser Ser Trp Ala Phe Ala Lys Tyr Leu Trp
                325                 330                 335

Glu Trp Ala Ser Val Arg Phe Ser Trp Leu Ser Leu Leu Val Pro Phe
            340                 345                 350

Val Gln Trp Phe Val Gly Leu Ser Pro Thr Val Trp Leu Ser Ala Ile
        355                 360                 365

Trp Met Met Trp Tyr Trp Gly Pro Asn Leu Tyr Asn Ile Leu Ser Pro
    370                 375                 380

Phe Ile Pro Leu Leu Pro Ile Phe Phe Cys Leu Trp Val Tyr Ile
385                 390                 395
```

<210> SEQ ID NO 62
<211> LENGTH: 108
<212> TYPE: PRT
<213> ORGANISM: Artificial Sequence
<220> FEATURE:
<223> OTHER INFORMATION: Synthetic peptide

<400> SEQUENCE: 62

```
Met Gly Ala Pro Leu Ser Thr Ala Arg Arg Gly Met Gly Gln Asn Leu
1               5                   10                  15

Ser Val Pro Asn Pro Leu Gly Phe Phe Pro Asp His Gln Leu Asp Pro
            20                  25                  30

Leu Phe Arg Ala Asn Ser Ser Pro Asp Trp Asp Phe Asn Thr Asn
        35                  40                  45

Lys Asp Asn Trp Pro Met Ala Asn Lys Val Gly Val Gly Gly Phe Gly
50                  55                  60

Pro Gly Phe Thr Pro Pro His Gly Gly Leu Leu Gly Trp Ser Pro Gln
65                  70                  75                  80

Ala Gln Gly Ile Leu Thr Thr Ser Pro Pro Asp Pro Pro Ala Ser
                85                  90                  95

Thr Asn Arg Arg Ser Gly Arg Lys Pro Thr Pro Val
            100                 105
```

<210> SEQ ID NO 63
<211> LENGTH: 55
<212> TYPE: PRT
<213> ORGANISM: Artificial Sequence
<220> FEATURE:
<223> OTHER INFORMATION: Synthetic peptide

<400> SEQUENCE: 63

```
Ser Pro Pro Leu Arg Asp Thr His Pro Gln Ala Met Gln Trp Asn Ser
1               5                   10                  15

Thr Gln Phe His Gln Ala Leu Leu Asp Pro Arg Val Arg Gly Leu Tyr
            20                  25                  30

Phe Pro Ala Gly Gly Ser Ser Glu Thr Gln Asn Pro Ala Pro Thr
        35                  40                  45

Ile Ala Ser Leu Thr Ser Ser
    50                  55
```

<210> SEQ ID NO 64
<211> LENGTH: 237
<212> TYPE: PRT
<213> ORGANISM: Artificial Sequence
<220> FEATURE:
<223> OTHER INFORMATION: Synthetic peptide

<400> SEQUENCE: 64

Ile Phe Ser Lys Thr Gly Asp Pro Ala Met Asn Met Glu Asn Ile Thr
1               5                   10                  15

Ser Gly Leu Leu Arg Pro Leu Leu Val Leu Gln Ala Val Cys Phe Leu
            20                  25                  30

Leu Thr Lys Ile Leu Thr Ile Pro Gln Ser Leu Asp Ser Trp Trp Thr
        35                  40                  45

Ser Leu Asn Phe Leu Gly Val Pro Pro Gly Cys Pro Gly Gln Asn Ser
    50                  55                  60

Gln Ser Pro Ile Ser Asn His Leu Pro Thr Ser Cys Pro Pro Thr Cys
65                  70                  75                  80

Pro Gly Tyr Arg Trp Met Cys Leu Arg Arg Phe Ile Ile Phe Leu Phe
                85                  90                  95

Ile Leu Leu Leu Cys Leu Ile Phe Leu Leu Val Leu Leu Asp Tyr Gln
            100                 105                 110

Gly Met Leu Pro Val Cys Pro Leu Leu Pro Gly Ser Thr Thr Thr Ser
            115                 120                 125

Thr Gly Pro Cys Lys Thr Cys Thr Thr Leu Ala Gln Gly Thr Ser Met
130                 135                 140

Phe Pro Ser Cys Cys Cys Thr Lys Pro Ser Asp Gly Asn Cys Thr Cys
145                 150                 155                 160

Ile Pro Ile Pro Ser Ser Trp Ala Phe Gly Lys Tyr Leu Trp Glu Trp
                165                 170                 175

Ala Ser Ala Arg Phe Ser Trp Leu Ser Leu Leu Val Gln Phe Val Gln
            180                 185                 190

Trp Cys Val Gly Leu Ser Pro Thr Val Trp Leu Leu Val Ile Trp Met
        195                 200                 205

Ile Trp Tyr Trp Gly Pro Asn Leu Cys Ser Ile Leu Ser Pro Phe Ile
210                 215                 220

Pro Leu Leu Pro Ile Phe Cys Tyr Leu Trp Ala Ser Ile
225                 230                 235

<210> SEQ ID NO 65
<211> LENGTH: 292
<212> TYPE: PRT
<213> ORGANISM: Artificial Sequence
<220> FEATURE:
<223> OTHER INFORMATION: Synthetic peptide

<400> SEQUENCE: 65

Ser Pro Pro Leu Arg Asp Thr His Pro Gln Ala Met Gln Trp Asn Ser
1               5                   10                  15

Thr Gln Phe His Gln Ala Leu Leu Asp Pro Arg Val Arg Gly Leu Tyr
            20                  25                  30

Phe Pro Ala Gly Gly Ser Ser Ser Glu Thr Gln Asn Pro Ala Pro Thr
        35                  40                  45

Ile Ala Ser Leu Thr Ser Ser Ile Phe Ser Lys Thr Gly Asp Pro Ala
    50                  55                  60

Met Asn Met Glu Asn Ile Thr Ser Gly Leu Leu Arg Pro Leu Leu Val
65                  70                  75                  80

Leu Gln Ala Val Cys Phe Leu Leu Thr Lys Ile Leu Thr Ile Pro Gln
                85                  90                  95

Ser Leu Asp Ser Trp Trp Thr Ser Leu Asn Phe Leu Gly Val Pro Pro
            100                 105                 110

Gly Cys Pro Gly Gln Asn Ser Gln Ser Pro Ile Ser Asn His Leu Pro
            115                 120                 125

Thr Ser Cys Pro Pro Thr Cys Pro Gly Tyr Arg Trp Met Cys Leu Arg
130                 135                 140

Arg Phe Ile Ile Phe Leu Phe Ile Leu Leu Leu Cys Leu Ile Phe Leu
145                 150                 155                 160

Leu Val Leu Leu Asp Tyr Gln Gly Met Leu Pro Val Cys Pro Leu Leu
                165                 170                 175

Pro Gly Ser Thr Thr Thr Ser Thr Gly Pro Cys Lys Thr Cys Thr Thr
            180                 185                 190

Leu Ala Gln Gly Thr Ser Met Phe Pro Ser Cys Cys Cys Thr Lys Pro
            195                 200                 205

Ser Asp Gly Asn Cys Thr Cys Ile Pro Ile Pro Ser Ser Trp Ala Phe
210                 215                 220

Gly Lys Tyr Leu Trp Glu Trp Ala Ser Ala Arg Phe Ser Trp Leu Ser
225                 230                 235                 240

Leu Leu Val Gln Phe Val Gln Trp Cys Val Gly Leu Ser Pro Thr Val
                245                 250                 255

Trp Leu Leu Val Ile Trp Met Ile Trp Tyr Trp Gly Pro Asn Leu Cys
            260                 265                 270

Ser Ile Leu Ser Pro Phe Ile Pro Leu Leu Pro Ile Phe Cys Tyr Leu
            275                 280                 285

Trp Ala Ser Ile
    290

<210> SEQ ID NO 66
<211> LENGTH: 400
<212> TYPE: PRT
<213> ORGANISM: Artificial Sequence
<220> FEATURE:
<223> OTHER INFORMATION: Synthetic peptide

<400> SEQUENCE: 66

Met Gly Ala Pro Leu Ser Thr Ala Arg Arg Gly Met Gly Gln Asn Leu
1               5                   10                  15

Ser Val Pro Asn Pro Leu Gly Phe Phe Pro Asp His Gln Leu Asp Pro
                20                  25                  30

Leu Phe Arg Ala Asn Ser Ser Ser Pro Asp Trp Asp Phe Asn Thr Asn
            35                  40                  45

Lys Asp Asn Trp Pro Met Ala Asn Lys Val Gly Val Gly Gly Phe Gly
        50                  55                  60

Pro Gly Phe Thr Pro Pro His Gly Gly Leu Leu Gly Trp Ser Pro Gln
65                  70                  75                  80

Ala Gln Gly Ile Leu Thr Thr Ser Pro Pro Asp Pro Pro Pro Ala Ser
                85                  90                  95

Thr Asn Arg Arg Ser Gly Arg Lys Pro Thr Pro Val Ser Pro Pro Leu
            100                 105                 110

Arg Asp Thr His Pro Gln Ala Met Gln Trp Asn Ser Thr Gln Phe His
        115                 120                 125

Gln Ala Leu Leu Asp Pro Arg Val Arg Gly Leu Tyr Phe Pro Ala Gly
    130                 135                 140

Gly Ser Ser Ser Glu Thr Gln Asn Pro Ala Pro Thr Ile Ala Ser Leu
145                 150                 155                 160

Thr Ser Ser Ile Phe Ser Lys Thr Gly Asp Pro Ala Met Asn Met Glu
                165                 170                 175

```
Asn Ile Thr Ser Gly Leu Leu Arg Pro Leu Val Leu Gln Ala Val
            180                 185                 190

Cys Phe Leu Leu Thr Lys Ile Leu Thr Ile Pro Gln Ser Leu Asp Ser
        195                 200                 205

Trp Trp Thr Ser Leu Asn Phe Leu Gly Val Pro Pro Gly Cys Pro Gly
    210                 215                 220

Gln Asn Ser Gln Ser Pro Ile Ser Asn His Leu Pro Thr Ser Cys Pro
225                 230                 235                 240

Pro Thr Cys Pro Gly Tyr Arg Trp Met Cys Leu Arg Arg Phe Ile Ile
                245                 250                 255

Phe Leu Phe Ile Leu Leu Leu Cys Leu Ile Phe Leu Leu Val Leu Leu
            260                 265                 270

Asp Tyr Gln Gly Met Leu Pro Val Cys Pro Leu Leu Pro Gly Ser Thr
        275                 280                 285

Thr Thr Ser Thr Gly Pro Cys Lys Thr Cys Thr Thr Leu Ala Gln Gly
    290                 295                 300

Thr Ser Met Phe Pro Ser Cys Cys Cys Thr Lys Pro Ser Asp Gly Asn
305                 310                 315                 320

Cys Thr Cys Ile Pro Ile Pro Ser Ser Trp Ala Phe Gly Lys Tyr Leu
                325                 330                 335

Trp Glu Trp Ala Ser Ala Arg Phe Ser Trp Leu Ser Leu Leu Val Gln
            340                 345                 350

Phe Val Gln Trp Cys Val Gly Leu Ser Pro Thr Val Trp Leu Leu Val
        355                 360                 365

Ile Trp Met Ile Trp Tyr Trp Gly Pro Asn Leu Cys Ser Ile Leu Ser
    370                 375                 380

Pro Phe Ile Pro Leu Leu Pro Ile Phe Cys Tyr Leu Trp Ala Ser Ile
385                 390                 395                 400

<210> SEQ ID NO 67
<211> LENGTH: 703
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(20)
<223> OTHER INFORMATION: Optional leader sequence
<220> FEATURE:
<221> NAME/KEY: MISC_FEATURE
<222> LOCATION: (21)..(129)
<223> OTHER INFORMATION: G28-8VL
<220> FEATURE:
<221> NAME/KEY: MISC_FEATURE
<222> LOCATION: (130)..(149)
<223> OTHER INFORMATION: Gly-Ser linker
<220> FEATURE:
<221> NAME/KEY: MISC_FEATURE
<222> LOCATION: (150)..(269)
<223> OTHER INFORMATION: G28-8VH
<220> FEATURE:
<221> NAME/KEY: MISC_FEATURE
<222> LOCATION: (270)..(503)
<223> OTHER INFORMATION: Hing-CH2-CH3
<220> FEATURE:
<221> NAME/KEY: MISC_FEATURE
<222> LOCATION: (504)..(533)
<223> OTHER INFORMATION: Gly-Ser linker
<220> FEATURE:
<221> NAME/KEY: MISC_FEATURE
<222> LOCATION: (534)..(697)
<223> OTHER INFORMATION: preS1/preS2
<220> FEATURE:
<221> NAME/KEY: MISC_FEATURE
```

<222> LOCATION: (698)..(703)
<223> OTHER INFORMATION: Optional 6x-His

<400> SEQUENCE: 67

```
Met Glu Thr Pro Ala Gln Leu Leu Phe Leu Leu Leu Trp Leu Pro
1               5                   10                  15

Asp Thr Thr Gly Asp Ile Gln Met Thr Gln Ser Pro Ala Ser Leu Ser
                20                  25                  30

Ala Ser Val Gly Glu Thr Val Thr Ile Thr Cys Arg Ala Ser Glu Lys
            35                  40                  45

Ile Tyr Ser Tyr Leu Ala Trp Tyr Gln Gln Lys Gln Gly Lys Ser Pro
    50                  55                  60

Gln Leu Leu Val Tyr Asn Ala Lys Thr Leu Ala Glu Gly Val Pro Ser
65                  70                  75                  80

Arg Phe Ser Val Ser Gly Ser Gly Thr Gln Phe Ser Leu Arg Ile Asn
                85                  90                  95

Ser Leu Gln Pro Glu Asp Phe Gly Thr Tyr Tyr Cys Gln His His Phe
                100                 105                 110

Gly Ser Pro Arg Thr Phe Gly Gly Gly Thr Lys Leu Glu Ile Lys Asp
            115                 120                 125

Leu Gly Gly Gly Gly Ser Gly Gly Gly Gly Ser Gly Gly Gly Gly Ser
130                 135                 140

Gly Gly Gly Gly Ser Thr Gly Glu Val Gln Leu Gln Gln Ser Gly Pro
145                 150                 155                 160

Glu Leu Val Lys Pro Gly Ala Ser Met Lys Ile Ser Cys Lys Ala Ser
                165                 170                 175

Gly Tyr Ser Phe Thr Gly Tyr Thr Met Asn Trp Val Lys Gln Ser His
            180                 185                 190

Gly Lys Thr Leu Glu Trp Ile Gly Leu Ile Asn Pro Tyr Asn Gly Val
            195                 200                 205

Thr Ser Tyr Asn Gln Lys Phe Lys Asp Lys Ala Thr Leu Thr Val Asp
            210                 215                 220

Lys Ser Ser Ser Thr Ala Tyr Met Glu Leu Leu Ser Leu Thr Ser Glu
225                 230                 235                 240

Asp Ser Ala Ile Tyr Tyr Cys Ala Arg Asp Tyr Asn Tyr Asp Tyr Phe
                245                 250                 255

Asp Tyr Trp Gly Gln Gly Thr Thr Leu Thr Val Ser Ser Asp Leu Glu
            260                 265                 270

Pro Lys Ser Ser Asp Lys Thr His Thr Cys Pro Pro Cys Pro Ala Pro
            275                 280                 285

Glu Leu Leu Gly Gly Ser Ser Val Phe Leu Phe Pro Pro Lys Pro Lys
290                 295                 300

Asp Thr Leu Met Ile Ser Arg Thr Pro Glu Val Thr Cys Val Val Val
305                 310                 315                 320

Asp Val Ser His Glu Asp Pro Glu Val Lys Phe Asn Trp Tyr Val Asp
                325                 330                 335

Gly Val Glu Val His Asn Ala Lys Thr Lys Pro Arg Glu Glu Gln Tyr
            340                 345                 350

Asn Ser Thr Tyr Arg Val Val Ser Val Leu Thr Val Leu His Gln Asp
            355                 360                 365

Trp Leu Asn Gly Lys Glu Tyr Lys Cys Ser Val Ser Asn Lys Ala Leu
            370                 375                 380

Pro Ala Ser Ile Glu Lys Thr Ile Ser Lys Ala Lys Gly Gln Pro Arg
385                 390                 395                 400
```

Glu Pro Gln Val Tyr Thr Leu Pro Pro Ser Arg Glu Met Thr Lys
                405                 410                 415

Asn Gln Val Ser Leu Thr Cys Leu Val Lys Gly Phe Tyr Pro Ser Asp
            420                 425                 430

Ile Ala Val Glu Trp Glu Ser Asn Gly Gln Pro Glu Asn Asn Tyr Lys
        435                 440                 445

Thr Thr Pro Pro Val Leu Asp Ser Asp Gly Ser Phe Phe Leu Tyr Ser
    450                 455                 460

Lys Leu Thr Val Asp Lys Ser Arg Trp Gln Gln Gly Asn Val Phe Ser
465                 470                 475                 480

Cys Ser Val Met His Glu Ala Leu His Asn His Tyr Thr Gln Lys Ser
                485                 490                 495

Leu Ser Leu Ser Pro Gly Lys Gly Gly Gly Gly Ser Gly Gly Gly Gly
            500                 505                 510

Ser Gly Gly Gly Gly Ser Gly Gly Gly Gly Ser Met Gly Trp Ser
            515                 520                 525

Ser Lys Pro Arg Gln Gly Met Gly Thr Asn Leu Ser Val Pro Asn Pro
    530                 535                 540

Leu Gly Phe Phe Pro Asp His Gln Leu Asp Pro Ala Phe Gly Ala Asn
545                 550                 555                 560

Ser Asn Asn Pro Asp Trp Asp Phe Asn Pro Asn Lys Asp His Trp Pro
                565                 570                 575

Glu Ala Asn Gln Val Gly Ala Gly Ala Phe Gly Pro Gly Phe Thr Pro
            580                 585                 590

Pro His Gly Gly Leu Leu Gly Trp Ser Pro Gln Ala Gln Gly Ile Leu
        595                 600                 605

Thr Thr Leu Pro Ala Ala Pro Pro Pro Ala Ser Thr Asn Arg Gln Ser
    610                 615                 620

Gly Arg Gln Pro Thr Pro Ile Ser Pro Pro Leu Arg Asp Ser His Pro
625                 630                 635                 640

Gln Ala Met Gln Trp Asn Ser Thr Thr Phe His Gln Ala Leu Leu Asp
                645                 650                 655

Pro Arg Val Arg Gly Leu Tyr Phe Pro Ala Gly Gly Ser Ser Ser Gly
            660                 665                 670

Thr Val Asn Pro Val Pro Thr Thr Ala Ser Pro Ile Ser Ser Ile Phe
        675                 680                 685

Ser Arg Thr Gly Asp Pro Ala Pro Asn His His His His His His
    690                 695                 700

<210> SEQ ID NO 68
<211> LENGTH: 2142
<212> TYPE: DNA
<213> ORGANISM: Artificial Sequence
<220> FEATURE:
<223> OTHER INFORMATION: G28-8scAb-preS1-S2-His

<400> SEQUENCE: 68
gcgaagcttt gagccaccat ggaaacccca gcgcagcttc tcttcctcct gctactctgg       60
ctcccagata ccaccggtga catccagatg actcagtctc cagcctccct atctgcatct      120
gtgggagaaa ctgtcaccat cacatgtcga gcaagtgaga gatttacag ttatttagca      180 tggtatcagc agaaacaggg aaaatctcct cagctcctgg tctataacgc aaaaacctta      240
gcagaaggtg tgccatcaag gttcagtgtc agtggatcag gcacacagtt ttctctgagg      300
atcaacagcc tgcagcctga agattttggg acttattact gtcaacatca ttttggttct      360

```
cctcggacgt tcggtggagg caccaaactg gaaatcaaag atctcggagg aggtggctca    420
ggtggtggag gatctggagg aggtgggagt ggtggaggtg gttctaccgg tgaggtccag    480
ctgcaacagt ctggacctga actggtgaag cctggagctt caatgaagat atcctgcaag    540
gcttctggtt actcattcac tggctacacc atgaactggg tgaagcagag ccatggaaag    600
acccttgaat ggattggact tattaatcct tacaatggtg ttactagcta caaccagaag    660
ttcaaggaca aggccacatt aactgtagac aagtcatcca gcacagccta catgaaactc    720
ctcagtctga catctgagga ctctgcaatc tattactgtg caagagacta taattacgac    780
tactttgact actggggcca aggcaccact ctcacagtct cctcagatct cgagcccaaa    840
tcttctgaca aaactcacac atgtccaccg tgtccagcac tgaactcctg ggtggatcg     900 tcagtcttcc tcttcccccc aaaacccaag gacactctca tgatctcccg gacccctgag    960
gtcacgtgcg tggtggtgga cgtgagccac gaagacccccg aggtcaagtt caactggtac   1020
gtggacggcg tggaggtgca taatgccaag acaaagccac gggaggagca gtacaacagc    1080
acgtaccgtg tggtcagcgt cctcaccgtc ttgcaccagg actggctgaa cggcaaggag    1140
tacaagtgct cggtctccaa caaagccctc ccagcctcca tcgagaaaac aatctccaaa    1200
gccaaagggc agccccgaga accacaggtg tacaccctgc ccccatcccg ggaggagatg    1260
accaagaacc aggtcagcct gacctgcctg gtcaaaggct tctatcccag cgacatcgcc    1320
gtggagtggg agagcaatgg gcagccggag aacaactaca agaccacgcc tcccgtgctg    1380
gactccgacg gctccttctt cctctacagc aagctcaccg tggacaagag caggtggcag    1440
caggggaacg tcttctcatg ctccgtgatg catgaggctc tgcacaacca ctacacgcag    1500
aagagcctct ctctgtctcc gggtaaagga ggaggtggct caggtggtgg aggatctgga    1560
ggaggtggga gtggtggagg tggttctatg ggaggttggt cttccaaacc tcgacaaggc    1620
atggggacga atctttctgt tcccaatcct ctgggattct ttcccgatca ccagttggac    1680
cctgcgttcg gagccaactc aaacaatcca gattgggact caaccccaa caaggatcac     1740 tggccagagg caaatcaggt aggagcggga gcatttggtc cagggttcac cccaccacac    1800
ggaggccttt tggggtggag ccctcaggct cagggcatat tgacaacact gccagcagca    1860
cctcctcctg cctccaccaa tcggcagtca ggaagacagc ctactcccat ctctccacct    1920
ctaagagaca gtcatcctca ggccatgcag tggaactcca caacattcca ccaagctctg    1980
ctagatccca gagtgagggg cctatatttt cctgctggtg gctccagttc cggaacagta    2040
aaccctgttc cgactactgc ctcacccata tcgtcaatct tctcgaggac tggggaccct    2100
gcaccgaacc accaccatca tcatcattga taaggatccg cg                      2142
```

<210> SEQ ID NO 69
<211> LENGTH: 20
<212> TYPE: PRT
<213> ORGANISM: Artificial Sequence
<220> FEATURE:
<223> OTHER INFORMATION: Gly-Ser linker

<400> SEQUENCE: 69

Gly Gly Gly Gly Ser Gly Gly Gly Gly Ser Gly Gly Gly Gly Ser Gly
1               5                   10                  15

Gly Gly Gly Ser
            20

THERAPEUTIC VACCINE FOR HEPATITIS B VIRUS (HBV) USING THE HBV PRES1 AND/OR PRES2, AND/OR S-HBSAG REGIONS OF THE HBV ENVELOPE PROTEIN

CROSS-REFERENCE

This application is a U.S. national phase of International Application No. PCT/US2018/061218, filed on Nov. 15, 2018, which claims priority to U.S. Provisional Application No. 62/587,051, filed Nov. 16, 2017, both of which are incorporated by reference herein in their entirety.

STATEMENT OF GOVERNMENT RIGHTS

This disclosure was made with government support under Grant No. HR0011-11-2-0007, awarded by the Defense Advanced Research Projects Agency. The government has certain rights in the disclosure.

BACKGROUND OF THE DISCLOSURE

In spite of the availability of prophylactic Hepatitis B virus (HBV) vaccines, HBV infection remains a very significant global health problem in both industrialized and developing nations; it is second only to tobacco as a cause of cancer. There is a clear unmet need for a therapeutic HBV vaccine for patients chronically infected with HBV (CHB). 10-30% of those vaccinated with marketed HBV vaccines do not respond either due to genetic factors, or non-compliance (failure to return for a series of 3 vaccinations). Only 37% of individuals vaccinated once with a licensed HBV vaccine are protected; even after three vaccinations, which are difficult to achieve, many people do not respond effectively. There is no effective vaccine for the 400 million people chronically infected with HBV, including asymptomatic HBV carriers. The drugs currently used to treat CHB patients are problematic. Sustained antiviral responses are rarely achieved and the currently available therapies can lead to viral resistance and produce side effects in many CHB patients.

DETAILED DESCRIPTION OF THE DISCLOSURE

Figure 1:
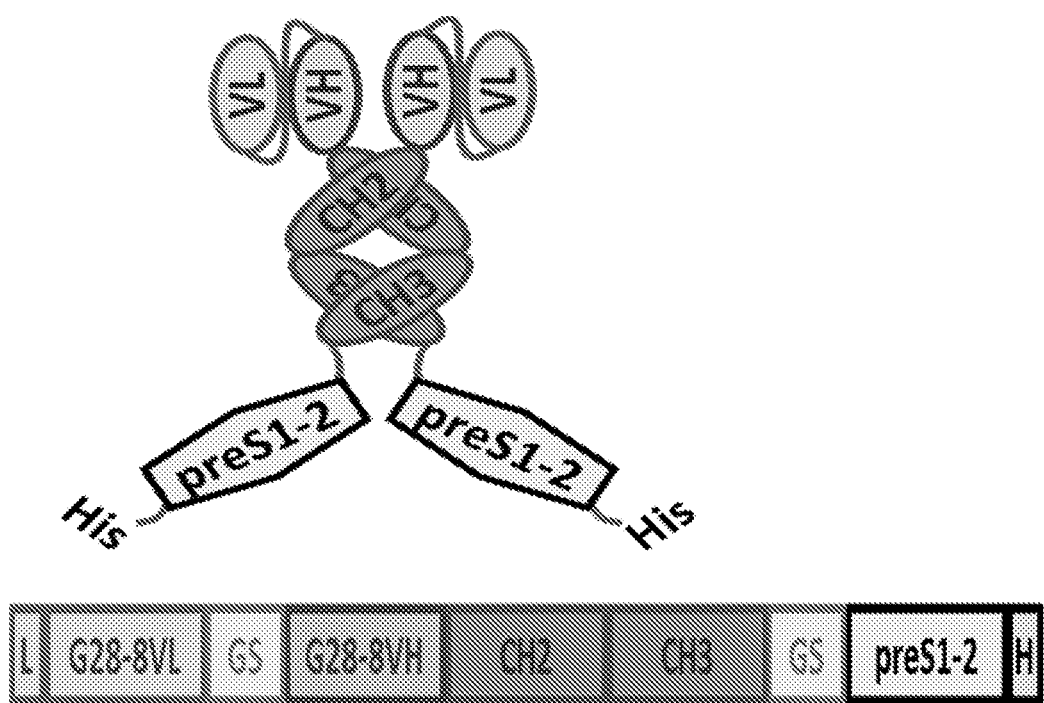
FIG. 1. Schematic design of the G28-8LH-scAb-PreS1-S2-His protein.

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide* to *Methods and Applications* (Innis, et al. 1990. Academic Press, San Diego, Calif.), *Culture of Animal Cells: A Manual of Basic Technique*, 2$^{nd}$ *Ed.* (R. I. Freshney. 1987. Liss, Inc. New York, N.Y.), *Gene Transfer and Expression Protocols,* pp. 109-128, ed. E. J. Murray, The Humana Press Inc., Clifton, N.J.), and the Ambion 1998 Catalog (Ambion, Austin, Tex.).

As used herein, the singular forms "a", "an" and "the" include plural referents unless the context clearly dictates otherwise. "And" as used herein is interchangeably used with "or" unless expressly stated otherwise.

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

All embodiments of any aspect of the disclosure can be used in combination, unless the context clearly dictates otherwise.

In a first aspect, the present disclosure provides compositions, comprising:

(a) a CD180 binding ligand; and (b) Hepatitis B virus pre-S1 and/or pre-S2 regions of the HBV envelope protein (HBVpreS1-S2Ag), S-HBsAg, or antigenic fragments or mutants thereof, attached to the CD180 binding ligand.

The compositions of the disclosure can be used, for example, to induce prophylactic responses in individuals at risk of HBV infection, and therapeutic responses in already infected individuals and in immunodeficient individuals who do not respond well to standard vaccines. The present disclosure is highly significant because it provides a therapeutic vaccine for one of the major causes of cancer and liver disease in the world: hepatitis B virus (HBV). HBV infection is a serious global public health problem in both industrialized and developing nations. 10-30 million people worldwide become infected with HBV each year, and more than 2 billion people worldwide have been infected with HBV. Significantly, the ability of unvaccinated individuals to mount effective immune responses against HBV is correlated with age. Infants and young children are particularly at risk, as 90% of infants and up to 50% of young children infected with HBV ultimately develop chronic infections. About 400 million are chronically infected with HBV (CHB), and in the USA there are approximately 1.4 million CHB infected people[5]. In the USA the prevalence of HBV while dropping in children, has changed little in adults[11] such that the burden of chronic hepatitis B among adults remains large[6]; in some groups it is as high as 1%. An estimated 1 million people die each year from hepatitis and its complications, including about 5,000 people in the US. Of the 5000 persons in the United States who die each year from HBV related conditions, 300 die from fulminant hepatitis; 3-4000, from cirrhosis; and 600-1000, from primary hepatocellular carcinoma (HCC). In the US, approximately 400 health care workers are infected each year and are at risk from dying from HBV-related disease[16].

The CD180 binding ligand may be any molecule that binds directly to CD180 present in the surface of B cells, macrophages, or dendritic cells. In various non-limiting embodiments, the CD180 binding ligand may be a peptide mimetic or an antibody.

In a particular embodiment, the CD180 binding ligand is an antibody or antibody fragment. As used herein, “antibody” includes reference to full length and functional fragments of any of the following: an immunoglobulin molecule immunologically reactive with human CD180 (preferably selective for CD180), genetically engineered forms such as chimeric antibodies (e.g., humanized murine antibodies) and heteroconjugate antibodies (e.g., bispecific antibodies), fully humanized antibodies, human antibodies, single chain Fv fragments (scFv), bivalent or bispecific molecules, diabodies, triabodies, and tetrabodies, single domain molecules such as VH and VL that are capable of specifically binding to an epitope of an antigen, and camelids. Fragments with antigen-binding activity include, but are not limited to, Fab', $F(ab')_2$, Fab, Fv and rIgG and includes monoclonal antibodies. Various isotypes of antibodies exist, for example IgG1, IgG2, IgG3, IgG4, and other Ig, e.g., IgM, IgA, IgE isotypes. The term also includes. Bivalent and bispecific molecules are described in, e.g., Kostelny et al. (1992) *J Immunol* 148:1547, Pack and Pluckthun (1992) *Biochemistry* 31:1579, Hollinger et al., 1993, supra, Gruber et al. (1994) *J Immunol:* 5368, Zhu et al. (1997) *Protein Sci* 6:781, Hu et al. (1996) *Cancer Res.* 56:3055, Adams et al. (1993) *Cancer Res.* 53:4026, and McCartney, et al. (1995) *Protein Eng.* 8:301. Various antigen binding domain-fusion proteins are also disclosed, e.g., in US patent application Nos. 2003/0118592 and 2003/0133939, and are encompassed within the term “antibody” as used in this application.

An antibody immunologically reactive with human CD180 can be generated by recombinant methods such as selection of libraries of recombinant antibodies in phage or similar vectors, see, e.g., Huse et al., *Science* 246:1275-1281 (1989); Ward et al., *Nature* 341:544-546 (1989); and Vaughan et al., *Nature Biotech.* 14:309-314 (1996), or by immunizing an animal with the antigen or with DNA encoding the antigen.

In one embodiment, the CD180 binding ligand comprises a single chain (sc) recombinant protein, wherein the sc recombinant protein comprises:

(i) a variable heavy (VH) chain region of an anti-CD180 antibody; and (ii) a variable light (VL) chain region of an anti-CD180 antibody.

In one embodiment, the CD180 binding ligand comprises a single domain (sd) recombinant protein, wherein the sd recombinant protein comprises a variable heavy (VHH) chain region of an anti-CD180 antibody derived from a camelid species.

The VH and VL chain regions may be from an anti-human CD180 antibody, such as an anti-human CD180 monoclonal antibody. Exemplary commercially available CD180 anti-human monoclonal antibodies from which the VH and VL chains may be used include, but are not limited to, those sold by AbD Serotec™ (“MHR73-11”), BD Biosciences, Thermo Scientific, Sigma Aldrich, etc.), (“G28-8”), and LifeSpan™ (“200.1”). In one embodiment, the single chain recombinant protein does not include any other immunoglobulin domains (i.e.: a single chain variable fragment (scFv)). In an alternative embodiment, the single chain recombinant protein further comprises: CH2 and CH3 domains from an immunoglobulin (Ig), such as a human Ig, or functional mutants thereof, wherein the CH2 and CH3 domains are located C-terminal to the VH and VL domains. The CH2 and CH3 domains may be from any immunoglobulin as deemed appropriate for an intended use of the composition, including but not limited to IgA1, IgA2, IgG1, IgG2, IgG3, IgG4, IgM, etc. In a particular embodiment, the sc recombinant protein comprises CH2 and CH3 domains from IgG1, such as human IgG1, or functional mutants thereof. In a particular embodiment, such "functional mutants" comprise CH2 and/or CH3 domains that have impaired binding to human or animal Fc receptor FcγRIIb and/or to human or animal complement proteins (J Biol Chem 276: 6591-6604). The Fc domain of the recombinant molecules is an altered human IgG1 Fc domain with three amino acid changes (P238S, P331S, K322S) that reduce the binding of the molecule to Fc receptors and C1q. Other amino acid substitutions that can reduce binding of human IgG1 to various Fc receptors include but are not limited to E233P, L234V, L235A, G236 deletion, P238A, D265A, N297A, A327Q, and P329A. Substitutions at these amino acids reduce binding to all FcγR. Substitutions at D270A, Q295A, or A327S reduce binding to FcγRII and FcγRIIIA. Substitutions at S239A, E269A, E293A, Y296F, V303A, A327G, K338A, and D376A reduce binding to FcγRIIIA but not FcγRII. A combination of two of more of these substitutions can be engineered in the Fc domains of human IgG1 to achieve the desired effects on inhibiting Fc-FcγR interaction between CD180 targeted vaccines and FcgR expressing cells. Similarly, modifying the glycosylation profile of human IgG1, for example, substit -continued L-HBsAg
(SEQ ID NO: 4)
MGGWSSKPRQ GMGTNLSVPN PLGFFPDHQL DPAFGANSNN PDWDFNPNKD HWPEANQVGA

GAFGPGFTPP HGGLLGWSPQ AQGILTTLPA APPPASTNRQ SGRQPTPISP PLRDSHPQAM

QWNSTTFHQA LLDPRVRGLY FPAGGSSSGT VNPVPTTASP ISSIFSRTGD PAPNMESTTS

GFLGPLLVLQ AGFFLLTRIL TIPQSLDSWW TSLNFLGGAP TCPGQNSQSP TSNHSPTSCP

PTCPGYRWMC LRRFIIFLFI LLLCLIFLLV LLDYQGMLPV CPLLPGTSIT STGPCRTCTI

PAQGTSMFPS CCCTKPSDGN CTCIPIPSSW AFARFLWEWA SVRFSWLSLL VPFVQWFVGL

SPTVWLSAIW MMWYWGPSLY NILSPFLPLL PIFFCLWVYI

M-HBsAg
(SEQ ID NO: 5)
PPLRDSHPQA MQWNSTTFHQ ALLDPRVRGL YFPAGGSSSG TVNPVPTTAS PISSIFSRTG

DPAPNMESTT SGFLGPLLVL QAGFFLLTRI LTIPQSLDSW WTSLNFLGGA PTCPGQNSQS

PTSNHSPTSC PPTCPGYRWM CLRRFIIFLF ILLLCLIFLL VLLDYQGMLP VCPLLPGTST

TSTGPCRTCT IPAQGTSMFP SCCCTKPSDG NCTCIPIPSS WAFARFLWEW ASVRFSWLSL

LVPFVQWFVG LSPTVWLSAI WMMWYWGPSL YNILSPFLPL LPIFFCLWVY I

S-HBsAg
(SEQ ID NO: 6)
MESTTSGFLG PLLVLQAGFF LLTRILTIPQ SLDSWWTSLN FLGGAPTCPG QNSQSPTSNH

SPTSCPPTCP GYRWMCLRRF IIFLFILLLC LIFLVLLDY QGMLPVCPLL PGTSTTSTGP

CRTCTIPAQG TSMFPSCCCT KPSDGNCTCI PIPSSWAFAR FLWEWASVRF SWLSLLVPFV

QWFVGLSPIV WLSAIWMMWY WGPSLYNILS PFLPLLPIFF CLWVYI

P31873 Hepatitis B virus genotype A1 subtype adw2 (isolate Southern-
Africa/Cai)
PreS1
(SEQ ID NO: 7)
MGGWSAKPRKGMGTNLSVPNPLGFFPDHQLDPAFGANSNNPDWDFNPNKDHWPEANQVGVGAFGPGFT

PPHGGLLGWSSQAQGTLHTVPAVPPPASTNRQTGRQPTPI

PreS2
(SEQ ID NO: 8)
SPPLRDSHPQAMQWNSTAFQQALQDPRVRGLFFPAGGSSSGTVNPAPNIASHISS

S-HBsAg
(SEQ ID NO: 9)
ISSRTGDPALNMENITSGFLGPLLVLQAGFFLLTRILTIPQSLDSWWTSLNFLGGSPVCLGQNSQSPT

SNHSPTSCPPICPGYRWMCLRRFIIFLFILLLCLIFLLVLLDYQGMLPVCPLIPGSTTTSTGPCKTCT

TPAQGNSMFPCCCTKPTDGNCTCIPIPSSWAFAKYLWEWASVRFSWLSLLVPFVQWFVGLSPTVWLSV

IWMMWYWGPSLYNILSPFIPLLPIFFCLWVYI

M-HBsAg
(SEQ ID NO: 10)
SPPLRDSHPQAMQWNSTAFQQALQDPRVRGLFFPAGGSSSGTVNPAPNIASHISSISSRTGDPALNME

NITSGFLGPLLVLQAGFFLLTRILTIPQSLDSWWISLNFLGGSPVCLGQNSQSPISNHSPISCPPICP

GYRWMCLRRFIIFLFILLLCLIFLLVLLDYQGMLPVCPLIPGSTTTSTGPCKICTTPAQGNSMFPCCC

TKPTDGNCTCIPIPSSWAFAKYLWEWASVRFSWLSLLVPFVQWFVGLSPTVWLSVIWMMWYWGPSLYN

ILSPFIPLLPIFFCLWVYI

L-HBsAg
(SEQ ID NO: 11)
MGGWSAKPRKGMGTNLSVPNPLGFFPDHQLDPAFGANSNNPDWDFNPNKDHWPEANQVGVGAFGPGFT

PPHGGLLGWSSQAQGTLETVPAVPPPASTNRQTGRQPTPISPPLRDSHPQAMQWNSTAFQQALQDPRV

RGLFFPAGGSSSGTVNPAPNIASHISSISSRTGDPALNMENITSGFLGPLLVLQAGFFLLTRILTIPQ

-continued

SLDSWWTSLNFLGGSPVCLGQNSQSPTSNHSPTSCPPICPGYRWMCLRRFIIFLFILLLCLIFLLVLL

DYQGMLPVCPLIPGSTTTSTGPCKTCTTPAQGNSMFPSCCCTKPTDGNCTCIPIPSSWAFAKYLWEWA

SVRFSWLSLLVPFVQWFVGLSPTVWLSVIWMMWYWGPSLYNILSPFIPLLPIRFCLWVYI

P03141 Hepatitis B virus genotype A2 subtype adw2 (strain Rutter
1979)
PreS1
(SEQ ID NO: 12)
MGGWSSKPRKGMGTNLSVPNPLGFFPDHQLDPAFGANSNNPDWDFNPVKDDWPAANQVGVGAFGPRLT

PPHGGILGWSPQAQGILTTVSTIPPPASTNRQSGRQPTPI

PreS2
(SEQ ID NO: 13)
SPPLRDSHPQAMQWNSTAFHQTLQDPRVRGLYLPAGGSSSGTVNPAPNIASHISS

S-HBsAg
(SEQ ID NO: 14)
ISARTGDPVTNMENITSGFLGPLLVLQAGFFLLTRILTIPQSLDSWWTSLNFLGGSPVCLGQNSQSPT

SNHSPTSCPPICPGYRWMCLRRFIIFLFILLLCLIFLLVLLDYQGMLPVCPLIPGSTTTSTGPCKTCT

TPAQGNSMFPSCCCTKPTDGNCTCIPIPSSWAFAKYLTREWASVRFSWLSLLVPFVQWFVGLSPTVWLS

AIWMMWYWGPSLYSIVSPFIPLLPIFFCLWVYI

M-HBsAG
(SEQ ID NO: 15)
SPPLRDSHPQAMQWNSTAFHQTLQDPRVRGLYLPAGGSSSGTVNPAPNIASHISSISARTGDPVTNME

NITSGFLGPLLVLQAGEFLLTRILTIPQSLDSWWTSLNFLGGSPVCLGQNSQSFTSNHSPTSCPPICP

GYRWMCLRRFIIFLFILLLCLIFLLVLLDYQGMLPVCPLIPGSTTTSTGPCKTCTTPAQGNSMFPSCC

CTKPTDGNCTCIPIPSSWAFAKYLWEWASVRFSWLSLLVPFVQWFVGLSPTVWLSAIWMMWYWGPSLY

SIVSPFIPLLPIFFCLWVYI

L-HBsAg
(SEQ ID NO: 16)
MGGWSSKPRKGMGTNLSVPNPLGFFPDHQLDPAFGANSNNPDWDFNPVKDDWPAANQVGVGAFGPRLT

PPHGGILGWSPQAQGILTTVSTIPPPASTNRQSGRQPTPISPPLRDSHPQAMQWNSTAFHQTLQDPRV

RGLYLPAGGSSSGTVNPAPNIASHISSISARTGDPVTNMENITSGFLGPLLVLQAGFFLLTRILTIPQ

SLDSWWTSLNFLGGSPVCLGQNSQSPTSNHSPTSCPPICPGYRWMCLRRFIIFLFILLLCLIFLLVLL

DYQGMLPVCPLIPGSTTTSTGPCKTCTTPAQGNSMFPSCCCTKPTDGNCTCIPIPSSWAFAKYLWEWA

SVRFSWLSLLVPFVQWFVGLSPTVWLSAIWMMWYWGPSLYSIVSPFIPLLPIFFCLWVYI

Q4R1R8 Hepatitis B virus genotype A3 (isolate Cameroon/CMR711/1994)
PreS1
(SEQ ID NO: 17)
MGGRLPKPRKGMGTNLSVPNPLGFFPDHQLDPAFGANSNNPDWDFNPIKDHWPQANQVGVGAFGPGFT

PPHGGVLGWSPQAQGTLTTVPAVPPPASTNRQSGRQPTPI

PreS2
(SEQ ID NO: 18)
SPPLRDSHPQAMQWNSTKFHQTLQDPRVRGLYFPAGGSSSGTVNPAPNIASHISS

S-HBsAg
(SEQ ID NO: 19)
ISSRIGDPAPTMENITSGFLGPLLVLQAGFFLLTRILTIPQSLDSWWTSLNFLGEAPVCLGQNSQSPT

SNHSPTSCPPICPGYRWMCLRRFIIFLFILLLCLIFLLVLLDCQGMLPVCPLIPGSTTTSTGPCRTCT

TPAQGNSMFPSCCCTKPTDGNCTCIPIPSSWAFAKYLWEWASVRFSWLSLLVPFVQWFVGLSPTVWLS

VIWMMWYWGPSLYNILSPFIPLLPIFFCLWVYI

M-HBsAg
(SEQ ID NO: 20)
SPPLRDSHPQAMQWNSTKEHQTLQDPRVRGLYFPAGGSSSGTVNPAPNIASHISSISSRIGDPAPTME

NITSGFLGPLLVLQAGFFLLTRILTIPQSLDSWWTSLNFLGEAPVCLGQNSQSPTSNHSPTSCPPICP

```
GYRWMCLRRFIIFLFILLLCLIFLLVLLDCQGMLPVCPLIPGSTTTSTGPCRTCTTPAQGNSMFPSCC

CTKPTDGNCTCIPIPSSWAFAKYLWEWASVRFSWLSLLVPFVQWFVGLSPTVWLSVIWMMWYWGPSLY

NILSPFIPLLPIFFCLWVYI
```

L-HBsAg
```
                                                          (SEQ ID NO: 21)
MGGRLFKPRKGMGTNLSVPNPLGEFFDHQLDPAFGANSNNFDWDFNPIKDHWPQANQVGVGAFGPGFT

PPHGGVLGWSPQAQGTLTTVPAVPPPASTNRQSGRQPTPISPPLRDSHPQAMQWNSTKFHQTLQDPRV

RGLYFPAGGSSSGTVNPAPNIASHISSISSRIGDPAPTMENITSGFLGPLLVLQAGEFLLTRILTIPQ

SLDSWWTSLNELGEAPVCLGQNSQSPTSNHSPTSCPPICPGYRWMCLRRFIIFLFILLLCLIFLLVLL

DCQGMLPVCPLIPGSTTTSTGPCRTCTTPAQGNSMFPSCCCTKPTDGNCTCIPIPSSWAFAKYLWEWA

SVRFSWLSLLVPFVQWFVGLSPTVWLSVIWMMWYWGPSLYNILSPFIPLLPIFFCLWVYI
```

Q8JXB9 Hepatitis B virus genotype B1 (isolate Japan/Ry30/2002)
PreS1
```
                                                          (SEQ ID NO: 22)
MGGWSSKPRKGMGTNLSVPNPLGFFPDHQLDPAFKANSENPDWDLNPHKDNWPDAHKVGVGAFGPGFT

PPHGGLLGWSPQAQGILTSVPAAPPPASTNRQSGRQPTPL
```

PreS2
```
                                                          (SEQ ID NO: 23)
SPPLRDTHPQAMQWNSTTFHQTLQDPRVRALYLPAGGSSSGTVSPAQNTVSAISS
```

S-HBsAG
```
                                                          (SEQ ID NO: 24)
ILSTTGDPVPNMENIASGLLGPLLVLQAGFFSLTKILTIPQOLDSWWTSLSFLGGTPVCLGQNSQSPI

SSHSPTCCPPICPGYRWMYLRRFIIXLCILLLCLIFLLVLLDYQGMLPVCPLIPGSSTTSTGPCKTCT

TPAQGTSMFPSCCCTKPTDGNCTCIPIPSSWAFAKYLWEWASVRFSWLSLLVPFVQWFVGLSPTVWLS

VIWMMWYWGPSLYNILSPFMPLLPIFFCLWVYI
```

M-HBsAg
```
                                                          (SEQ ID NO: 25)
SPPLRDTHPQAMQWNSTTFHQTLQDPRVRALYLPAGGSSSGTVSPAQNTVSAISSILSTTGDPVPNME

NIASGLLGPLLVLQAGFFSLTKILTIPQSLDSWWTSLSFLGGTPVCLGQNSQSPISSHSPTCCPPICP

GYRWMYLRRFIIXLCILLLCLIFLLVLLDYQGMLPVCPLIPGSSTTSTGPCKTCTTPAQGTSMFPSCC

CTKPTDGNCTCIPIPSSWAFAKYIMEWASVRFSWLSLLVPFVQWFVGLSPTVWLSVIWMMWYWGPSLY

NILSPFMPLLPIFFCLWVYI
```

L-HBsAg
```
                                                          (SEQ ID NO: 26)
MGGWSSKPRKGMGTNLSVPNPLGFFPDHQLDPAFKANSENPDWDLNPHKDNWPDAHKVGVGAFGPGFT

PPHGGLLGWSPQAQGILTSVPAAPPPASTNRQSGRQPTPLSPPLRDTHPQAMQWNSTTFHQTLQDPRV

RALYLPAGGSSSGTVSPAQNTVSAISSILSTTGDPVPNMENIASGLLGPLLVLQAGFFSLTKILTIPQ

SLDSWWTSLSFLGGTPVCLGQNSQSPISSHSPTCCPPICPGYRWMYLRRFIIXLCILLLCLIFLLVLL

DYQGMLPVCPLIPGSSTTSTGPCKTCTTPAQGTSMFPSCCCTKPTDGNCTCIPIPSSWAFAKYLWEWA

SVRFSWLSLLVPFVQWFVGLSPTVWLSVIWMMWYWGPSLYNILSPFMPLLPIFFCLWVYI
```

Q9PWW3 Hepatitis B virus genotype B2 (isolate Vietnam/16091/1992)
PreS1
```
                                                          (SEQ ID NO: 27)
MGGWSSKPRKGMGTNLSVPNPLGFFPDHQLDPAFKANSENPDWDLNPHKDNWPDANKVGVGAFGPGFT

PPHGGLLGWSPQAQGLLTTVPAAPPPASTNRQSGRQPTPL
```

PreS2
```
                                                          (SEQ ID NO: 28)
SPPLRDTHPQAMQWNSTTFHQTLQDPRVRALYFPAGGSSSGTVSPAQNTVSTISS
```

S-HBsAg
(SEQ ID NO: 29)
ILSKTGDPVPNMENIASGLLGPLLVLQAGFFLLTKILTIPQSLDSWWTSLNFLGGTPVCLGQNSQSQI

SSHSPTCCPPICPGYRWMCLRRFIIFLCILLLCLIFLLVLLDYQGMLPVCPLIPGSSTTSTGPCKTCT

TPAQGTSMFPSCCCTKPTDGNCTCIPIPSSWAFAKYLWEWASVRFSWLSLLVPFVQWFVGLSPTVWLS

VIWMMWFWGPSLYNILSPFMPLLPIFFCLWVYI

M-HBsAg
(SEQ ID NC: 30)
SPPLRDTHPQAMQWNSTTFHQTLQDPRVRALYFPAGGSSSGTVSPAQNTVSTISSILSKTGDPVPNME

NIASGLLGPLLVLQAGFFLLTKILTIPQSLDSWWTSLNFLGGTPVCLGQNSQSQISSHSPTCCPPICP

GYRWMCLRRFIIFLCILLLCLIFLLVLLDYQGMLPVCPLIPGSSTTSTGPCKTCTTPAQGTSMFPSCC

CTKPTDGNCTCIPIPSSWAFAKYLWEWASVRFSWLSLLVPFVQWFVGLSPTVWLSVIWMMWFWGPSLY

NILSPFMPLLPIFFCLWVYI

L-HBsAg
(SEQ ID NO: 31)
MGGWSSKPRKGMGTNLSVPNPLGFFPDHQLDPAFKANSENPDWDLNPHKDNWPDANKVGVGAFGPGFT

PPHGGLLGWSPQAQGLLTTVPAAPPPASTNRQSGRQPTPLSPPLRDTHPQAMQWNSTTFHQTLQDPRV

RALYFPAGGSSSGTVSPAQNTVSTISSILSKTGDPVPNMENIASGLLGPLLVLQAGFFLLTKILTIPQ

SLDSWWTSLNFLGGTPVCLGQNSQSQISSHSPTCCPPICPGYRWMCLRRFIIFLCILLLCLIFLLVLL

DYQGMLPVCPLIPGSSTTSTGPCKTCTTPAQGTSMFPSCCCTKPTDGNCTCIPIPSSWAFAKYLWEWA

SVRFSWLSLLVPFVQWFVGLSPTVIWLSVIWMMWFWGPSLYNILSPFMPLLPIFFCLWVYI

Q76R62 Hepatitis B virus genotype C subtype ayr (isolate
Human/Japan/Okamoto/-)
PreS1
(SEQ ID NO: 32)
MGGWSSKPRQGMGTNLSVPNPLGFFPDHQLDPAFGANSNNPDWDENPNKDHWPEANQVGAGAFGPGFT

PPHGGLLGWSPQAQGILITLPAAPPPASTNRQSGRQPTPI

PreS2
(SEQ ID NO: 33)
SPPLRDSHPQAMQWNSTIFHQALLDPRVRGLYFPAGGSSSGTVNPVPITASPISS

S-HBsAg
(SEQ ID NO: 34)
IFSRTGDPAPNMESTTSGELGPLLVLQAGFELLTRILTIPQSLESWWTSLNFLGGAPTCPGQNSQSPT

SNHSPISCPPTCPGYRWMCLRRFIIFLFILLLCLTFLLVLLDYQGMLPVCPLLPGISITSTGPCRICT

IPAQGISMDPSCCCTKPSDGNCICIPIPSSWAFARFLIREWASVRFSWLSLLVPFVQWEVGLSPTVWLS

AIWMMWYWGPSLYNILSPFLPLLPIFFCLWVYI

M-HBsAg
(SEQ ID NO: 35)
SPPLRDSHPQAMQWNSTTFHQALLDPRVRGLYFPAGGSSSGTVNPVPTTASPISSIFSRTGDPAPNME

STTSGFLGPLLVLQAGFFLLTRILTIPQSLDSWWTSLNFLGGAPTCPGQNSQSPTSNHSPTSCPPTCP

GYRWMCLRRFIIFLFLLLCLIFLLVLLDYQGMLPVCPLLPGTSTTSTGPCRTCTIPAQGTSMFPSCC

CTKPSDGNCTCIPIPSSWAFARFLWEWASVRFSWLSLLVPFVQWFVGLSPTVWLSAIWMMWYWGPSLY

NILSPFLPLLPIFFCLWVYI

L-HBsAg
(SEQ ID NO: 36)
MGGWSSKPRQGMGTNLSVPNPLGETPDHQLDPAFGANSNNPDWDENPNKDHWPEANQVGAGAFGPGFT

PPHGGLLGWSPQAQGILTTLPAAPPPASTNRQGRQPTPISPPLRDSHPQAMQWNSTIFHQALLDPRV

RGLYFPAGGSSSGTVNPVPTTASPISSIFSRTGDPAPNMESTTSGFLGPLLVLQAGFFLLTRILTIPQ

SLDSWWTSLNFLGGAPTCPGQNSQSPTSNESPTSCPPTCPGYRWMCLRRFIIFLFILLLCLIFLLVLL

-continued

DYQGMLPVCPLLPGTSTTSTGPCRTCTIPAQGTSMFPSCCCTKPSDGNCTCIPIPSSWAFARFLWEWA

SVRFSWLSLLVPFVQWFVGLSPTVWLSAIWMMWYWGPSLYNILSPFLPLLPIFFCLWVYI

P03138 Hepatitis B virus genotype D subtype ayw (isolate
France/Tiollais/1979)
PreS1

(SEQ ID NO: 37)

MGQNLSTSNPLGFFPDHQLDPAFRANTANPDWDFNPNKDTWPDANKVGAGAFGLGFTPPHGGLLGWSP

QAQGILQTLPANPPPASTNRQSGRQPTPL

PreS2

(SEQ ID NO: 38)

SPPLRNTHPQAMQWNSTTFHQTLQDPRVRGLYFPAGGSSSGTVNPVLITASPLSS

S-HBsAg (SEQ ID NO: 39)

IFSRIGDPALNMENITSGFLGPLLVLQAGFFLLTRILTIPQSLDSWWTSLNFLGGTTVCLGQNSQSPT

SNHSPTSCPPTCPGYRWMCLRRFIIFLFILLLCLIFLLVLLDYQGMLPVCPLIPGSSITSTGPCRTCM

TTAQGTSMYPSCCCTKPSDGNCTCIPIPSSWAFGKFLTREWASARFSWLSLLVPFVQWFVGLSPTVWLS

VIWMMWYWGPSLYSILSPFLPLLPIFFCLWVYI

M-HBsAg (SEQ ID NO: 40)

SPPLRNTHPQAMQWNSTTFHQTLQDPRVRGLYFPAGGSSSGTVNPVLTTASPLSSIFSRIGDPALNME

NITSGFLGPLLVLQAGFFLLTRILTIPQSLDSWWTSLNFLGGTTVCLGQNSQSPTSNHSPTSCPPTCP

GYRWMCLRRFIIFLFILLLCLIFLINLLDYQGMLPVCPLIPGSSTTSTGPCRTCMTTAQGTSMYPSCC

CTKPSDGNCTCIPIPSSWAFGKFLWEWASARFSWLSLLVPFVQWFVGLSPTVWLSVIWMMWYWGPSLY

SILSPFLPLLPIFFCLWVYI

L-HBsAg (SEQ ID NO: 41)

MGQNLSTSNPLGFFPDHQLDPAFRANTANPDWDFNPNKDTWPDANKVGAGAFGLGFTPPHGGLLGWSP

QAQGILQTLPANPPPASTNRQSGRQPTPLSPPLRNTHPQAMQWNSTTFHQTLQDPRVRGLYFPAGGSS

SGTVNPVLTTASPLSSIFSRIGDPALNMENITSGFLGPLLVLQAGFFLLTRILTIPQSLDSWWTSLNF

LGGTTVCLGQNSQSPTSNHSPTSCPPTCPGYRWMCLRRFIIFLFILLLCLIFLLVLLDYQGMLPVCPL

IPGSSTTSTGPCRTCMTTAQGTSMYPSCCCTKPSDGNCTCIPIPSSWAFGKFLWEWASARFSWLSLLV

PFVQWFVGLSPTVWLSVIWMMWYWGPSLYSILSPFLPLLPIFFCLWVYI

Q69603 Hepatitis B virus genotype E subtype ayw4 (isolate Kou)
GN = S PE = 1 SV = 2
PreS1

(SEQ ID NO: 42)

MGLSWTVPLEWGKNISTTNPLGFFPDHQLDPAFRANTRNPDWDHNPNKDHWTEANKVGVGAFGPGFTP

PHGGLLGWSPQAQGMLKTLPADPPPASTNRQSGRQPTPI

PreS2

(SEQ ID NO: 43)

TPPLRDTHPQAMQWNSTTFHQALQDPRVRGLYFPAGGSSSGTVNPVPTTASLISS

S-HBsAg (SEQ ID NC: 44)

IFSRIGDPAPNMESITSGFLGPLLVLQAGFFLLTKILTIPQSLDSWWTSLNFLGGAPVCLGQNSQSPT

SNHSPTSCPPICPGYRWMCLRRFIIFLFILLLCLIFLLVLLDYQGMLPVCPLIPGSSTTSTGPCRTCM

TLAQGTSMFPSCCCSKPSDQNCTCIPIPSSWAEGKFLWEWASARFSWLSLLVPFVQWFAGLSPTVWLS

VIWMMWYWGPSLYDILSPFTPPLPIFFCLWVYI

M-HBsAg (SEQ ID NO: 45)

TPPLRDTHPQAMQWNSITFHQALQDPRVRGLYFPAGGSSSGTVNPVPTTASLISSIFSRIGDPAPNME

SITSGFLGPLLVLQAGFFLLTKILTIPQSLDSWWTSLNFLGGAPVCLGQNSQSPTSNHSPTSCPPICP

GYRWMCLRRFIIFLFILLLCLIFLLVLLDYQGMLPVCPLIPGSSTTSTGPCRTCMTLAQGTSMFPSCC

-continued

```
CSKPSDGNCTCIPIPSSWAFGKFLWEWASARESWLSLLVPFVQWFAGLSPTVWLSVIWMMWYWGPSLY

DILSPFIPLLPIFFCLWVYI

L-HBsAg
                                                              (SEQ ID NO: 46)
MGLSWTVPLEWGKNISTTNPLGFFPDHQLDPAFRANTRNPDWDHNPNKDHWTEANKVGVGAFGPGFTP

PHGGLLGWSPQAQGMLKTLPADPPPASTNRQSGRQPTPITPPLRDTHPQAMQWNSTTFHQALQDPRVR

GLYFPAGGSSSGTVNPVPTTASLISSIFSRIGDPAPNMESITSGFLGPLLVPQAGFFLLTKILTIPQS

LDSWWTSLNELGGAPVCLGQNSQSPTSNHSPTSCPPICPGYRWMCLRRFIIFLFILLLCLIFLLVLLD

YQGMLPVCPLIPGSSTTSTGPCRTCMTLAQGTSMEPSCCCSKPSDGNCICIPIPSSWAFGKFLWEWAS

ARFSWLSLLVPFVQWFAGLSPTVWLSVIWMMWYWGPSLYDILSPFIPLLPIFFCLWVYI

Q99HS3 Hepatitis B virus genotype F1 (isolate Argentina/sa11/2000)
PreS1
                                                              (SEQ ID NO: 47)
MGAPLSTTRRGMGQNLSVPNPLGFFPDHQLDPLFRANSSSPDWDENKNKDNWPMANKVGVGGYGPGFT

PPHGGLLGWSPQAQGVLTTLPADPPPASTNRRSGRKPTPV

PreS2
                                                              (SEQ ID NO: 48)
SPPLRDTHPQAMQWNSTQFHQALLDPRVRALYFPAGGSSSETQNPAPTIASLTSS

S-HBsAg
                                                              (SEQ ID NO: 49)
IFLKTGGPATNMDNITSGLEGPLLVLQAVCELLTKILTIPQSLDSWWTSENFLGGTPGCPGQNSQSPT

SNHLPTSCPPTCPGYRWMCERRFIIFLFILLLCLIFLLVLVDYQGMLPVCPPLPGSTTTSTGPCKTCT

TLAQGTSMFPSCCCSKPSDGNCTCIPIPSSWALGKYLWEWASARFSWLSLLVQFVQWCVGLSPTVWLL

VIWMIWYWGPNLCSILSPFIPLLPIFCYLWVSI

M-HBsAg
                                                              (SEQ ID NO: 50)
SPPLRDTHPQAMQWNSTQFHQALLDPRVRALYFPAGGSSSETQNPAPTIASLTSSIFLKTGGPATNMD

NITSGLLGPLLVLQAVOELLTKILTIPQSLDSWWTSLNFLGGTPGCPGQNSQSPTSNHLPTSCPPTCP

GYRWMCLRRFIIFLFILLLCLIFLLVLVDYQGMLPVCPPLPGSTTTSTGPCKTCTTLAQGTSMFPSCC

CSKPSDGNCTCIPIPSSWALGKYLWEWASARFSWLSLLVQFVQWCVGLSPTVWLLVIWMIWYWQPNLC

SILSPFIPLLPIFCYLWVSI

L-HBsAg
                                                              (SEQ ID NO: 51)
MGAPLSTTRRGMGQNLSVPNPLGFFPDHQLDPLFRANSSSPDWDFNKNKDNWPMANKVGVGGYGPGFT

PPHGGLLGWSPQAQGVLTTLPADPPPASTNRRSGRKPTPVSPPLRDTHPQAMQWNSTQFHQALLDPRV

RALYFPAGGSSSETQNPAPTIASLTSSIFLKTGGPATNMDNITSGLLGPLLVLQAVCFLLTKILTIPQ

SLDSWWTSLNFLGGTPGCPGQNSQSPTSNHLPTSCPPTCPGYRWMCLRRFIIFLFILLLCLIFLLVLV

DYQGMLPVCPPLPGSTTTSTGPCKTCTTLAQGTSMFPSCCCSKPSDGNCTCIPIPSSWALGKYLWEWA

SARFSWLSLLVQFVQWCVGLSPTVWLLVIWMIWYWGPNLCSILSPFIPLLPIFCYLWVSI

Q99HR4 Hepatitis B virus genotype F2 (isolate Argentina/sa16/2000)
PreS1
                                                              (SEQ ID NO: 52)
MGAPLSTTRRGMGQNLSVPNPLGFFPEHQLDPLFRANSSSPDWDFNKNKDTWPMANKVGVGGYGPGFT

PPHGGLLGWSPQAQGVLTTLPADPPPASTNRRSGRKPTPV

PreS2
                                                              (SEQ ID NO: 53)
SPPLRDTHPQAMQWNSTQFHQALLDPRVRALYFPAGGSSSETQNPAPTIASLTSS
```

S-HBsAg
(SEQ ID NO: 54)
IFSKTGGPAMNMDSITSGLLGPLINLQAVCFLLTKILTIPQSLDSWWTSLNFLGGLPGCPGQNSQSPT

SNHLPTSCPPTCPGYRWMCLRRFIIFLFILLLCLIFLLVLLDYQGMLPVCPLIPGSTTTSTGPCKTCT

TLAQGTSMFPSCCCSKPSDGNCTCIPIPSSWALGKYLWEWASARFSWLSLLVQFVQWCVGLSPTVWLL

VIWMIWYWGPNLCSILSPFIPLLPIFCYLWVSI

M-HBsAg
(SEQ ID NO: 55)
SPPLRDTHPQAMQWNSTQFHQALLDPRVRALYFPAGGSSSETQNPAPTIASLTSSIFSKTGGPAMNMD

SITSGLLGPLLVLQAVCFLLTKILTIPQSLDSWWTSLNFLGGLPGCPGQNSQSPTSNHLPTSCPPTCP

GYRWMCLRRFIIFLFILLLCLIFLLVLLDYQGMLPVCPLIPGSTTTSTGPCKTCTTLAQGTSMFPSCC

CSKPSDGNCTCIPIPSSWALGKYLWEWASARFSWLSLLVQFVQWCVGLSPTVWLLVIWMIWYWGPNLC

SILSPFIPLLPIFCYLWVSI

L-HBsAg
(SEQ ID NO: 56)
MGAPLSTTRRGMGQNLSVPNPLGFFPEHQLDPLFRANSSSPDWDENKNKDTWPMANKVGVGGYGPGFT

PPHGGLLGWSPQAQGVLTTLPADPPPASTNRRSGRKPTPVSPPLRDTHPQAMQWNSTQFHQALLDPRV

RALYFPAGGSSSETQNPAPTIASLTSSIFSKTGGPAMNMDSITSGLLGPLLVLQAVCFLLTKILTIPQ

SLDSWWTSLNFLGGLPGCPGQNSQSPTSNHLPTSCPPTCPGYRWMCLRRFIIFLFILLLCLIFLLVLL

DYQGMLPVCPLIPGSTTTSTGPCKTCTTLAQGTSMFPSCCCSKPSDGNCTCIPIPSSWALGKYLWEWA

SARFSWLSLLVQFVQWCVGLSPTVWLLVIWMIWYWGPNLCSILSPFIPLLPIFCYLWVSI

Q9IBI3 Hepatitis B virus genotype G (isolate IG29227/2000)
PreS1
(SEQ ID NO: 57)
MGLSWTVPLEWGKNLSASNPLGFLPDHQLDPAFRANTNNPDWDFNPKKDPWPEANKVGVGAYGPGFTP

PHGGLLGWSPQSQGTLTTLPADPPPASTNRQGRQPTPI

PreS2
(SEQ ID NO: 58)
SPPLRDSHPQAMQWNSTAFHQALQNPKVRGLYFPAGGSSSGIVNPVPTIASHISS

S-HBsAg
(SEQ ID NO: 59)
IFSRIGDPAPNMENITSGFLGPLLVLQAGFFLLTRILTIPQSLDSWWTSLNFLGGVPVCPGLNSQSPT

SNHSPISCPPTCPGYRWMCLRRFIIFLFILLLCLIFLLVLLDYQGMLPVCPLIPGSSTTSTGPCKTCT

TPAQGNSMYPSCCCTKPSDGNCTCIPIPSSWAFAKYLWEWASVRFSWLSLLVPFVQWFVGLSPTVWLS

AIWMMWYWGPNLYNILSPFIPLLPIFFCLWVYI

M-HBsAg
(SEQ ID NO: 60)
SPPLRDSHPQAMQWNSTAFHQALQNPKVRGLYFPAGGSSSGIVNPVPTIASHISSIFSRIGDPAPNME

NITSGFLGPLLVLQAGFFLLTRILTIPQSLDSWWTSLNFLGGVPVCPGLNSQSPTSNHSPISCPPTCP

GYRWMCLRRFIIFLFILLLCLIFLLVLLDYQGMLPVCPLIPGSSTTSTGPCKTCTTPAQGNSMYPSCC

CTKPSDGNCTCIPIPSSWAFAKYLWEWASVRFSWLSLLVPFVQWFVGLSPTVWLSAIWMMWYWGPNLY

NILSPFIPLLPIFFCLWVYI

L-HBsAg
(SEQ ID NO: 61)
MGLSWTVPLEWGKNLSASNPLGFLPDHQLDPAFRANTNNPDWDFNPKKDPWPEANKVGVGAYGPGFTP

PHGGLLGWSPQSQGTLTTLPADPPPASTNRQGRQPTPISPPLRDSHPQAMQWNSTAFHQALQNPKVR

GLYFPAGGSSSGIVNPVPTIASHISSIFSRIGDPAPNMENITSGFLGPLLVLQAGFFLLTRILTIPQS

```
LDSWWTSLNFLGGVPVCPGLNSQSPTSNHSPISCPPTCPGYRWMCLRRFIIFLFILLLCLIFLLVLLD

YQGMLPVCPLIPGSSTTSTGPCKTCTTPAQGNSMYPSCCCTKPSDGNCTCIPIPSSWAFAKYLWEWAS

VRFSWLSLLVPFVQWFVGLSPTVWLSAIWMMWYWGPNLYNILSPFIPLLPIFFCLWVYI

Q8JMY6 Hepatitis B virus genotype H (isolate United
States/LAS2523/2002)
PreS1
                                                        (SEQ ID NO: 62)
MGAPLSTARRGMGQNLSVPNPLGFFPDHQLDPLFRANSSSPDWFENTNKDNWPMANKVGVGGFGPGFT

PPHGGLLGWSPQAQGILTTSPPDPPPASTNRRSGRKPTPV

PreS2
                                                        (SEQ ID NO: 63)
SPPLRDTHPQAMQWNSTQFHQALLDPRVRGLYFPAGGSSSETQNPAPTIASLTSS

S-HBsAg
                                                        (SEQ ID NO: 64)
IFSKTGDPAMNMENITSGLLRPLLVLQAVCFLLTKILTIPQSLDSWWTSLNFLGVPPGCPGQNSQSPI

SNHLPTSCPPTCPGYRWMCLRRFIIFLFILLLCLIFLLVLLDYQGMLPVCPLLPGSTTTSTGPCKTCT

TLAQGTSMFPSCCCTKPSDGNCICIPIPSSWAFGKYLWEWASARFSWLSLLVQFVQWCVGLSPTVWLL

VIWMIWYWGPNLCSILSPFIPLLPIFCYLWASI

M-HBsAg
                                                        (SEQ ID NO: 65)
SPPLRDTHPQAMQWNSTQFHQALLDPRVRGLYFPAGGSSSETQNPAPTIASLTSSIFSKTGDPAMNME

NITSGLLRPLLVLQAVCFLLTKILTIPQSLDSWWTSLNFLGVPPGCPGQNSQSPISNHLPTSCPPTCP

GYRWMCLRRFIIFLFILLLCLIFLLVLLDYQGMLPVCPLLPGSTTTSTGPCKTCTTLAQGTSMFPSCC

CTKPSDGNCTCIPIPSSWAFGKYLWEWASARFSWLSLLVQFVQWCVGLSPTVWLLVIWMIWYWGPNLC

SILSPFIPLLPIECYLWASI

L-HBsAg
                                                        (SEQ ID NO: 66)
MGAPLSTARRGMGQNLSVPNPLGFFPDHQLDPLFRANSSSPDWDFNTNKDNWPMANKVGVGGFGPGFT

PPHGGLLGWSPQAQGILTTSPPDPPPASTNRRSGRKPTPVSPPLRDTHPQAMQWNSTQFHQALLDPRV

RGLYFPAGGSSSETQNPAPTIASLTSSIFSKTGDPAMNMENITSGLLRPLLVLQAVCFLLTKILTIPQ

SLDSWWTSLNFLGVPPGCPGQNSQSPISNHLPTSCPPTCPGYRWMCLRRFIIFLFILLLCLIFLLVLL

DYQGMLPVCPLLPGSTTTSTGPCKTCTTLAQGTSMFPSCCCTKPSDGNCTCIPIPSSWAFGKYLWEWA

SARFSWLSLLVQFVQWCVGLSPTVWLLVIWNIWYWGPNLCSILSPFIPLLPIFCYLWASI
```

In various further embodiments, the composition may comprise an HBVpreS1/S2Ag or S-HBsAg polypeptide at least 91%, 92%, 93%, 94%, 95%, 96%, 97%, 98%, 99%, or 100% identical over the length of the amino acid sequence of the sequences shown above. In various embodiments, additional HBVpreS1/S2Ag mutations may be included (alone or in combination). These mutations may include, but are not limited to, the preS1 S98T substitution (PLOS One 9: e110012, 2014), the preS1 F53L substitution (J Med Virol 85: 1698, 2013), or the preS1 A39R and preS1 S96A/T substitutions (Clin Microbial Infect 18: E412, 2012).

In all of these embodiments, the composition may further comprise an amino acid linker position between the CD180 binding ligand and the HBVpreS1/S2Ag or S-HBsAg. The linker may be of any suitable length and amino acid composition, depending on the intended use. In one embodiment, the linker is between about 2-40 amino acids in length. In other embodiments, the linker may be between 10-30 or 15-25 amino acids in length. In another embodiment, the linker may be a linker rich in glycine and serine residues. In one specific embodiment, the linker may comprise the amino acid sequence

```
                                                        (SEQ ID NO: 69)
             GGGGSGGGGSGGGGSGGGGS.
```

In various further embodiments, the composition may comprise or consist of a polypeptide at least 90% identical over its length to the following amino acid sequence of G28-8LH-scAb-PreS1-S2-His protein_(expressed)

```
                                                        (SEQ ID NO: 67)
   (METPAQLLFL LLLWLPDTTG) DIQMTQSPAS LSASVGETVT

ITCRASEKIY SYLAWYQQKQ

61 GKSPQLLVYN AKTLAEGVPS RFSVSGSGTQ FSLRINSLQP

EDFGTYYCQH HFGSPRTFGG
```

-continued

```
121 GTKLEIKDLG GGGGSGGGGSG GGGSGGGGST GEVQLQQSGP

ELVKPGASMK ISCKASGYSF

181 TGYTMNWVKQ SHGKTLEWIG LINPYNGVTS YNQKFKDKAT

LTVDKSSSTA YMELLSLTSE

241 DSAIYYCARD YNYDYFDYWG QGTTLTVSSD LEPKSSDKTH

TCPPCPAPEL LGGSSVFLFP

301 PKPKDTLMIS RTPEVTCVVV DVSHEDPEVK FNWYVDGVEV

HNAKTKPREE QYNSTYRVVS

361 VLTVLHQDWL NGKEYKCSVS NKALPASIEK TISKAKGQPR

EPQVYTLPPS REEMTKNQVS

421 LTCLVKGFYP SDIAVEWESN GQPENNYKTT PPVLDSDGSF

ELYSKLTVDK SRWQOGNVES

481 CSVMHEALHN HYTQKSLSLS PGKGGGGSGG GGSGGGGSGG

GGSMGGWSSK PRQGMGTNLS

541 VPNPLGFFPD HQLDPAFGAN SNNPDWDFNP NKDHWPEANQ

VGAGAFGPGF TPPHGGLLGW

601 SPQAQGILTT LPAAPPPAST NRQSGRQPTP ISPPLRDSHP

QAMQWNSTTF HQALLDPRVR

661 GLYFPAGGSS SGTVYPVPTT ASPISSIFSR TGDPAPN(HHH

HHH)
Amino acids 1-20: Leader (optional)
Amino acids 21-129: G28-8VL (Bold)
Amino acids 130-149: Gly-Ser Linker
Amino acids 150-269: G28-BVH (Bold and underlined)
Amino acids 270-503: Hing-CH2-CH3
Amino acids 504-533: Gly-Ser Linker
Amino acids 534-697: preS1/preS2
Amino acids 698-703: 6xHis
Residues in parentheses are optional
```

The compositions of any embodiment or combination of embodiments of the disclosure may be provided as a stand-alone composition, or may be provided as part of a molecular scaffold. In various embodiments, the composition may be attached to molecular scaffold. Any suitable scaffold can be used, including but not limited to a VNAR single domain antibody (shark variable new antigen receptor), a lamprey variable lymphocyte receptor, a Im 7(colicin immunity 7 protein), an anticalin (lipocalin transport proteins), an FN3 (fibronectin 3) monobody, a DARPin (designed ankyrin repeat proteins), an affibody (Z domain of protein A), a single domain antibody, e.g, isolated from camelids or antibody libraries, and aptamer, etc., with CD180-binding polypeptide loops.

In another embodiment, the composition of any embodiment or combination of embodiments of the disclosure further comprises an adjuvant. While adjuvant is not required to induce rapid activation of HBVpreS1/S2Ag or S-HBsAg, addition of adjuvant to the compositions can result in additional enhancement of the immune response when the compositions are used in the methods of the disclosure. Any suitable adjuvant can be used, including but not limited to inorganic compounds (aluminum hydroxide, aluminum phosphate, calcium phosphate hydroxide, beryllium, etc.), mineral oil, detergents, cytokines, toll-like receptor agonists, Freund's complete adjuvant, Freund's incomplete adjuvant, squalene, etc. In a preferred embodiment, the adjuvant comprises or consists of a toll-like receptor 4 (TLR4) agonist, a toll-like receptor 7 (TLR7) agonist, a toll-like receptor 8 (TLR8) agonist, a toll-like receptor 9 (TLR9) agonist, alum-containing adjuvant, monophosphoryl lipid A, oil-in-water emulsion, and α-tocopherol, squalene and polysorbate 80 in an oil-in-water emulsion. The adjuvant may be present in the composition as an unlinked component or a linked component, depending on the adjuvant used.

In another embodiment, the compositions of the disclosure can be modified to extend half-life, such as by attaching at least one molecule to the composition for extending serum half-life, including but not limited to a polyethlyene glycol (PEG) group, serum albumin, a serum albumin binding domain, transferrin, transferrin receptor or the transferrin-binding portion thereof, or combinations thereof. As used herein, the word "attached" refers to a covalently or non-covalently conjugated substance. The conjugation may be by genetic engineering or by chemical means.

The compositions of the present disclosure may be stored in any suitable buffer.

In a second aspect, the present disclosure provides isolated nucleic acids encoding the composition of any embodiment of the first aspect of the disclosure. The isolated nucleic acid sequence may comprise RNA or DNA. Such isolated nucleic acid sequences may comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals. In one non-limiting embodiment, the isolated nucleic acids encode a polypeptide of the disclosure noted herein. In other embodiments, the isolated nucleic acids comprise or consist of the nucleotide sequence shown below.

```
G28-8LH-scAb-PreS1-S2-His 2142 bp
                                        (SEQ. ID NO: 68)
  1  GCGAAGCTTT GAGCCACCAT GGAAACCCCA GCGCAGCTTC
     TCTTCCTCCT GCTACTCTGG
 61  CTCCCAGATA CCACCGGTGA CATCCAGATG ACTCAGTCTC
     CAGCCTCCCT ATCTGCATCT
121  GTGGGAGAAA CTGTCACCAT CACATGTCGA GCAAGTGAGA
     AGATTTACAG TTATTTAGCA
181  TGGTATCAGC AGAAACAGGG AAAATCTCCT CAGCTCCTGG
     TCTATAACGC AAAAACCTTA
241  GCAGKAGGTG TGCCATCAAG GTTCAGTGTC AGTGGATCAG
     GCACACAGTT TTCTCTGAGG
301  ATCAACAGCC TGCAGCCTGA AGATTTTGGG ACTTATTACT
     GTCAACATCA TTTTGGTTCT
361  CCTCGGACGT TCGGTGGAGG CACCAAACTG GAAATCAAAG
     ATCTCGGAGG AGGTGGCTCA
421  GGTGGTGGAG GATCTGGAGG AGGTGGGAGT GGTGGAGGTG
     GTTCTACCGG TGAGGTCCAG
```

-continued

```
 481 CTGCAACAGT CTGGACCTGA ACTGGTGAAG CCTGGAGCTT
     CAATGAAGAT ATCCTGCAAG
 541 GCTTCTGGTT ACTCATTCAC TGGCTACACC ATGAACTGGG
     TGAAGCAGAG CCATGGAAAG
 601 ACCCTTGAAT GGATTGGACT TATTAATCCT ACAATGGTG
     TTACTAGCTA CAACCAGAAG
 661 TTCAAGGACA AGGCCACATT AACTGTAGAC AAGTCATCCA
     GCACAGCCTA CATGGAACTC
 721 CTCAGTCTGA CATCTGAGGA CTCTGCAATC TATTACTGTG
     CAAGAGACTA TAATTACGAC
 781 TACTTTGACT ACTGGGGCCA AGGCACCACT CTCACAGTCT
     CCTCAGATCT CGAGCCCAAA
 641 TCTTCTGACA AAACTCACAC ATGTCCACCG TGTCCAGCAC
     CTGAACTCCT GGGTGGATCG
 901 TCAGTCTTCC TCTTCCCCCC AAAACCCAAG GACACTCTCA
     TGATCTCCCG GACCCCTGAG
 961 GTCACGTGCG TGGTGGTGGA CGTGAGCCAC GAAGACCCCG
     AGGTCAAGTT CAACTGGTAC
1021 GTGGACGGCG TGGAGGTGCA TAATGCCAAG ACAAAGCCAC
     GGGAGGAGCA GTACAACAGC
1081 ACGTACCGTG TGGTCAGCGT CCTCACCGTC TTGCACCAGG
     ACTGGCTGAA CGGCAAGGAG
1141 TACAAGTGCT CGGTCTCCAA CAAAGCCCTC CCAGCCTCCA
     TCGAGAAAAC AATCTCCAAA
1201 GCCAAAGGGC AGCCCCGAGA ACCACAGGTG TACACCCTGC
     CCCCATCCCG GGAGGAGATG
1261 ACCAAGAACC AGGTCAGCCT GACCTGCCTG GTCAAAGGCT
     TCTATCCCAG CGACATCGCC
1321 GTGGAGTGGG AGAGCAATGG GCAGCCGGAG AACAACTACA
     AGACCACGCC TCCCGTGCTG
1381 GACTCCGACG GCTCCTTCTT CCTCTACAGC AAGCTCACCG
     TGGACAAGAG CAGGTGGCAG
1441 CAGGGGAACG TCTTCTCATG CTCCGTGATG CATGAGGCTC
     TGCACAACCA CTACACGCAG
1501 AAGAGCCTCT CTCTGTCTCC GGGTAAAGGA GGAGGTGGCT
     CAGGTGGTGG AGGATCTGGA
1561 GGAGGTGGGA CTGGTGGAGG TGGTTCTATG CGAGGTTGGT
     CTTCCAAACC TCGACAAGGC
1621 ATGGGACGA ATCTTTCTGT TCCCAATCCT CTGGGATTCT
     TTCCCGATCA CCAGTTGGAC
1681 CCTGCGTTCG GAGCCAACTC AAACAATCCA GATTGGGACT
     TCAACCCCAA CAAGGATCAC
1741 TGGCCAGAGG CAAATCASGT AGGAGCGGGA GCATTTGGTC
     CAGGGTTCAC CCCACCACAC
1801 GGAGGCCTTT TGGGGTGGAG CCCTCAGGCT CAGGGCATAT
     TGACAACACT GCCAGCAGCA
1861 CCTCCTCCTG CCTCCACCAA TCGGCAGTCA CGAAGACAGC
     CTACTCCCAT CTCTCCACCT
1921 CTAAGAGACA GTCATCCTCA GGCCATGCAG TGGAACTCCA
     CAACATTCCA CCAAGCTCTG
1981 CTAGATCCCA GAGTGAGGGG CCTATATTTT CCTGCTGGTG
     GCTCCAGTTC CGGAACAGTA
2041 AACCCTGTTC CGACTACTGC CTCACCCATA TCGTCAATCT
     TCTCGAGGAC TGGGGACCCT
2101 GCACCGAACC ACCACCATCA TCATCATTGA TAAGGATCCG
     CG
```

5' end HindIII and 3' end BamHI sites for directional cloning into appropriate expression vector Kozak consensus, GCCACC, right before 5' ATG start codon One 5' in frame stop codon after 5' end HindIII site Two in frame stop codons before 3' end BamHI site In a third aspect, the present disclosure provides nucleic acid vectors comprising the isolated nucleic acid of the second aspect of the disclosure. "Recombinant expression vector" includes vectors that operatively link a nucleic acid coding region or gene to any promoter capable of effecting expression of the gene product. The promoter sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The expression vector must be replicable in the host organisms either as an episome or by integration into host chromosomal DNA. In a preferred embodiment, the expression vector comprises a plasmid. However, the disclosure is intended to include other expression vectors that serve equivalent functions, such as viral vectors.

The nucleic acids and vectors of the disclosure can be used not only for production of large quantities of the compositions of the disclosure, but also for use as a nucleic acid (such as a DNA) vaccine administered by gene gun or other methods.

In a fourth aspect, the present disclosure provides recombinant host cells comprising the nucleic acid vector of the third aspect of the disclosure. The host cells can be either prokaryotic or eukaryotic. The cells can be transiently or stably transfected. Such transfection of expression vectors into prokaryotic and eukaryotic cells (including but not limited to Chinese hamster ovary (CHO) cells) can be accomplished via any suitable means, including but not limited to bacterial transformations, calcium phosphate co-precipitation, electroporation, or liposome mediated-, DEAE dextran mediated-, polycationic mediated-, or viral mediated transfection.

The recombinant host cells can be used, for example in methods for producing antibody (when the binding protein is an antibody), comprising:

(a) culturing the recombinant host cell of the disclosure under conditions suitable for expression of the nucleic-acid encoded antibody composition; and (b) isolating the antibody composition from the cultured cells.

Suitable conditions for expression of the nucleic-acid encoded antibody composition can be determined by those of skill in the art based on the teachings herein and the specific host cells and vectors used.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operable linkage of different sequences is achieved. Thus an isolated nucleic acid, in a linear form, or an expression vector formed in vitro by ligating DNA molecules that are not normally joined, are both considered recombinant for the purposes disclosed herein. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes disclosed herein.

In a fifth aspect, the present disclosure provides pharmaceutical compositions, comprising:

(a) the composition, isolated nucleic acid, or recombinant expression vector of any embodiment or combination of embodiments disclosed herein; and (b) a pharmaceutically acceptable carrier.

In this embodiment, the compositions of the disclosure are present in a pharmaceutical formulation. In this embodiment, the compositions are combined with a pharmaceutically acceptable carrier. Suitable acids which are capable of forming such salts include inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid and the like. Suitable bases capable of forming such salts include inorganic bases such as sodium hydroxide, ammonium hydroxide, potassium hydroxide and the like; and organic bases such as mono-, di- and tri-alkyl and aryl amines (e.g., triethylamine, diisopropyl amine, methyl amine, dimethyl amine and the like) and optionally substituted ethanol-amines (e.g., ethanolamine, diethanolamine and the like).

The pharmaceutical composition may comprise in addition to the composition of the disclosure (a) a lyoprotectant; (b) a surfactant; (c) a bulking agent; (d) a tonicity adjusting agent; (e) a stabilizer; (f) a preservative and/or (g) a buffer. In some embodiments, the buffer in the pharmaceutical composition is a Tris buffer, a histidine buffer, a phosphate buffer, a citrate buffer or an acetate buffer. The pharmaceutical composition may also include a lyoprotectant, e.g. sucrose, sorbitol or trehalose. In certain embodiments, the pharmaceutical composition includes a preservative e.g. benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. In other embodiments, the pharmaceutical composition includes a bulking agent, like glycine. In yet other embodiments, the pharmaceutical composition includes a surfactant e.g., polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or a combination thereof. The pharmaceutical composition may also include a tonicity adjusting agent, e.g., a compound that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the pharmaceutical composition additionally includes a stabilizer, e.g., a molecule which, when combined with a protein of interest substantially prevents or reduces chemical and/or physical instability of the protein of interest in lyophilized or liquid form. Exemplary stabilizers include sucrose, sorbitol, glycine, inositol, sodium chloride, methionine, arginine, and arginine hydrochloride.

The pharmaceutical compositions of the disclosure may be made up in any suitable formulation, preferably in formulations suitable for administration by injection. Such pharmaceutical compositions can be used, for example, in methods of use as vaccines, prophylactics, or therapeutics.

The pharmaceutical compositions may contain any other components as deemed appropriate for a given use, such as additional therapeutics or vaccine components. In one embodiment, the pharmaceutical compositions further comprise toll-like receptor 4 (TLR4) agonist, a toll-like receptor 7 (TLR7) agonist, a toll-like receptor 8 (TLR8) agonist, a toll-like receptor 9 (TLR9) agonist, alum-containing adjuvant, monophosphoryl lipid A, oil-in-water emulsion, and α-tocopherol, squalene and polysorbate 80 in an oil-in-water emulsion.

In a sixth aspect, the present disclosure provides methods for treating or limiting development of an HBV infection or a hepatitis-B virus (HBV)-related disorder, comprising administering to an individual in need thereof an amount effective to treat or limit development of the disorder of the composition, isolated nucleic acid, recombinant expression vector, or pharmaceutical composition, or a pharmaceutical salt thereof, of any embodiment or combination of embodiments of the present disclosure. In one embodiment, the compositions are used prophylactically as vaccines to limit development of HBV infection disease/severity of infectious disease, such as in individuals that have not been exposed to an infectious agent but are at risk of such exposure. In other embodiments, the methods can be used therapeutically to treat people exposed to or chronically infected with HBV.

The methods of the disclosure target antigen to CD180, a surface protein expressed on B cells, macrophages, and dendritic cells, that to produce antigen-specific IgG in the absence of T cell costimulation (such as CD40 deficiency) or the complete absence of T cells (such as TCR β/δ deficiency). Thus, the methods can be used in any therapeutic or prophylactic treatment for HBV infection or vaccination. This approach also finds use, for example, for neonates, the elderly, the immunocompromised, and the immunodeficient, both in specifically targeting cellular populations enriched in underdeveloped or otherwise deficient immune systems and by improving responses to antigens that require linked recognition (carbohydrate epitopes, etc.).

As used herein, "treat" or "treating" means accomplishing one or more of the following in an individual that already has a disorder or has already been exposed to a disorder-causing substance/pathogen: (a) reducing the severity of the disorder; (b) limiting or preventing development of symptoms characteristic of the disorder(s) being treated (ex: immune deficiencies in cancer patients or other patients) undergoing chemotherapy and/or radiation therapy); (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

As used herein, "limiting" or "limiting development of" means accomplishing one or more of the following in an individual that does not have the disorder to be limited: (a) preventing the disorder; (b) reducing the severity of the disorder; and (c) limiting or preventing development of symptoms characteristic of the disorder.

As used herein, an "amount effective" refers to an amount of the composition that is effective for treating and/or limiting the relevant disorder.

While the methods of the disclosure do not require use of an adjuvant, the methods may further comprise administering an adjuvant for possible additional enhancement of the immune response Any suitable adjuvant can be used, including but not limited to toll-like receptor 4 (TLR4) agonist, a toll-like receptor 7 (TLR7) agonist, a toll-like receptor 8 (TLR8) agonist, a toll-like receptor 9 (TLR9) agonist, alum-containing adjuvant, monophosphoryl lipid A, oil-in-water emulsion, and α-tocopherol, squalene and polysorbate 80 in an oil-in-water emulsion.

The individual may be any suitable individual, including but not limited to mammals. Preferably the individual is a human. In one embodiment, the individual has a T-cell deficiency and/or a defect in co-stimulation between B cells and T cells, or is immuno-compromised by chronic infections or from acute or chronic taking of immunosuppressive drugs for treatment of autoimmune diseases, or other inflammatory disease . In another embodiment, the individual is less than one month old or is elderly (i.e.: at least 65 years old).

In various other embodiments, the individual has a hepatitis B-related disease, such as hepatitis, hepatitis-related disease, fulminant hepatitis, cirrhosis, and/or hepatocellular carcinoma, and the methods are used to treat the a hepatitis B-related disease, such as hepatitis, hepatitis-related disease, fulminant hepatitis, cirrhosis, and/or hepatocellular carcinoma.

EXAMPLE 1

Generation and Characterization of G28-8LH-scAb-PreS1-S2-His Recombinant Protein Molecules.

```
G28-8LH-scAb-PreS1-S2-His_protein_(expressed)
                                        (SEQ ID NO: 67)
  1 (METPAQLLFL ILLWLPDTTG) DIQMTQSPAS LSASVGETVT

ITCRASEKIY SYLAWYQQKQ

61 GKSPQLLVYN AKTLAEGVPS RFSVSGSGTQ FSLRINSLQP

EDFGTYYCQH HFGSPRTFGG

121 GTKLEIKDLG GGGSGGGGSG GGGSGGGGST GEVQLQQSGP

ELVKPGASMK ISCKASGYSF

181 TGYTMNWVKQ SHGKTLEWIG LINPYNGVTS YNQKFKDKAT

LTVDKSSSTA YMELLSLTSE

241 DSAIYYCARD YNYDYFDYWG QGTTLTVSSD LEPKSSDKTH

TCPPCPAPEL LGGSSVFLFP

301 PKPKDTLMIS RTPEVTCVVV DVSHEDPEVK FNWYVDGVEV

HNAKTKPREE QYNSTYRVVS

361 VLTVLHQDWL NGKEYKCSVS NKALPASIEK TISKAKGQPR

EPQVYTLPPS REEMTKNQVS

421 LTCLVKGFYP SDIAVEWESN GQPENNYKTT PPVLDSDGSF

FLYSKLTVDK SRWQQGNVES

481 CSVMHEALHN HYTQKSLSLS PGKGGGGSGG GGSGGGGSGG

GGSMGGWSSK PRQGMGTNLS

541 VPNPLGFFPD HQLDPAFGAN SNNPDWDFNP NKDHWPEANQ

VGAGAFGPGF TPPHGGLLGW

601 SPQAQGILTT LPAAPPPAST NRQSGRQPTP ISPPLRDSHP

QAMQWNSTTF HQALLDPRVR

661 GLYFPAGGSS SGTVNPVPTT ASPISSIFSR TGDPAPN(HHH

HHH)
Amino acids 1-20: Leader (optional)
Amino acids 21-129: G28-8VL (Bold)
Amino acids 130-149: Gly-Ser Linker
Amino acids 150-269: G28-BVH (Bold and underlined)
Amino acids 270-503: Hing-CH2-CH3
Amino acids 504-533: Gly-Ser Linker
Amino acids 534-697: preS1/preS2
Amino acids 698-703: 6xHis
Residues in parentheses are optional
```

G28-8 (anti-human CD180)-scAb-PreS1/S2 recombinant protein molecules. The inventors have demonstrated that for the specific anti-CD180 antibody, G28-8, a single chain antibody (scAb) in the form of VLVH-human IgG1 Fc retains both the efficient binding as well as the biological properties of its parent G28-8 IgG. The G28-8LH scAb is used to create G28-8LH-scAb-PreS1-S2-His recombinant protein constructs. It is anticipated that scFv generated from other anti-CD180 antibodies may retain the antibody characteristics in either the VLVH, VHVL, or only the VHVL configuration.

Production of recombinant the G28-8LH-scAb-PreS1-S2-His protein. Complementary DNAs (cDNAs) encoding the G28-8LH-scAb-PreS1-S2-His recombinant proteins (FIG. 1, G28-8LH-scAb-PreS1-S2-His protein) were cloned into the mammalian expression vector pTT5 that harbors a CMV promoter to drive protein expression. Transient transfection of these plasmids into Chinese hamster ovary (CHO) cells was done using Lipofectamine™ reagents (Invitrogen Carlsbad, Calif.) or polyethyleninmine (PEI). Small-scale transfection optimization using 5%, 20% and 80% ratios of expression plasmid in the lipofection reagent was conducted to identify to optimal plasmid to lipofection reagent ratios for larger scale expression. Once optimized transfection conditions are established, a large-scale transfection will be conducted for each of the plasmids for recombinant protein production. Nickel affinity chromatography, e.g., using the HisPurNi-NTA™ resin (Thermo Fisher Scientific Inc., Rockford IL), was used to purify the recombinant proteins. The cDNA sequences for the G28-8LH-scAb-HBV-PreS1/S2 protein predicts a polypeptide size of ~75 kDa. The expressed dimeric form of the recombinant protein is predicted to have a molecular weight of 150 kDa.

Figure 2:
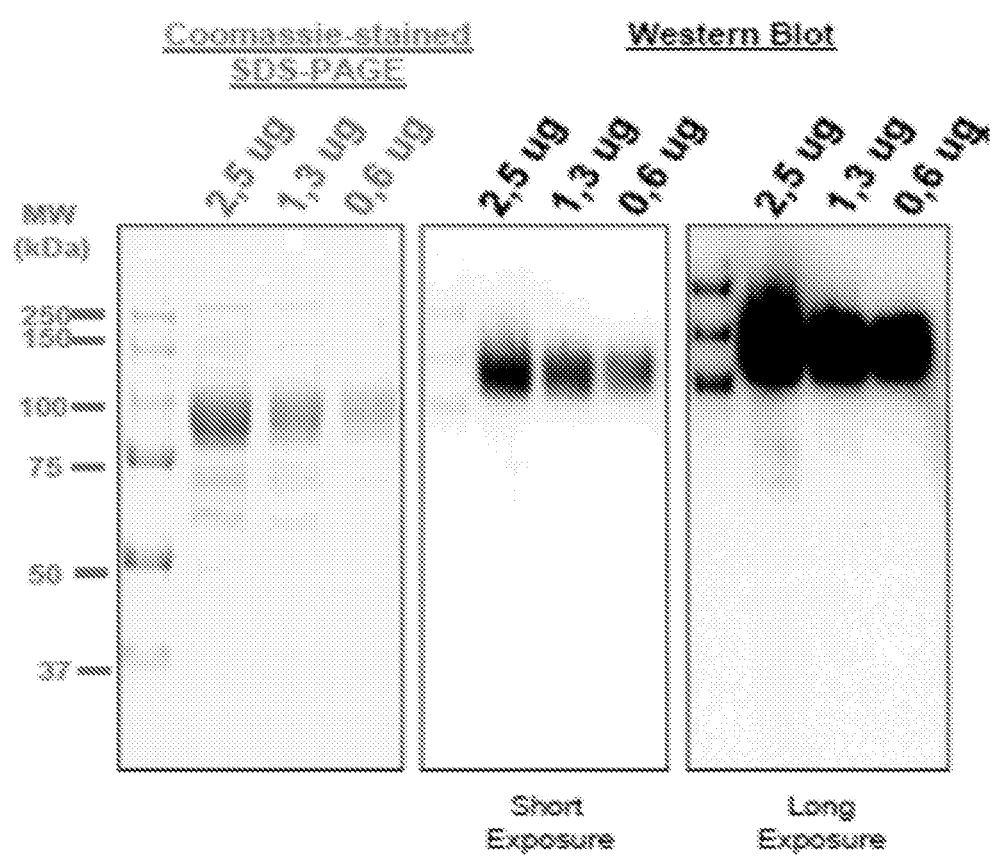
FIG. 2. Characterization of recombinant G28-8LH-scAb-PreS1-S2-His. G28-8LH-scAb-PreS1-S2-His was transiently expressed in CHO cells. Culture supernatant was passed over a Ni2+ affinity chromatography column. Bound G28-8LH-scAb-PreS1-S2-His was eluted with imidazole. Eluted protein (E) was characterized by reducing SDS-PAGE and western blotting using an anti-6x-His antibody.

FIG. 2 shows the results from a 2-liter expression run. The plasmid encoding the G28-8LH-scAb-PreS1-S2-His protein was transiently expressed in CHO cells for 8 days. Culture supernatants (~2 liters) were collected and cellular debris was removed by centrifugation. Clarified culture supernatants were then loaded on to a column containing HisPurNi-NTA™ resin. After washing the column with the wash buffer (50 mM phosphate buffer, pH 7.0, 300 mM NaCl, 1 mM imidazole), bound recombinant protein was eluted with the elution buffer (50 mM phosphate buffer, pH 7.0, 300 mM NaCl, 150 mM imidazole). Protein containing fractions as monitored by absorbance at 280 nM were collected, pooled, and dialyzed against phosphate-buffer saline at pH 7.0. Purified G28-8LH-scAb-PreS1-S2-His and unbound flow through materials from HisPurNi-NTA™ chromatography was analyzed on SDS-PAGE (4-15% gradient under reducing conditions) stained with Coomassie blue. FIG. 2, left panel shows a major protein band migrating at the MW of ~85 kDa, suggesting that G28-8LH-scAb-PreS1-S2-His protein was in fact expressed by CHO cells as an intact protein and secreted into the culture supernatants. A duplicate gel was then transferred onto a nylon membrane and immuno-blotted with an anti-6x-His antibody. Intense anti-6xHis signals were only observed at ~85 kDa (FIG. 2, right panel), at the identical MW G28-8LH-scAb-PreS1-S2-His migrated to on the Coomassie blue stained gel (FIG. 2, left panel).

EXAMPLE 2

Characterization of G28-8LH-scAb-PreS1-S2-His

Figure 3:
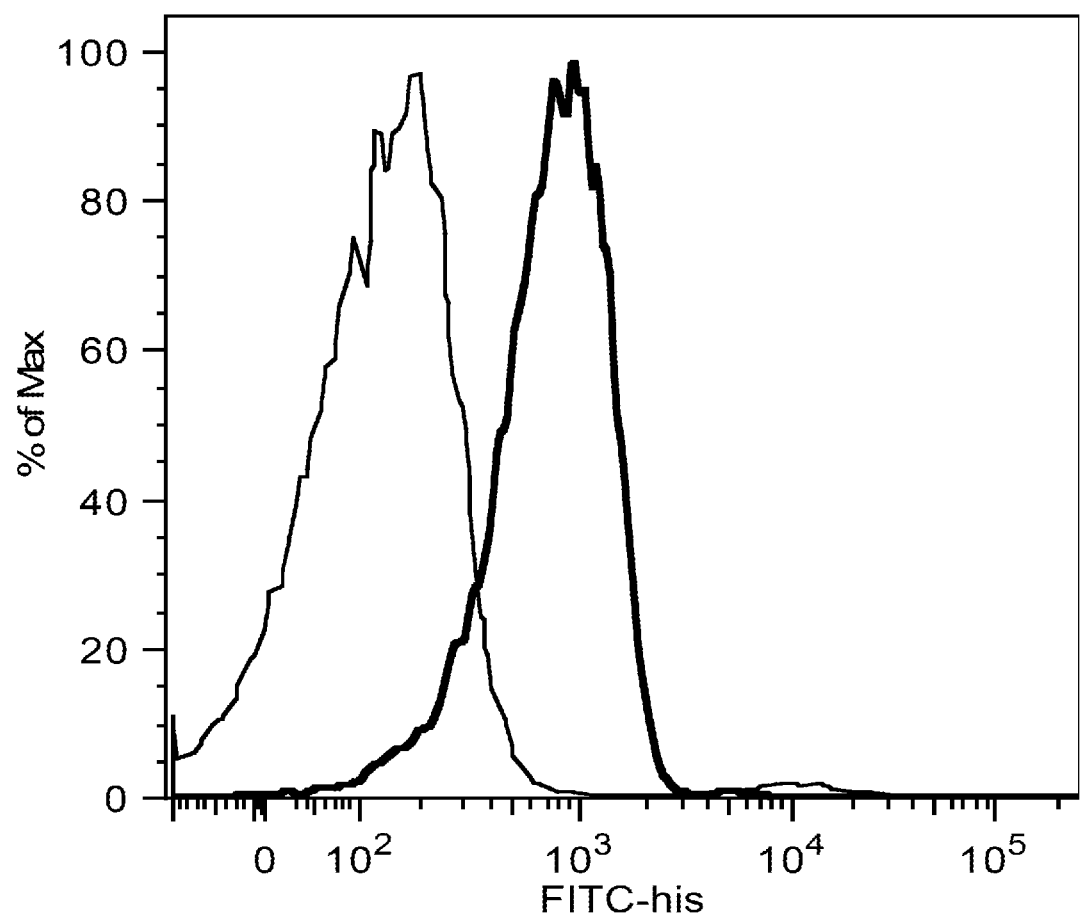
FIG. 3. Binding of recombinant G28-8LH-scAb-PreS1-S2-His to human B cells. Direct binding to human gated CD20+ tonsillar B cells using a FITC-anti-His monoclonal antibody (bold black line). Second step only (light black line).

FIG. 3 shows that human CD20+ tonsillar B cells ($10^6$) were incubated in 96 well round bottom plates with PBSA (PBS w/0.2% BSA+0.2% NaN3) media only (gray) or with the His tagged recombinant protein containing the light and heavy chains of G28-8 anti-human CD180 (LH) G28-8LH-scAb-PreS1-S2-His (black), at 10 µg/ml. After a 40 min incubation on ice, the cells were washed twice (centrifuged at 1200 rpm, 4 min). Then 100 µl of PBSA+5 µl a fluorescein (FITC)-conjugated anti 6xHis (FITC-6x-His epitope tag ThermoScientific MA1-81891) were added to the wells, and after a 40 min incubation on ice, cells were washed twice and the level of fluorescence measured by flow cytometry shown on abscissa (log scale). Unstained cells are shown in black. The recombinant protein bound to B cells as shown by binding being above the FITC control, demonstrating binding to CD180 expressed on B cells.

Figure 4:
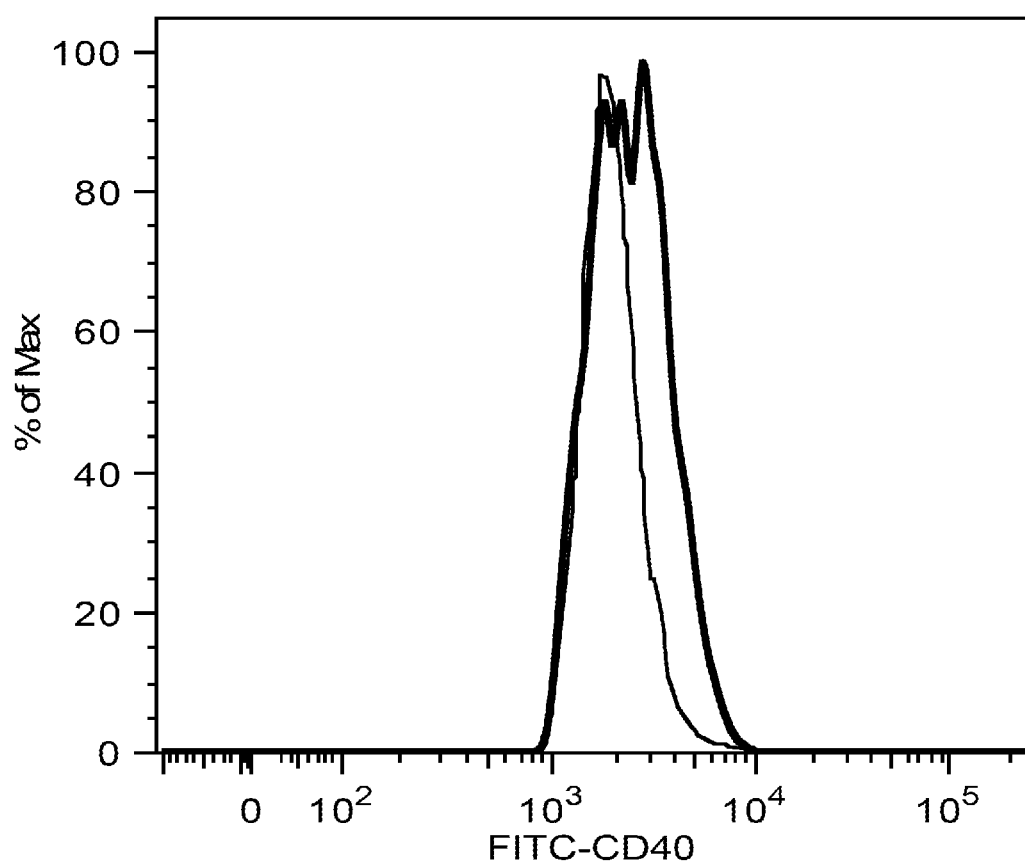
FIG. 4. Recombinant G28-8LH-scAb-PreS1-S2-His activates human B cells. Sheep erythrocyte-binding negative blood mononuclear cells enriched for B cells were incubated at 37 C for 24 hours either with media only (light black line), or with G28-8LH-scAb-PreS1-S2-His (bold black line). Samples were gated for CD20+ cells (Pacific blue-anti-CD20) and levels of CD40 expression measured as an indication of activation using flow cytometry. Graph shows CD40 expression of gated CD20+ B cells.

Ligation of CD180 on B cells has been shown to upregulate CD40 expression[51]. The ability of G28-8LH-scAb-PreS1-S2-His to upregulate CD40 expression was then tested to evaluate its functional activity (FIG. 4). Er– blood mononuclear cells enriched for B cells were incubated for 24 hrs at 37 C with either media (gray line) or 10 µg/ml of G28-8LH-scAb-HBV-PreS1/S2-His (black line). Samples were washed twice with PBSA, stained with mAb specific for CD20 (Pacific Blue Biolegend™) and CD40 (FITC BD BioSciences) and evaluated for CD40 and CD20 expression using flow cytometry. Graph shows CD40 expression of gated CD20+ B cells. G28-8LH-scAb-PreS1-S2-His upregulated CD40 expression, confirming that G28-8LH-scAb-PreS1-S2-His was functionally active (FIG. 4).

EXAMPLE 3

Figure 5:
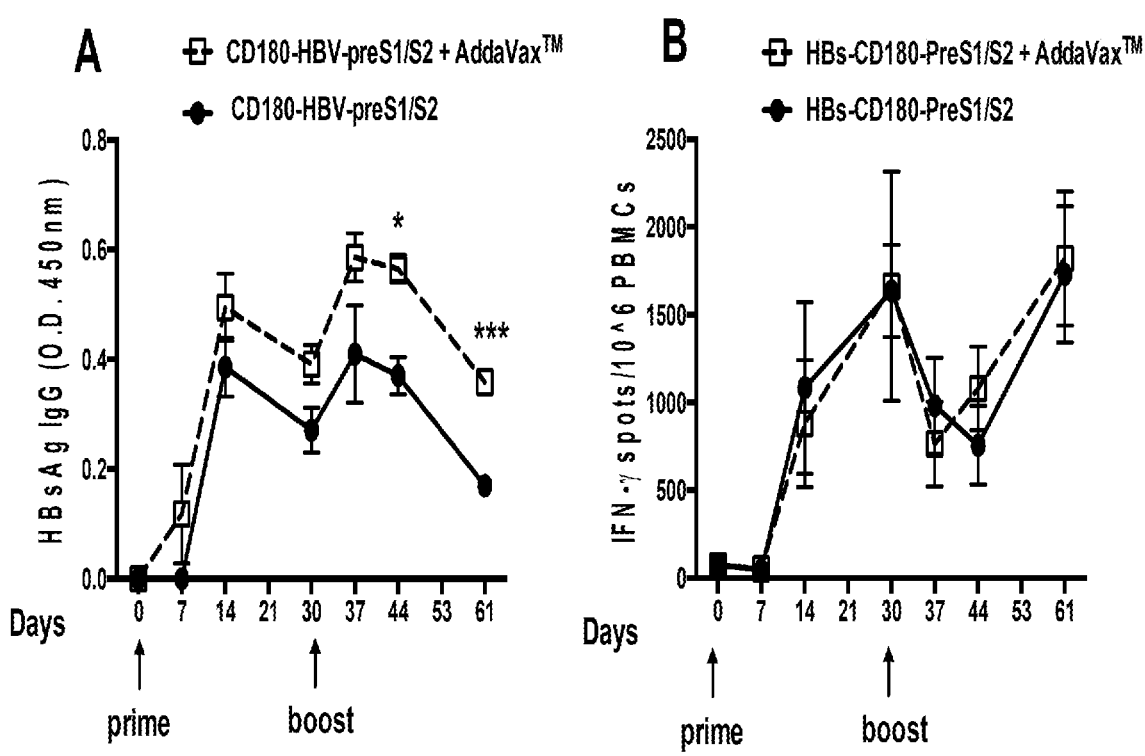
FIG. 5. Immune responses in macaques immunized and boosted with recombinant G28-8LH-scAb-PreS1-S2-His recombinant protein (CD180-HBV-preS1/S2). Groups of cynomolgus macaques (*Macaca fascicularis*) (N=3) were vaccinated subcutaneously with either: 1) 300 µg of G28-8LH-scAb-PreS1-S2-His (CD180-HBV-PreS1/S2, black circles); or 2) 300 µg of G28-8LH-scAb-PreS1-S2-His (αCD180-HBV-preS1/S2) plus 0.5 ml Addavax™ (open squares). Animals were vaccinated on days 0 and 30, and serum and heparinized blood samples were obtained on days 0, 7, 14, 30 after primary immunization and days 7, 14, and 30 after secondary immunization. (A) HBV-PreS1-specific IgG antibody levels detected using ELISA. Mean optical densities (O.D.) at each time point±SEM are indicated. (B) HBsAg-specific IFN-γ-producing T cells detected by EL1-spot assays. Statistical comparisons between the two groups for each assay were assessed at each timepoint using unpaired t test on samples with equal standard deviation. Significant differences are indicated: *P=0.01, ***P=0.006. For all other timepoints, there was no significant difference in mean responses between the groups.

Induction in Macaques of preS1-S2-Specific IgG Antibody Responses by G28-8LH-scAb-PreS1-S2-His Recombinant Protein The ability of G28-8LH-scAb-PreS1-S2-His to induce humoral and cellular immune responses was examined in a vaccination experiment in cynomolgus macaques (*Macaca fascicularis*). Groups of macaques (N=3) were vaccinated subcutaneously with either: 1) 300 µg of G28-8LH-scAb-PreS1-S2-His (αCD180-HBV-PreS1/S2) in 1 ml; or 2) 300 µg of G28-8LH-scAb-PreS1-S2-His co-formulated with 100 µg of the commercial adjuvant AddaVax™ (InVivoGen, San Diego, Calif.) in a total of 1 ml. Animals were vaccinated on days 0 and 30 and serum and heparinized blood samples were obtained on days 0, 7, 14, 30 (time-points after first dose), 37, 44 and 60 (time-points after second dose). Serum samples were assessed for IgG antibody responses to HBV preS1 by ELISA as follows: a) coating 96 well plates with 200 ng/well purified recombinant preS1 peptide (115 amino acids, Cosmo Bio. Japan cat# BCL-AGS1-01); b) adding serial dilutions of serum samples (100 µl diluted in TBS+ 0.05% tween-20) starting with a 1:1000 dilution, followed by washing and adding HRP-anti-macaque IgG second step (Rockland, 1:5000 dilution). Both groups produced IgG after immunizations (FIG. 5A). The antibody titers increased after each boost. The group receiving recombinant protein with AddaVax™ adjuvant had higher IgG antibody responses compared to group not given AddaVax™ at two time points after the second immunization.

EXAMPLE 4

Induction in Macaques of HBV-Specific T Cell Responses by G28-8LH-scAb-PreS1-S2-His To determine the frequency of HBV-PreS1/S2-specific, intracellular cytokine-producing T cells after vaccination of the macaques, peripheral blood mononuclear cells (PBMCs) were isolated from heparinized blood samples obtained from immunized macaques at the times before and after immunization as noted in Example 3. PBMCs were separated using gradient centrifugation and stimulated in vitro for 18 hours with HBsAg peptide pools (15mers overlapping by 11 amino acids). HBs-specific T cells secreting IFN-γ were detected using paired anti-macaque IFN-γ monoclonal antibodies (U-cytech-BV). Spot forming cells (SFC) were enumerated using an Immunospot™ Analyzer with CTL Immunospot™ Profession Software (Cellular Technology Ltd.). Results shown in FIG. 5B are mean SFC per 1 million PBMC time point±SEM. Tests were run in replicate wells. Net responses shown were determined by subtracting the number of spots from DMSO stimulated control wells from the same animal. Statistical comparisons between the two groups for each assay were assessed at each time point using unpaired t test on samples with equal standard deviation and resuspended in growth media at defined concentrations (~1.2 million cells/condition). The number of HBsAg-specific IFN-γ-producing T cells increased within 14 days after primary immunization with G28-8LH-scAb-PreS1-S2-His only and the addition of the AddaVax™ adjuvant did not increase HBsAg-specific T cell levels.

EXAMPLE 5

Figure 6:
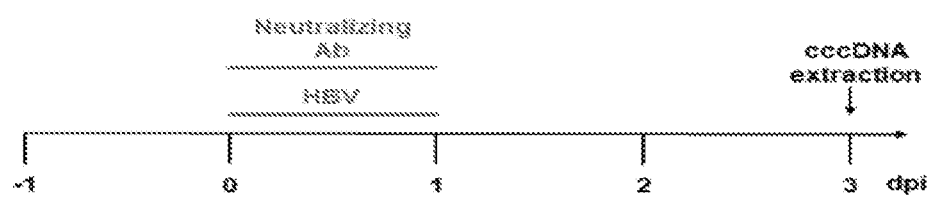
FIG. 6. G28-8LH-scAb-PreS1-S2-His recombinant protein vaccine induced neutralizing antibodies (Abs) that block the production of HBV cccDNA in HBV infected liver cells. Cynomolgus macaques (*Macaca fascicularis*, N=3/group) received a priming and booster as described in FIG. 11 with either 300 ug G28-8LH-scAb-PreS1-S2-His (A57, A59 and A60) or 300 µg G28-8LH-scAb-PreS1-S2-His co-formulated with 100 µg of the commercial adjuvant, AddaVax™ (A55, A58 and A68, indicated by * in figure). Sera obtained 2 weeks after the second immunization were evaluated for neutralizing antibody activity. (A) The scheme illustrates the treatment schedule with HBV inoculum ($10^3$ Geq per cell) and serum samples (Neutralizing Ab). HepG2-hNTCP cells were treated with pre-bleed serum at a 1:1000 dilution (D) or immune sera from macaques at !:300, 1:1000 or 1:3000 dilution for 16 hours after the time of the HBV inoculation. At 1 day post infection (dpi), the mediums containing 2.5% DMSO were replaced. The cccDNAs were extracted at 3 dpi, and analyzed by real-time PCR. (B) HepG2-hNTCP cells infected with HBV ($10^3$ Geq/cell) were treated with sera as indicated (1:300 D=dilution of the original serum stock to 1/300 as vol/vol, 1:1000 D=dilution of the original serum stock to 1/1000 as vol/vol, 1:3000 D=dilution of the original serum stock to 1/3000 as vol/vol). Pre-bleed serums (1/1000 dilution (vol/vol)) were included as a control. At 3dpi, cccDNAs were analyzed by real-time PCR. Following digestion of T5 exonuclease, cccDNA was specifically quantified using specific primers. cccDNA was normalized as a ratio to mitochondrial DNA. Representative data are shown with quantification (means±standard deviation) (n=2).
Figure 6:
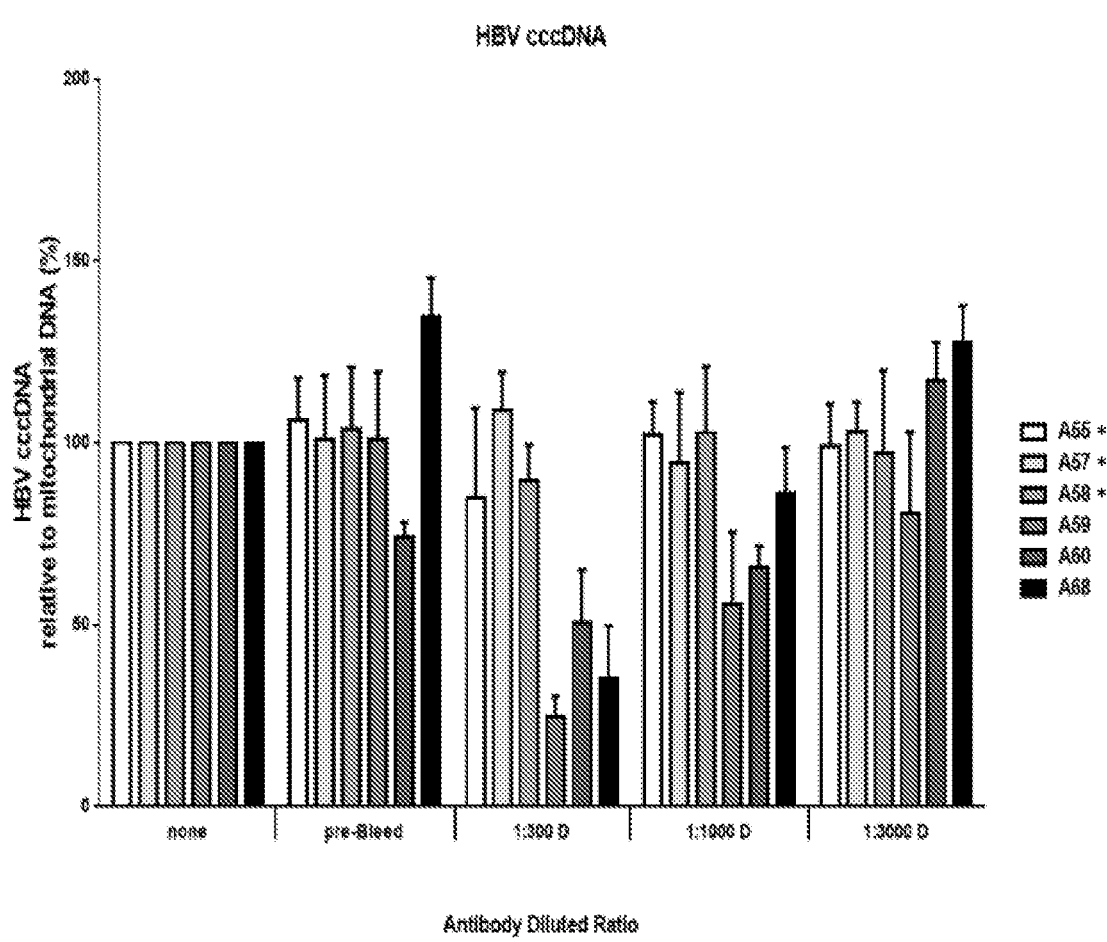

Induction in Macaques of HBV-Specific Neutralizing Antibodies (Abs) by G28-8LH-scAb-PreS1-S2-His To determine the frequency neutralizing antibodies (Abs) to HBV after vaccination of the macaques, sera were from macaques before (pre-bleed) and 14 days after the second immunization as noted in Example 3. HBV particles were obtained from the culture supernatants of HepAD38 cells as an HBV-productive cell line. For HBV infection, HepG2 liver cells expressing the NTCP receptor for HBV (HepG2-hNTCP cells) were seeded in 60-mm dishes or 6-well plates coated with collagen type 1. After one day, cells were inoculated with HBV virions at $10^3$ genome equivalents (Geq) per cell in completed DMEM containing 4% polyethylene glycol (PEG) 8000 for 16 h. Then, cells were maintained in completed DMEM containing 2.5% DMSO for additional days. For the virus neutralizing experiment, the sera being tested for neutralizing Abs were added during the inoculation (16 h) as indicated in FIG. 6A.

For analysis of HBV cccDNAs, viral cccDNAs were isolated with the Hirt Extraction Method, for protein-free DNA extraction from HBV-infected cells. Briefly, cells from 60-mm dishes were lysed in 1 ml of lysis buffer containing 50 mM Tris-HCl (pH 7.4), 150 mM NaCl, 10 mM EDTA, and 1% SDS. After 1 h of incubation at room temperature, the lysates were transferred into a 2-ml tube, and this step was followed by the addition of 0.25 ml of 2.5 M KCl, then incubation at 4° C. overnight. The lysates were clarified by centrifugation and extracted with phenol-chloroform. DNA was precipitated with isopropanol overnight and dissolved in Nuclease-free water. The extracted DNA was treated with Plasmid-Safe ATP-dependent Dnase for southern blot analysis or T5 exonuclease for real-time PCR. For real-time PCR, total DNAs were purified from infected cells using DNeasy™ Blood & Tissue Kit (Qiagen). cccDNA levels were expressed as a normalized ratio to mitochondrial DNA, and cccDNA were detected using specific PCR primers.

The sera tested for neutralizing Ab activity included the pre-bleed controls (1:1000 dilution) for each animal and sera obtained from immunized macaques day 14 after a second immunization. The immune sera were tested for neutralizing Ab activity at either a 1:300 dilution (D), a 1:1000 D or a 1:3000 D. Three sera from immunized macaques (day 14 boost) had neutralizing Ab activity that prevented HBV from expressing cccDNA in hepatocytes in vitro, two animals from group 1, and one from group 2 (FIG. 6B). Group 1: G28-8LH-scAb-PreS1-S2-His (300 ug) Monkey ID: A16157, A16159, A16160. Group 2: G28-8LH-scAb-PreS1-S2-His (300 ug)+AddaVax (100 µg) Monkey ID: A16155, A16158, A16168

LITERATURE

1. Bertoletti A, Ferrari C. Adaptive immunity in HBV infection. J Hepatol. 2016. 64:S71-83.
2. Chappell C P, Giltiay N V, Dresch C, Clark E A. Controlling immune responses by targeting antigens to dendritic cell subsets and B cells. Int Immunol. 2014. 26:3-11.
3. Kim H. N., et al., Hepatitis B vaccination in HIV-infected adults: current evidence, recommendations and practical considerations. International journal of STD & AIDS, 2009. 20:595-600.
4. Kubba, A. K., et al., Non-responders to hepatitis B vaccination: a review. Communicable disease and public health/PHLS, 2003. 6:106-12.
5. Ott, J. J., et al., Global epidemiology of hepatitis B virus infection: new estimates of age-specific HBcAg seroprevalence and endemicity. Vaccine 2012. 30:2212-9.
6. Weinbaum C M, Williams I, Mast E E, et al. Recommendations for identification and public health management of persons with chronic hepatitis B virus infection. Centers for Disease Control and Prevention (CDC). MMWR Recomm Rep. 2008. 57(RR-8):1-20.
7. Wasley A, Kruszon-Moran D, Kuhnert W, et al. The prevalence of hepatitis B virus infection in the United States in the era of vaccination. J Infect Dis. 2010. 202:192-201.
8. Mitchell T, Armstrong G L, Hu D J, Wasley A, Painter J A. The increasing burden of imported chronic hepatitis B-United States, 1974-2008. PLoS One. 2011. 6:e27717.
9. Hepatitis B vaccines. Releve epidemiologique hebdomadaire/Section d'hygiene du Secretariat de la Societe des Nations=Weekly epidemiological record/Health Section of the Secretariat of the League of Nations, 2004. 79:255-63.
10. Perz J F et al., The contributions of hepatitis B virus and hepatitis C virus infections to cirrhosis and primary liver cancer worldwide. J Hepatol 2006. 45:529-38.
11. Lavanchy, D., Hepatitis B virus epidemiology, disease burden, treatment, and current and emerging prevention and control measures. J Viral Hep 2004. 11:97-107.
12. Kim W R, Epidemiology of hepatitis B in the United States. Hepatology, 2009. 49: S28-34.
13. Wang L, Zou Z Q, Liu C X, Liu X Z. Immunotherapeutic interventions in chronic hepatitis B virus infection: a review. J Immunol Methods. 2014 May; 407:1-8.
14. Thai H, Campo D S, Lara J, et al. Convergence and coevolution of hepatitis B virus drug resistance. Nat Commun. 2012. 3:789.
15. Menéndez-Arias L, Alvarez M, Pacheco B. Nucleoside/nucleotide analog inhibitors of hepatitis B virus polymerase: mechanism of action and resistance. Curr Opin Virol. 2014. 8C:1-9.
16. Wiegand J, van Bömmel F, Berg T. Management of chronic hepatitis B: status and challenges beyond treatment guidelines. Semin Liver Dis 2010; 30:361-377.
17. Luckhaupt S E, Calvert G M. Deaths due to bloodborne infections and their sequelae among health-care workers. Am J Ind Med. 2008. 51:812-24.

18. Beck, J. and M. Nassal, Hepatitis B virus replication. World J Gastroenterol WJG, 2007. 13:48-64.
19. Bruss V. Hepatitis B virus morphogenesis. World J Gastroenterol. 2007. 13:65-73.
20. Gerlich W H. Prophylactic vaccination against hepatitis B: achievements, challenges and perspectives. Med Microbiol Immunol. 2015. 204:39-55.
21. Eng N F, Bhardwaj N, Mulligan R, Diaz-Mitoma F. The potential of 1018 ISS adjuvant in hepatitis B vaccines: HEPLISAV™. Hum Vaccin Immunother. 2013. 9:1661-72.
22. Jilg W. Novel hepatitis B vaccines. Vaccine. 1998. 16 Suppl:S65-8.
23. Madalinski K, Sylvan S P, Hellstrom U, Mikolajewicz J, Zembrzuska-Sadkowska E, Piontek E. Antibody responses to preS components after immunization of children with low doses of BioHepB. Vaccine. 2001 Oct. 12; 20(1-2):92-7.
24. Rendi-Wagner P, Shouval D, Genton B, et al. Comparative immunogenicity of a PreS/S hepatitis B vaccine in non- and low responders to conventional vaccine. Vaccine. 2006. 24:2781-9.
25. Ni Y, Lempp F A, Mehrle S, et al. Hepatitis B and D viruses exploit sodium taurocholate co-transporting polypeptide for species-specific entry into hepatocytes. Gastroenterology. 2014 April; 146(4):1070-83.
26. Li W. NTCP is receptor for HBV The hepatitis B virus receptor. Annu Rev Cell Dev Biol. 2015; 31:125-47.
27. Chi S W, Kim J. Yi G S, Hong H J, Ryu S E. Broadly neutralizing anti-HBV antibody binds to non-epitope regions of preS1. FEBS Lett. 2009. 583:3095-100.
28. Ferrari C, Penna A, Bertoletti A et al. The preS1 antigen of hepatitis B virus is highly immunogenic at the T cell level in man. J Clin Invest. 1989. 84:1314-9.
29. Krawczyk A, Ludwig C, Jochum C et al. Induction of a robust T- and B-cell immune response in non- and low-responders to conventional vaccination against hepatitis B by using a third generation PreS/S vaccine. Vaccine. 2014. 32:5077-82.
30. Dion S, Bourgine M, Godon O, Levillayer F, Michel M L. Adeno-associated virus-mediated gene transfer leads to persistent hepatitis B virus replication in mice expressing HLA-A2 and HLA-DR1 molecules. J Virol. 2013 May; 87(10):5554-63.
31. Bian Y, Zhang Z, Sun Z et al. Vaccines Targeting PreS1 Domain Overcome Immune Tolerance in HBV Carrier Mice. Hepatology. 2017 Apr. 26. doi: 10.1002/hep.29239. [Epub ahead of print]
32. Valentine M A, Clark E A, Shu G L, Norris N A, Ledbetter J A. Antibody to a novel 95-kDa surface glycoprotein on human B cells induces calcium mobilization and B cell activation. J Immunol. 1988. 140:4071-8.
34. Miyake, K., et al., Murine B cell proliferation and protection from apoptosis with an antibody against a 105-kD molecule: unresponsiveness of X-linked immunodeficient B cells. J Exp Med 1994. 180:1217-24.
34. Miyake, K., et al., RP105, a novel B cell surface molecule implicated in B cell activation, is a member of the leucine-rich repeat protein family. J Immunol 1995. 154:3333-40.
35. Alving C R, Peachman K K, Rao M, Reed S G. Adjuvants for human vaccines. Curr Opin Immunol. 2012. 24:310-5.
36. Shimazu, R., et al., MD-2, a molecule that confers lipopolysaccharide responsiveness on Toll-like receptor 4. J Exp Med 1999. 189:1777-82.
37. Hebeis, B., et al., Vav proteins are required for B-lymphocyte responses to LPS. Blood, 2005. 106:635-40.
38. Hebeis, B. J., et al., Activation of virus-specific memory B cells in the absence of T cell help. J Exp Med 2004. 199:593-602.
39. Yazawa, N., et al., CD19 regulates innate immunity by the toll-like receptor RP105 signaling in B lymphocytes. Blood, 2003. 102:1374-80.
40. Chaplin, J. W., et al., Anti-CD180 (RP105) activates B cells to rapidly produce polyclonal Ig via a T cell and MyD88-independent pathway. J Immunol, 2011. 187: 4199-209.
41. Schultz T E, Blumenthal A. The RP105/MD-1 complex: molecular signaling mechanisms and pathophysiological implications. J Leukoc Biol. 2017 Jan; 101(1):183-192.
42. Ohto U, Miyake K, Shimizu T. Crystal structures of mouse and human RP105/MD-1 complexes reveal unique dimer organization of the toll-like receptor family. J Mol Biol. 2011 Nov. 4; 413(4):815-25
43. Yoon S I, Hong M, Wilson I A. An unusual dimeric structure and assembly for TLR4 regulator RP105-MD-1. Nat Struct Mol Biol. 2011 Aug. 21; 18(9):1028-35.
45. Chaplin J W, Chappell C P, Clark E A. Targeting antigens to CD180 rapidly induces antigen-specific IgG, affinity maturation and immunologic memory. 2013. J Exp Med 210:2135-46.
46. Ramos, H. J. and M. Gale, Jr., RIG-I like receptors and their signaling crosstalk in the regulation of antiviral immunity. Curr Opin Virol, 2011. 1:67-76.
47. Maxon E R, Siegrist C A. The next decade of vaccines: societal and scientific challenges. Lancet. 2011. 378:348-59.
48. Liang Y et al., Predictors of relapse in chronic hepatitis B after discontinuation of anti-viral therapy. Aliment Pharmacol Ther, 2011. 34:344-52.
49. Suthar M S, Diamond M S, Gale M, Jr. West Nile virus infection and immunity. 2013. Nat Rev Microbiol 11:115-128.
50. Coffman R L, Sher A, Seder R A. Vaccine adjuvants: putting innate immunity to work. Immunity. 2010. 33:492-503.
51. Clark E A, Shu G L, Lüscher B, Draves K E, Banchereau J, Ledbetter J A, Valentine M A. Activation of human B cells. Comparison of the signal transduced by IL-4 to four different competence signals. J Immunol. 1989. 143: 3873-80.
Loudon P T, Yager E J, Lynch D T, Narendran A, Stagnar C, Franchini A M, Fuller J T, White P A, Nyuandi J, Wiley C A, Murphey-Corb M, Fuller D H. GM-CSF increases mucosal and systemic immunogenicity of an H1N1 influenza DNA vaccine administered into the epidermis of non-human primates. PLoS One. 2010. 5:e11021.
Toita R, Kawano T, Kang J H, Murata M. Applications of human hepatitis B virus preS domain in bio- and nanotechnology. World J Gastroenterol. 2015 Jun. 28; 21(24): 7400-11.
Chen Y, Bai Y, Guo X, Wang W, et al. Selection of affinity-improved neutralizing human scFv against HBV PreS1 from CDR3 VH/VL mutant library. Biologicals. 2016 July; 44(4):271-5.

We claim:

1. A polypeptide, comprising an amino acid sequence having at least 90% identity to the amino acid sequence of SEQ ID NO:67 residues 21-697.

2. The polypeptide of claim 1, comprising an amino acid sequence having at least 95% identity to the amino acid sequence of SEQ ID NO:67 residues 21-697.

3. The polypeptide of claim 1, comprising an amino acid sequence having at least 98% identity to the amino acid sequence of SEQ ID NO:67 residues 21-697.

4. The polypeptide of claim 1, comprising the amino acid sequence of SEQ ID NO:67 residues 21-697.

5. The polypeptide of claim 1 comprising an amino acid sequence having at least 90% identity to the amino acid sequence of SEQ ID NO:67.

6. The polypeptide of claim 1, comprising an amino acid sequence having at least 95% identity to the amino acid sequence of SEQ ID NO:67.

7. The polypeptide of claim 1, comprising an amino acid sequence having at least 98% identity to the amino acid sequence of SEQ ID NO:67.

8. The polypeptide of claim 1, comprising the amino acid sequence of SEQ ID NO:67.

9. An isolated nucleic acid encoding the polypeptide of claim 1.

10. An expression vector comprising the isolated nucleic acid of claim 9 operatively linked to a suitable control sequence.

11. A recombinant host cell comprising the expression vector of claim 10.

12. A pharmaceutical composition, comprising
   (a) the polypeptide claim 1; and
   (b) a pharmaceutically acceptable carrier.

13. A method for treating or limiting the development of a hepatitis-B virus (HBV)-related disorder, comprising administering to an individual in need thereof an amount effective to treat or limit development of the HBV-related disorder of the polypeptide of claim 1, or pharmaceutically acceptable salts thereof.

14. An isolated nucleic acid encoding the polypeptide of claim 4.

15. An isolated nucleic acid encoding the polypeptide of claim 8.

16. An isolated nucleic acid encoding the polypeptide of claim 14, wherein the nucleic acid comprises the nucleotide sequence of SEQ ID NO:68.

17. An expression vector comprising the isolated nucleic acid of claim 14 operatively linked to a suitable control sequence.

18. An expression vector comprising the isolated nucleic acid of claim 15 operatively linked to a suitable control sequence.

19. An expression vector comprising the isolated nucleic acid of claim 16 operatively linked to a suitable control sequence.

20. A recombinant host cell comprising the expression vector of claim 17.

21. A recombinant host cell comprising the expression vector of claim 18.

22. A recombinant host cell comprising the expression vector of claim 19.

23. A method for treating or limiting the development of a hepatitis-B virus (HBV)-related disorder, comprising administering to an individual in need thereof an amount effective to treat or limit development of the HBV-related disorder of the polypeptide of claim 4, or pharmaceutically acceptable salts thereof.

24. A method for treating or limiting the development of a hepatitis-B virus (HBV)-related disorder, comprising administering to an individual in need thereof an amount effective to treat or limit development of the HBV-related disorder of the polypeptide of claim 8, or pharmaceutically acceptable salts thereof.

* * * * *